(12) United States Patent
Slack et al.

(10) Patent No.: US 8,124,361 B2
(45) Date of Patent: *Feb. 28, 2012

(54) METHODS OF SCREENING FOR SWEET TASTE MODULATORS

(75) Inventors: Jay Patrick Slack, Loveland, OH (US); Christopher Todd Simons, Wyoming, OH (US); Chad Allen Hansen, Kings Mills, OH (US)

(73) Assignee: Givaudan SA, Vernier (CH)

(*) Notice: Subject to any disclaimer, the term of this patent is extended or adjusted under 35 U.S.C. 154(b) by 115 days.

This patent is subject to a terminal disclaimer.

(21) Appl. No.: 12/297,851

(22) PCT Filed: Apr. 20, 2007

(86) PCT No.: PCT/CH2007/000190
§ 371 (c)(1),
(2), (4) Date: Jan. 16, 2009

(87) PCT Pub. No.: WO2007/121604
PCT Pub. Date: Nov. 1, 2007

(65) Prior Publication Data
US 2009/0311686 A1  Dec. 17, 2009

Related U.S. Application Data

(60) Provisional application No. 60/793,686, filed on Apr. 20, 2006, provisional application No. 60/793,521, filed on Apr. 20, 2006, provisional application No. 60/814,866, filed on Jun. 19, 2006, provisional application No. 60/853,813, filed on Oct. 24, 2006, provisional application No. 60/853,821, filed on Oct. 24, 2006, provisional application No. 60/853,823, filed on Oct. 24, 2006, provisional application No. 60/881,402, filed on Jan. 19, 2007.

(51) Int. Cl.
*G01N 33/567* (2006.01)
*C07K 14/705* (2006.01)
*C12N 15/62* (2006.01)

(52) U.S. Cl. ........ 435/7.21; 435/7.1; 435/7.2; 435/69.7; 436/501; 536/23.4

(58) Field of Classification Search .................. None
See application file for complete search history.

(56) References Cited

U.S. PATENT DOCUMENTS

| | | | |
|---|---|---|---|
| 5,436,128 | A | 7/1995 | Harpold et al. |
| 5,919,649 | A | 7/1999 | Habener et al. |
| 6,383,778 | B1 | 5/2002 | Zuker et al. |
| 2003/0054448 | A1 | 3/2003 | Adler et al. |
| 2003/0232407 | A1 | 12/2003 | Zoller et al. |
| 2005/0032158 | A1 | 2/2005 | Adler et al. |

FOREIGN PATENT DOCUMENTS

| WO | 92/01810 | 2/1992 |
|---|---|---|
| WO | 01/18050 | 3/2001 |
| WO | 2004/055048 | 7/2004 |
| WO | 2006/113422 | 10/2006 |

OTHER PUBLICATIONS

Mun et al. "The Venus Fly Trap Domain of the Extracellular Ca2+-Sensing Receptor is Required for L-Amino Acid Sensing." Journal of Biological Chemistry, vol. 279, No. 50, Dec. 10, 2004, pp. 51739-51744.
Kanemaru et al. "Enhancement of Sucrose Sweetness With Soluble Starch in Humans." Chemical Senses, vol. 27, No. 1, Jan. 2002, p. 67-72.
Li et al. "Human Receptors for Sweet and Umami Taste." PNAS, vol. 99, No. 7, Apr. 2, 2002, pp. 4692-4696.
Broach et al. "High-Throughput Screening for Drug Discovery." Nature, vol. 384, Supp., Nov. 7, 1996, pp. 14-16.
Knight et al. "Chimeric G Proteins Extend the Range of Insect Cell-Based Functional Assays for Human G Protein-Coupled Receptors." Journal of Receptors and Signal Transduction, vol. 24, No. 4, 2004, pp. 241-256.
Kenimer et al. "Desensitization of Adenylate Cyclase to Prostaglandin E1 or 2-Chloroadenosine." Molecular Pharmacology, vol. 20, No. 3, Nov. 1981, pp. 585-591.
Traynor et al. "Modulation by μ-Opioid Agonists of Guanosine-5'-O-(3[35S]thio)triphosphate Binding to Membranes from Human Neuroblastoma SH-SY5Y Cells." Molecular Pharmacology, vol. 47, 1995, pp. 848-854.
Hafner, "Cytosensor® Microphysiometer: Technology and Recent Applications." Biosensors & Bioelectronics, vol. 15, 2000, pp. 149-158.
Gijon et al. "Cytosolic Phospholipase A2 Is Required for Macrophage Arachidonic Acid Release by Agonists That Do and Do Not Mobilize Calcium." The Journal of Biological Chemistry, vol. 275, No. 26, Jun. 30, 2000, pp. 20146-20156.
Horton et al. "Mass Measurements of Cyclic AMP Formation by Radioimmunoassay, Enzyme Immunoassay, and Scintillation Proximity Assay." Methods in Molecular Biology, vol. 41, 1995, pp. 91-105.
Felley-Bosco et al. "Constitutive Expression of Inducible Nitric Oxide Synthase in Human Bronchial Epithelial Cells Induces c-fos and Stimulates the cGMP Pathway." American Journal of Respiratory Cell and Molecular Biology, vol. 11, 1994, pp. 159-164.
Kikkawa et al. "Calcium-Activated, Phospholipid-dependent Protein Kinase from Rat Brain." The Journal of Biological Chemistry, vol. 257, No. 22, Nov. 25, 1982, pp. 13341-13348.

(Continued)

*Primary Examiner* — John Ulm
(74) *Attorney, Agent, or Firm* — Kenyon & Kenyon LLP

(57) ABSTRACT

We have discovered a method to enhance sweetness comprising the use of a sweetener at a sub- to near-threshold concentration which is used in combination with a suprathreshold concentration of another sweetener. The sweetener used at the near-threshold concentration is selected based on its likely binding site in the human sweet taste receptor. The invention relates to the identification of agents that can modulate the taste response in humans (such as sweet taste enhancers) through assays based on a novel sweet receptor protein, heterologous expression systems containing nucleic acid constructs forming said novel sweet receptor protein, and the use of the novel sweet receptor protein in screening.

21 Claims, 1 Drawing Sheet

OTHER PUBLICATIONS

Pinna et al. "How Do Protein Kinases Recognize Their Substrates?" Biochimica et Biophysica Acta, 1996, pp. 191-225.

Bufe et al. "The Human TAS2R16 Receptor Mediates Bitter Taste in Response to β-Glucopyranosides." Nature Genetics, vol. 32, Nov. 2002, pp. 397-401.

O'Mahony "Understanding Discrimination Tests: a User-Friendly Treatment of Response Bias, Rating and Ranking R-Index Tests and Their Relationship to Signal Detection." Journal of Sensory Studies, vol. 7, 1992, pp. 1-47.

Schiffman, Susan S., et al., "Selective Inhibition of Sweetness by the Sodium Salt of ±2-(4-Methoxyphenoxy) propanoic Acid", Chem. Senses, 1999, vol. 24, pp. 439-447.

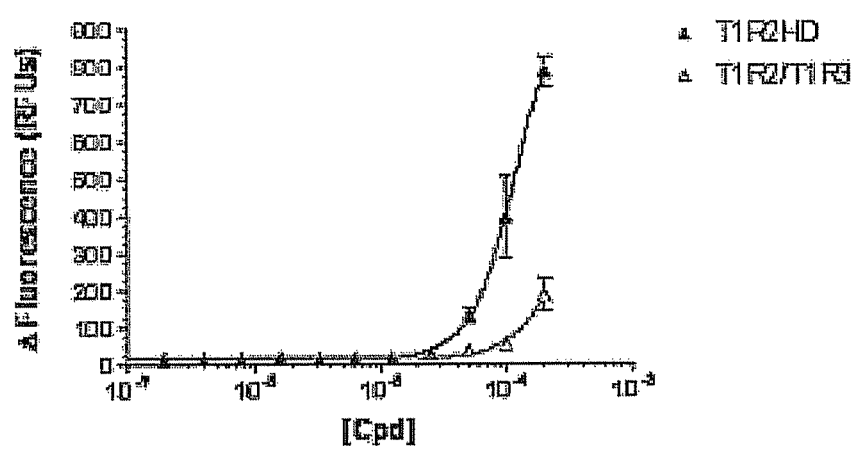
Fig. 1 Dose response curves of the T1R2-TMD homomer (filled-in triangles) and the T1R2/T1R3 heterodimer (open triangles).

METHODS OF SCREENING FOR SWEET TASTE MODULATORS

CROSS REFERENCE TO RELATED APPLICATION

This application is a 371 of International Patent Application No. PCT/CH2007/000190, filed Apr. 20, 2007, which claims priority to U.S. Patent Application No. 60/793,521, filed Apr. 20, 2006, U.S. Patent Application No. 60/793,686, filed Apr. 20, 2006, U.S. Patent Application No. 60/814,866, filed Jun. 19, 2006, U.S. Patent Application No. 60/853,813, filed Oct. 24, 2006, U.S. Patent Application No. 60/853,821, filed Oct. 24, 2006, U.S. Patent Application No. 60/853,823, filed Oct. 24, 2006, and U.S. Patent Application No. 60/881,402, filed Jan. 19, 2007. The contents of these applications are hereby incorporated by reference in their entireties.

BACKGROUND OF THE INVENTION

The invention relates to the identification of agents that can modulate the taste response in humans (in particular sweetness enhancers) through assays based on novel sweet receptor proteins, heterologous expression systems containing nucleic acid constructs forming said sweet receptor protein, and the use of the sweet receptor protein in screening. The sweetness enhancers render certain foods more palatable or increase patient compliance in oral pharmaceutics and nutraceutics. Such sweetness enhancers include sweet tastants that elicit a taste response in humans.

Sweetness modulators and in particular sweetness enhancers are of great use and interest to the food and flavor industry, for example, to allow reduction of the level of sweeteners, including sugars and artificial sweeteners, in consumable products. The use of sweetness enhancers can reduce calories, prevent teeth from damage by sugars, and avoid or reduce the bitter/metallic off- and aftertastes associated with many artificial sweeteners.

The detection of sweet taste is known to be mediated by a receptor, TAS1R, comprised of two subunits, T1R2 and T1R3, which are specifically expressed in taste receptor cells, and form a dimeric sweet taste receptor complex (T1R2/T1R3 heterodimer). Both subunits belong to the family of so-called "G-protein coupled receptors" or GPCRs, in particular class-C GPCRs.

Like most other GPCRs, the class-C receptors have a heptahelical transmembrane domain (TMD). However, unlike other types of GPCRs, the class-C GPCRs also have a large extracellular domain composed of two parts: a "venus flytrap module" (VFTM) that is involved in ligand binding; and a cysteine-rich domain (CRD) that contains nine highly conserved cysteines and that links the VFTM to the TMD. A variable length intracellular C-terminal tail completes the class-C receptor.

Activation of the sweet receptor response was thought to require both subunits of the dimeric sweet receptor complex, and to date, all sweeteners tested activate the T1R2/T1R3 heterodimer. Published tests conducted with the separate subunits of the human sweet receptor (T1R2 homomer or T1R3 homomer) have shown no activity, while the T1R2/T1R3 heterodimer responds to a broad spectrum of chemically diverse sweeteners, ranging from natural sugars (sucrose, fructose, glucose, maltose), sweet amino acids (D-tryptophan), and artificial sweeteners (acesulfame-K, aspartame, cyclamate, saccharin, sucralose), to sweet tasting proteins (monellin, thaumatin, brazzein) (see for example Li et al., 2002, *Proc. Natl. Acad. Sci. USA*, 99(7), 4692-6).

Currently known screens for sweetness modulators employ the T1R2/T1R3 heterodimeric sweet receptor. These screens usually identify or characterize a sweetness modulator by comparing the results of samples with and without a potential modulator in the presence of a sweetener. However, sweeteners and in particular sugars have a great effect on osmolarity, and/or are viscous. Due to changes in properties of the samples such as viscosity and osmolarity, artifacts may occur that cause incorrect results when using standard screening methods.

Another disadvantage of known screens is that the wild-type T1R2/T1R3 receptor comprises several binding domains, in particular the extracellular amino terminal domains including the venus flytrap ("VFT") domain that bind to carbohydrate sweeteners such as sucrose, glucose, fructose as well as the artificial sweeteners aspartame and sucralose. Therefore, a screen for specific modulators of specific ligands, and in particular for ligands of the transmembrane domains ("TMD(s)"), excluding the VFT ligands, is not possible with known screening methods.

In order to prevent identification of agents that may compete with sugars for binding to the receptor, a screen that allows identification of putative sweet receptor enhancers that bind at a site physically distinct from the VFT domains, and in particular in the TMD and/or cysteine-rich domains, would be desirable. The present invention addresses this need. For example, the inventive method using chimeric T1R receptors created by the applicant (CSR:T1R2 or CSR:T1R3 chimeric receptors, collectively the CSR:T1R chimeric receptors ("CSR" refers to the calcium-sensing receptor)) indicates that the sweet compound cyclamate binds in the TMD of T1R3, thereby activating the heterodimeric T1R2/T1R3 receptor complex.

To date, it was unknown that the TMD of one of the TAS1R monomers could bind sweet compounds and additionally activate G-proteins in the absence of the other obligate monomeric partner. Previously, the field believed the presence of both subunits was essential for signal transduction. Applicant has found that a novel receptor protein ("T1R2-TMD") corresponding to a heavily truncated sequence of the T1R2 homomer of the T1R2/T1R3 heterodimer receptor complex forms, surprisingly, a functional sweet receptor that binds to a sweet ligand and is able to activate G-proteins. The novel receptor protein T1R2-TMD was found to have a different agonist spectrum than the full-length T1R2 homomer. The former was surprisingly found to be able not only to bind to ligands but also to activate downstream signaling.

The methods provided herein permit the identification of ligands that bind to and/or activate the transmembrane and intra-cellular domains of T1R2 and/or T1R3. Accordingly, cells expressing either CSR:T1R chimeric receptors or T1R2-TMD and a G-protein, are contacted with test agents, optionally in combination with known or newly determined sweet tastants, to determine the properties of said agents as sweetness enhancers. The assays provided herein may therefore be used to identify a tested agent as sweet tastant or enhancer of the sweet response. The functional effects of the agent on the receptor and G-protein are determined by a suitable functional assay, for example, an assay that measures changes in parameters of the transduction pathways such as intracellular $IP_3$ and $Ca^{2+}$, or by other G-protein specific assays such as labeling with GTPγS, according to techniques known in the art. Alternatively, binding assays may be used to determine ligand binding to CSR:T1R chimeric receptors or T1R2-TMD. The identified agent can then be tested for its activity as a sweetness enhancer, according to techniques known in the art, described without limitation herein below.

In practicing the various aspects and embodiments described herein in relation to cloning, elucidating ligand-receptor pairs, and finding enhancers of the sweet response, recourse is made to conventional techniques in molecular biology, microbiology and recombinant technology and sweetness testing. These include the various known methods suitable for G-protein coupled receptors (GPCRs) including CSR:T1R chimeric receptors or T1R2-TMD. Accordingly, the skilled person is fully apprised of such techniques and as such they are hereafter treated only summarily in order to more fully describe the context of the present invention.

SUMMARY

In its first aspect the invention comprises: an agent that, when mixed at a concentration near or just below the sweetness threshold with a known or pre-determined sweet tastant at a concentration above the sweetness threshold, enhances the sweetness of the admixture of said agent and said known or pre-determined sweet tastant in a greater than additive manner compared to the sweetness of a mixture containing solely said sweet tastant or solely said agent; wherein said agent is identifiable by comparing the signal produced by an assay for activity of a taste receptor in the presence of said agent against the signal produced by an assay for activity of a taste receptor in the absence of said agent; wherein said assay for activity of a taste receptor comprises identifying agents that bind to the trans-membrane domain of a taste receptor while excluding agents that bind to the venus fly-trap domain of a taste receptor.

In a second aspect the invention comprises: a method of identifying a putative sweetness enhancer, comprising measuring the signal produced by an assay for binding to and/or activation of a taste receptor in the presence of said agent and the signal produced by the same assay in the absence of said agent and comparing the two measurements; wherein said assay comprises identifying agents that bind to and/or activate the trans-membrane domain of a taste receptor while excluding agents that bind to the venus fly-trap domain of a taste receptor by utilizing a protein comprising the trans-membrane and intracellular domains, but not the extracellular domain of a taste receptor joined to the extracellular domain of a G-protein coupled receptor other than the taste receptor.

In a third aspect the invention comprises: a method of identifying a putative sweetness enhancer; comprising measuring the signal produced by an assay for binding to and/or activation of a taste receptor in the presence of said agent and the signal produced by the same assay in the absence of said agent and comparing the two measurements; wherein said assay comprises identifying agents that bind to the trans-membrane domain of a taste receptor while excluding agents that bind to the venus fly-trap domain of a taste receptor by utilizing a protein comprising a truncated taste receptor that lacks the venus fly-trap domain of the taste receptor.

In a fourth aspect the invention comprises: a method of identifying a putative sweetness enhancer; comprising measuring the signal produced by an assay for activity of a taste receptor in the presence of said agent and the signal produced by an assay for activity of a taste receptor in the absence of said agent and comparing the two measurements, wherein said assay for activity of a taste receptor comprises identifying agents that bind to the transmembrane domain of the T1R2 sub-unit of the TAS1R taste receptor while excluding agents that bind to the venus fly-trap domain of a taste receptor by utilizing a protein comprising a taste receptor that has been truncated to remove the venus fly-trap domain of a taste receptor.

In further aspects the invention comprises a method of enhancing the sweetness of a sweetener comprising: admixing a sweetness enhancer identified by the methods disclosed herein with a sweetener, wherein the sweetener is present in a concentration of at least 2% isointensity to sucrose and wherein a sweetness enhancer is present in a concentration from at least 1 ppb to 100,000 ppm, and if the sweetness enhancer is also a sweetener, it is present in a concentration near its sweetness detection threshold at an isointensity to sucrose of less than 2% (w/w) sucrose. The sweetness enhancer can be a single compound or a mixture of compounds.

In yet further aspects the invention comprises methods of identifying putative sweetness enhancers; comprising combining sub-units of a chimeric taste receptor in which the wildtype venus fly-trap domain has been replaced by an alternative class C GPCR venus fly-trap domain and sub-units of the wildtype taste receptor; wherein the assay comprises measuring the signal produced by an assay for activity of the combined chimeric receptor/wildtype taste receptor dimer in the presence of said agent and the signal produced by an assay for activity of the combined chimeric receptor/wildtype taste receptor in the absence of said agent and comparing the two measurements.

In a further aspect the invention comprises a method of identifying a compound that binds to and/or activates a taste receptor outside the venus flytrap domain of the taste receptor comprising contacting a modified taste receptor with a compound and determining whether the compound binds to and/or activates the modified receptor, wherein the modified receptor comprises a polypeptide selected from the group consisting of:

a) T1R2 lacking its venus flytrap domain and/or T1R3 lacking its venus flytrap domain, b) T1R2-TMD, CSR:T1R, T1R3-TMD, both T1R2-TMD and T1R3-TMD, CSR:T1R2, CSR:T1R3, both CSR:T1R2 and T1R3-TMD, both T1R2-TMD and CSR:T1R3, c) a chimeric protein comprising a venus flytrap domain derived from a class C G-protein coupled receptor and T1R2 lacking its venus flytrap domain and/or a chimeric protein comprising a venus flytrap domain derived from a class C G-protein coupled receptor and T1R3 lacking its venus flytrap domain, d) any protein that is at least 95% identical at the amino acid level to any of the proteins listed in a)-c), e) any protein that is substantially homologous to any of the proteins listed in a)-c), f) any protein that is encoded by SEQ ID NOS: 1, 13, 15, and 27, g) any protein that is encoded by a nucleic acid that hybridizes under stringent conditions to SEQ ID NOS: 1, 13, 15, and 27, wherein the modified receptor optionally further comprises one or more sequence tags selected from a signal sequence and an antibody epitope, and provided that at least one subunit of the modified receptor does not comprise a T1R2 or T1R3 venus flytrap domain.

In a further aspect the invention comprises a method of identifying a compound or group of compounds that enhances sweet taste comprising a) determining whether a compound or group of compounds binds to and/or activates a taste receptor outside a taste receptor's venus flytrap domain comprising contacting a modified taste receptor with a compound or group of compounds and determining whether the compound or group of compounds binds to and/or activates the modified receptor, and b) determining whether a compound or group of compounds that binds to and/or activates a modified receptor enhances sweet taste by
  i) determining whether the compound or group of compounds enhances binding to and/or activation of a chimeric receptor by a ligand for the receptor, or
  ii) determining whether the compound or group of compounds enhances sweet taste of a sweetener, wherein the sweetener is present at a concentration isosweet to a sucrose solution of concentration 2% or greater and the compound is present at a concentration isosweet to a sucrose solution of less than 2% concentration, wherein the chimeric receptor comprises a subunit comprising 1) a venus flytrap domain derived from a class C G-protein coupled receptor, and 2) T1R2 lacking its venus flytrap domain, and optionally a subunit comprising 1) a venus flytrap domain derived from a class C G-protein coupled receptor, and 2) T1R3 lacking its venus flytrap domain, wherein at least one subunit does not comprise a T1R2 or T1R3 venus flytrap domain, and wherein the modified receptor comprises a polypeptide selected from the group consisting of:
  a) T1R2 lacking its venus flytrap domain and/or T1R3 lacking its venus flytrap domain,
  b) T1R2-TMD, CSR:T1R, T1R3-TMD, both T1R2-TMD and T1R3-TMD, CSR:T1R2, CSR:T1R3, both CSR:T1R2 and T1R3-TMD, both T1R2-TMD and CSR:T1R3,
  c) a chimeric protein comprising a venus flytrap domain derived from a class C G-protein coupled receptor and T1R2 lacking its venus flytrap domain and/or a chimeric protein comprising a venus flytrap domain derived from a class C G-protein coupled receptor and T1R3 lacking its venus flytrap domain,
  d) any protein that is at least 95% identical at the amino acid level to any of the proteins listed in a)-c)
  e) any protein that is encoded by SEQ ID NOS: 1, 13, 15, 27,
  f) any protein that is encoded by a nucleic acid that hybridizes under stringent conditions to SEQ ID NOS: 1, 13, 15, and 27, wherein the modified receptor optionally further comprises one or more sequence tags selected from a signal sequence and an antibody epitope, and provided that at least one subunit of the modified receptor does not comprise a T1R2 or T1R3 venus flytrap domain.

In certain illustrative embodiments, the methods as defined herein-above utilizes cells that also express a G-protein.

In certain illustrative embodiments, the methods as defined herein-above utilizes cells that have been transiently or stably transfected with one or more nucleic acids that encode a protein comprising the transmembrane domain of T1R2 and/or T1R3.

In other embodiments, according to the method as defined herein-above, the G-protein is a chimeric G-protein based on Gaq-Gustducin.

In further embodiments, according to the methods as defined herein-above, the G-protein is the chimeric G-protein Galpha16-gustducin 44.

In still further embodiments, according to the methods as defined herein-above, determination of whether at least one agent affects the functional activity of the taste receptor in cells by at least one functional response in the cells is performed by measuring a change in or caused by intracellular messengers.

In yet further embodiments, according to the methods as defined herein-above, the functional response is determined by measuring a change in an intracellular messenger selected from IP3 and calcium$^{2+}$.

In other embodiments, according to the methods as defined herein-above, the cells are selected from the group consisting of bacterial cells, eucaryotic cells, yeast cells, insect cells, mammalian cells, amphibian cells, and worm cells.

In certain embodiments, according to the methods as defined herein-above, the cells are mammalian cells.

In further embodiments, according to the methods as defined herein-above, the cells are mammalian cells selected from the group consisting of CHO, COS, HeLa and HEK-293 cells.

In still further embodiments, according to the methods as defined herein-above, (i) further comprises contacting the T1R2 sweet receptor with a test agent in presence of a sweet tastant.

In another aspect, a kit is provided, the kit comprising:
  (i) recombinant cells that express a T1R2-TMD sweet receptor, or a substantially similar homologue thereof, but that do not express a T1R3 receptor, and
  (ii) an agonist of the T1R2-TMD sweet receptor,
for combined use to identify test agents as modulators of the T1R2-TMD.

In another aspect, provided is a method of using the kit defined herein-above. The method comprises:
  (i) growing recombinant cells on a solid support;
  (ii) adding test agents to a culture medium of defined plates or wells in the presence of the agonist in a suitable concentration, and
  (iii) determining a change in a functional response of the cells by comparing the response in presence and absence of the test agent, and the test agent is thereby identified as a modulator of the T1R sweet receptor or a substantially similar homologue thereof.

In another aspect, provided is a method to identify an agent that modulates T1R2-TMD, the method comprising:
  (i) measuring a parameter that changes in response to ligand binding to T1R2-TMD
  (ii) determining a change of the parameter in response to a test agent, optionally in presence of a ligand, in comparison to a negative control and thereby identifying a modulator or ligand.

In certain embodiments, according to the methods as defined herein-above, the ligand is selected from the group consisting of perillartine, p-ethoxybenzaldehyde, cinnamonitrile, stevioside, rubusoside, rebaudioside A and neohesperidin dihydrochalcone.

In certain embodiments, according to the method as defined herein-above, (i) is performed by a method selected from the group consisting of fluorescence spectroscopy, NMR spectroscopy, measuring of one or more of absorbance, refractive index, hydrodynamic methods, chromatography, measuring solubility, biochemical, wherein the methods measure the properties of the T1R2-TMD polypeptide in a suitable environment selected form the group consisting of solution, bilayer membrane, attached to a solid phase, in a lipid monolayer, bound on a membrane, and in vesicles.

Embodiments of the invention encompass the above methods except provided that the invention does not encompass methods that employ both full-length wild-type T1R2 and full-length wild-type T1R3 protein.

In a further aspect the invention comprises a method of enhancing sweet taste in a consumable comprising including in the consumable a sweet enhancer below or near its sweet detection threshold at a concentration isosweet to a sucrose solution of less than 2% concentration, wherein the consumable contains a sweetener at a concentration above its sweetness detection threshold.

DETAILED DESCRIPTION

Candidate Sweetness Enhancers

A compound or group of compounds is a sweetness enhancer if a mixture containing the putative enhancer and a sweetener is sweeter than the sum of the sweetness of the putative enhancer alone (at the same concentration as in the mixture) plus the sweetness of the sweetener alone (at the same concentration as in the mixture). The applicants have identified as candidate sweetness enhancers, without limitation, the following compounds which bind to the transmembrane domains of TAS1R: perillartine, p-ethoxybenzaldehyde, cinnamonitrile, naringin dihydrochalcone, cyclamate, stevioside, rubusoside, rebaudioside A, mogroside V, neohesperidin dihydrochalcone. The chemical structures for perillartine, p-ethoxybenzaldehyde, cinnamonitrile, stevioside, rubusoside, rebaudioside A and neohesperidin dihydrochalcone can be found at the United States National Library of Medicine information website. The chemical structure of naringin dihydrochalcone is known in the art. The chemical structure of cyclamate is known in the art. The chemical structure of mogroside V is known in the art. The candidate sweetness enhancers can be used in purified or isolated form or in the form of a botanical extract comprising the sweetness enhancing actives.

Sweeteners

Sweeteners are compounds that increase the sweetness of taste. The sweeteners include, but are not limited to, the sugars sucrose, fructose, glucose, high fructose corn syrup (containing fructose and glucose), tagatose, galactose, ribose, xylose, arabinose, and rhamnose, the sugar alcohols erythritol, xylitol, mannitol, sorbitol, and inositol, and the artificial sweeteners AceK, aspartame, neotame, sucralose, and saccharine, and combinations of these sweeteners.

Sucrose, also known as table sugar or saccharose, is a disaccharide of glucose and fructose. Its systematic name is α-D-glucopyranosyl-(1→2)-β-D-fructofaranose. Fructose, glucose, tagatose, galactose, ribose, xylose, arabinose and rhamnose are monosaccharide sugars. High fructose corn syrup (HFCS) consists of a mixture of glucose and fructose. Like ordinary corn syrup, the high fructose variety is made from corn starch using enzymes. The fructose content of corn syrup (glucose) is increased through enzymatic processing. Common commercial grades of high fructose corn syrup include fructose contents of 42%, 55%, or 90%. The 55% grade is most commonly used in soft drinks. Erythritol (systematic name 1,2,3,4-butanetetrol) is a natural non-caloric sugar alcohol. AceK, aspartame, neotame and sucralose are artificial sweeteners. Acesulfam potassium (AceK) is the potassium salt of 6-methyl-1,2,3-oxathiazine-4(3H)-one 2,2-dioxide, an N-sulfonylamide. It is also known as Acesulfam K or AceK, or under various trademark names including Sunett® and Sweet One®. In the European Union it is also known under the E number (additive code) E950. Aspartame is the name for aspartyl-phenylalanine-1-methyl ester, a dipeptide. It is known under various trademark names including Equal®, and Canderel®. In the European Union, it is also known under the E number (additive code) E951. Sucralose is the name for 6-dichloro-1,6-dideoxy-β-D-fructo-furanosyl 4-chloro-4-deoxy-α-D-galactopyranoside, which is a chlorodeoxysugar. It is also known by the trade name Splenda®. In the European Union, it is also known under the E number (additive code) E955.

The natural sweeteners may be used in pure or partly purified form, and may be prepared by any method, including chemical synthesis, biotechnological processes including fermentation, or isolation from a natural source, in particular a botanical source (including, without limitation, fruits, sugar cane, sugar beet), for example a plant extract or syrup including, without limitation, corn syrup, high fructose corn syrup, honey, molasses, maple syrup, fruit concentrates, and other syrups and extracts.

Admixtures of Sweetness Enhancers and Sweeteners

The sweetness detection threshold for the sweetness enhancers and their combinations were determined by the applicant. The sweetness detection threshold is the minimum concentration required for a person to detect a difference in sweetness from non-sweet. The sweetness detection threshold varies somewhat in different individuals. For example, some individuals are able to detect the sweetness of sucrose in a very low concentration of 0.4%; others need at least 0.7% or even more. All examples were performed with sweet sensitive panelists at least able to detect 0.5% of sucrose or less. The concentration detectable by the average consumer will therefore be higher.

A sweetness enhancer's sweetness detection threshold is defined herein as a concentration with an isointensity to sucrose of less than 2% sucrose, for example, up to 1% sucrose, up to 0.8%, up to 0.75%, up to 0.7% sucrose, or up to 0.5% sucrose, as detected by sweet sensitive panelists. Combinations of these sweetness enhancers with each other and with optional ingredients were found to have a particularly high sweetness enhancing effect on a sweetener as described herein.

Uses of Sweetness Enhancers

The sweetness enhancers can be used as a single sweetness enhancing component in a concentration as indicated below in a formulation containing, for example, 0.0001% to 15% (wt/wt) or more of at least one sweetener. A useful concentration for a sweetener is a concentration that on its own provides an isointensity to a sucrose solution of at least 2%, for example 2% to 15%, or 5% to 12%. For example, a useful concentration of sucrose, fructose, glucose, high fructose corn syrup (HFCS) or erytiritol may be from about 5% to about 12%.

Consumables include all food products, including but not limited to, cereal products, rice products, tapioca products, sago products, baker's products, biscuit products, pastry products, bread products, confectionery products, dessert products, gums, chewing gums, chocolates, ices, honey products, treacle products, yeast products, baking-powder, salt and spice products, savory products, mustard products, vinegar products, sauces (condiments), tobacco products, cigars, cigarettes, processed foods, cooked fruits and vegetable products, meat and meat products, jellies, jams, fruit sauces, egg products, milk and dairy products, yoghurts, cheese products, butter and butter substitute products, milk substitute products, soy products, edible oils and fat products, medicaments, beverages, carbonated beverages, alcoholic drinks, beers, soft drinks, mineral and aerated waters and other non-alcoholic drinks, fruit drinks, fruit juices, coffee, artificial coffee, tea, cocoa, including forms requiring reconstitution, food extracts, plant extracts, meat extracts, condiments, sweeteners, nutraceuticals, gelatins, pharmaceutical and non-pharmaceutical gums, tablets, lozenges, drops, emulsions, elixirs, syrups and other preparations for making beverages, and combinations thereof.

Consumables may contain acids to provide a low pH. For example, many beverages have a low pH, for example, from pH 2.6 to 3. The sweetness enhancers herein-described also work under low pH conditions and show an enhancement effect. How to sweeten consumables using sweeteners herein-described in a sufficient amount is well-known in the art. Depending on the consumable, the amount of sweetener can be reduced by addition of the sweetness enhancers herein-described. For example, for sucrose as sweetener, a reduction of about 1 to 4° Bx (° Bx (degrees Brix) is a measurement of the mass ratio of dissolved sucrose to water in a liquid) or more can be achieved. Consumables may contain any amount of a sweetener as described herein. A useful range is, for example, at least 2%, for example about 2% to 15%, or about 5% to 12% of one or more selected from sucrose, fructose, glucose, high fructose corn syrup, or erythritol. A useful range for artificial sweeteners is in a concentration isosweet to about 2 to 15% sucrose. Different sweeteners may be used in combination in a concentration equivalent to at least 2% isointensity to sucrose. For example, carbonated beverages usually contain about 10% to 12% high fructose corn syrup and/or sucrose.

Identifying Sweetness Enhancers

Either chimeric taste receptors or taste receptors truncated to remove the extra-cellular domain are utilized in assays to identify candidate sweetness enhancers.

Assays Using Truncated Taste Receptors

T1R2 homomer binding assays are described in US 20050032158. Binding assays show binding only, as opposed to functional receptor activation, and are end-point-based and time consuming compared to faster functional assays that involve kinetic measurements. US 20050032158 further describes functional assays including cell-based assays for T1Rs, which are suitable for the known functional receptors T1R1/T1R3 and T1R2/T1R3.

The terms T1R2 "homomer" or "homomeric" polypeptide, protein, or receptor as used herein below are meant to encompass the monomer, dimer or oligomer of the T1R2 polypeptide or protein, as opposed to the heterodimeric T1R2/T1R3 receptor complex.

Applicant has found that a novel receptor protein, referred to as "T1R2-TMD," corresponding to a greatly truncated sequence of the T1R2 substituent of the T1R2/T1R3 heterodimer receptor complex, forms, surprisingly, a functional sweet receptor that binds to a sweet ligand and is able to activate G-proteins. The novel receptor protein T1R2-TMD was surprisingly found to be able not only to bind to ligands but also to activate downstream signaling in the absence of T1R3. According to methods provided herein, cells expressing both T1R2-TMD and a G-protein, but not T1R3 are contacted with test agents, optionally in combination with known or newly determined sweet tastants, to determine whether said agents can bind to and/or activate the T1R2 TMD domain. Agents that bind and/or activate the T1R2 domain are candidate sweeteners and candidate sweetness enhancers. Assays provided herein may therefore be used to identify a tested agent as a candidate sweet tastant or candidate enhancer of the sweet response.

The functional effects of the agent on the receptor and G-protein are determined by a suitable functional assay, for example, an assay that measures changes in parameters of the transduction pathways such as the concentration of intracellular $IP_3$ and $Ca^{2+}$, or by other G-protein specific assays such as labeling with GTPγS, according to techniques known in the art. Alternatively, binding assays may be used to determine ligand binding to T1R2-TMD.

In practicing the various aspects and embodiments described herein in relation to cloning, elucidating ligand-receptor pairs, and finding enhancers of the sweet response, recourse is made to conventional techniques in molecular biology, microbiology and recombinant DNA technology. These include the various known methods suitable for G-protein coupled receptors (GPCRs) including T1R2-TMD. Accordingly, the skilled person is fully apprised of such techniques and as such they are hereafter treated only summarily in order to more fully describe the context of the present invention.

Assays using Chimeric Receptors

Chimeric proteins are comprised of amino acid sequences derived from two or more different proteins. Chimeric proteins sometimes are able to combine desired properties or eliminate unwanted ones. The term CSR:T1R, as used herein below, designates the chimeric CSR:T1R2 homomer, the CSR:T1R3 homomer, the heterodimeric complex of CSR:T1R2 with CSR:T1R3 or with the wildtype T1R3 (CSR:T1R/CSR:T1R3 or CSR:T1R2/T1R3), or the heterodimeric complex of CSR:T1R3 with CSR:T1R2 or with the wildtype T1R2 (CSR:T1R2/CSR:T1R3 or T1R2/CSR:T1R3).

For the chimeric taste receptors, CSR:T1R chimeric proteins include, in particular, a CSR:T1R2 monomer, a CSR:T1R3 monomer, a CSR:T1R2/CSR:T1R3 heterodimer, a CSR:T1R2/T1R3 heterodimer (chimeric T1R2 subunit with wildtype T1R3), and a T1R2/CSR:T1R3 heterodimer (chimeric T1R3 subunit with wildtype T1R2). The CSR:T1R chimeric protein does not possess the VFT domains of T1R2, T1R3, or T1R2 and T1R3, and therefore allows identification specifically of compounds that bind to the TMD domains of T1R2 and/or T1R3. These identified compounds are of particular interest as they would not be expected to compete with carbohydrates binding in the VFT site for binding to the sweet taste receptor in vivo and are therefore particularly interesting candidate sweetness enhancers of carbohydrates.

Applicant has found that the chimeric monomers, CSR:T1R2 and CSR:T1R3, are functional and are able to form a functional CSR:T1R2/CSR:T1R3 heterodimer. Experiments of the applicant indicate that the CSR:T1R2 monomeric subunit also functions as a functional sweet receptor on its own, without forming a heterodimer. Preliminary experiments indicate that the CSR:T1R3 may have difficulties in engaging and/or activating certain G-proteins; however, CSR:T1R3 is useful in binding assays that do not require the ability to activate a G-Protein.

Accordingly, CSR:T1R and CSR:T1R3 are also useful in their monomeric form in the methods described herein. Alternative heterodimers that can be used in these methods are chimeric subunit/wildtype subunit heterodimers (CSR:T1R2/T1R3 and T1R2/CSR:T1R3). In the CSR:T1R2/CSR:T1R3 heterodimer, each of the CSR:T1R subunits of the heterodimeric complex consist of joined sequence fragments from two source proteins. The two source proteins are the human calcium-sensing receptor (hCaSR), and a T1R protein (T1R2 or T1R3). The hCaSR-derived fragment (CSR) common to both subunits comprises the extracellular domain (ECD) of hCaSR. The T1R-derived fragments comprise the transmembrane domains (TMD) of the T1R sequences and have two differing types, as they are derived from either T1R2 or T1R3.

The chimeric CSR:T1R constructs that are provided (DNA, vectors, transfected cells, proteins) are useful when screening, for example, for enhancers of the sweet taste response such as the candidate sweetness enhancers described herein. Traditional screening methods and binding assays may be used to screen for enhancers also. Such screening methodology is well-known in the art, and is outlined below.

Alternatively, an advantage of the CSR (the calcium-sensing receptor part of the hCaSR) in the chimeric CSR:T1R constructs is that the resulting receptors are responsive to calcium. Consequently, when screening for an enhancer in presence/absence of a ligand/agonist of the T1R receptor, the ligand can be replaced with a hCaSR-stimulating ligand instead of a sweet compound (for example, in the form of calcium chloride). This has the additional advantage of avoiding any negative effects of the actual ligand/agonist being present. For example, when screening for enhancers of sugar ligands/agonists, the adverse effects of sugars on osmolarity, etc is avoided. Extra-cellular domains from other Class C GPCRs that can also be considered potential partners for chimeric receptors, in addition to the calcium sensing receptors, include extra-cellular domains from metabotropic glutamate receptors (mGluRs), GPRC-type receptors (i.e GPRC5 and GPRC6a), V2R pheromone receptors, and GABA-B receptors. Similarly to using the hCaSR extra-cellular domain, using ligands for the other Class C GPCR's extra-cellular domains potentially allows the use of alternative ligands to sugar in screens for sweetness enhancers.

Cells Used in Assays Involving Truncated Taste Receptors

For the truncated taste receptors, useful cells in screens or assays according to the invention are cells that contain no T1R3. Transfected or endogenous T1R3 can negatively interfere with methods that determine agonist responses of T1R2-TMD or the change of said responses dependent on another enhancer. The absence of T1R3 provides a null background for the determination of T1R2-TMD activation, so that observed signals can be directly attributed to T1R2-TMD activity. This allows the identification of agents that specifically modulate T1R2-TMD, and excludes agents that activate T1R3 which could also include umami tastants, as T1R3 is part of both the sweet and the umami heterodimers.

Suitable eucaryotic cells include eucaryotic cells that do not contain T1R3, for example, without limitation, mammalian cells, yeast cells, or insect cells (including Sf9), amphibian cells (including melanophore cells), or worm cells including cells of Caenorhabditis (including Caenorhabditis elegans). Suitable mammalian cells that do not contain T1R3, include, for example, without limitation, COS cells (including Cos-1 and Cos-7), CHO cells, HEK293 cells, HEK293T cells, HEK293 T-Rex™ cells, or other transfectable eucaryotic cell lines. Suitable bacterial cells that do not contain T1R3 include, without limitation, E. coli.

Cells used in the CSR:T1R2 and/or CSR:T1R3 Assays

Transfected or endogenous T1R3 and T1R can negatively interfere with methods that determine agonist responses of CSR:T1R and/or CSR:T1R3, respectively, or the change of said responses dependent on another enhancer. The absence of T1R3 and T1R2 provides a null background for the determination of CSR:T1R2 and/or CSR:T1R3 activation, so that observed signals can be directly attributed to CSR:T1R2 and/or CSR:T1R3 activity. This allows the identification of agents that specifically modulate CSR:T1R2 and/or CSR:T1R3, and excludes agents that activate the wildtype T1R2 and T1R3, which could in the case of T1R3 also include umami tastants, as T1R3 is part of both the sweet and the umami heterodimers.

The presence of the endogenous wildtype T1R2 and/or T1R3 will cause some background signals, which are undesirable. While cells with endogenous T1R2 and/or T1R3 can still be useful to obtain results with sufficiently low background, a better choice usually are cells that do not contain the endogenous T1R2 and T1R3 receptors. When using a CSR:T1R2/T1R3 chimeric protein, however, the cells may contain wildtype T1R3 without adverse effect on the background. Similarly, when using a T1R/CSR:T1R3 chimeric protein, the cells may contain wildtype T1R2 without adverse effects on the background.

The cells listed below are particularly useful as they do not contain endogenous/wildtype T1R3, or endogenous wildtype T1R2. However, alternative cells are also useful in the methods described herein.

Suitable eucaryotic cells include for example, without limitation, mammalian cells, yeast cells, or insect cells (including Sf9), amphibian cells (including melanophore cells), or worm cells including cells of Caenorhabditis (including Caenorhabditis elegans). Suitable mammalian cells include, for example, without limitation, COS cells (including Cos-1 and Cos-7), CHO cells, HEK293 cells, HEK293T cells, HEK293 T-Rex™ cells, or other transfectable eucaryotic cell lines. Suitable bacterial cells include, without limitation, E. coli.

Cells may be transfected with a GPCR and a G-protein (which links the receptor to a phospholipase C signal transduction pathway) transiently or stably, as is well known in the art. An excellent heterologous expression system that employs the chimeric G-protein G alpha 16-gustducin 44 which provides for enhanced coupling to taste GPCRs, is described in detail in WO 2004/055048 (also known as G.sub..alpha.16 gust(ducin)44, G.sub.alpha.16gust(ducin) 44, Gα16gust(ducin)44, Ga16gust(ducin)44, Gα16-gustducin 44, or as used herein-below, "Gα16gust44"). Alternatively, other chimeric G-proteins based on Gaq-Gustducin described in WO 2004/055048, or other G-Proteins, for example, G16 or G15, may also be used.

The CSR:T1R can be expressed in a cell with a G-protein that links the receptor to a signal transduction pathway, for example, the phospholipase C signal transduction pathway, or signal transduction pathways including, for example, the following: adenylate cyclase, guanylate cyclase, phospholipase C, $IP_3$, GTPase/GTP binding, arachinoid acid, cAMP/cGMP, DAG, protein kinase c (PKC), MAP kinase tyrosine kinase, or ERK kinase. Alternatively, any suitable reporter gene may be linked to a CSR:T1R-activation responsive promoter and used to determine CSR:T1R activity, as described in more detail below.

Vector Constructs Used in Cells Described Above

The vector constructs for expressing T1R2-TMD or CSR:T1R and/or the G-protein in such cells may be produced, for example, by known techniques or methods that use polymerase chain reaction ("PCR"). After verification of the sequence, cDNA fragments may be sub-cloned into a suitable vector, for example pcDNA 3.1 mammalian expression vector for mammalian cells, and transiently transfected in a corresponding host cell to enable the correct expression of the gene(s).

After a post-transfection period, for example 48 hours, cell lysates may be prepared and analyzed by Western blot in order to confirm the correct expression of the protein. Once correct protein expression is confirmed, suitable cells, for example mammalian cells including HEK293T cells and HEK T-Rex™, may be transfected to generate cells stably expressing the protein according to techniques well known in the art.

Alternatively, a variety of non-mammalian expression vector/host systems can be used to contain and express sequences encoding the T1R2-TMD or CSR:T1R G-Protein coupled receptor (GPCR). These include, for example, microorganisms including bacteria transformed with recombinant bacteriophage, plasmid, or cosmid DNA expression vectors; yeast transformed with yeast expression vectors; insect cell systems infected with viral expression vectors (for example baculovirus), or with bacterial expression vectors (for example pBR322 plasmids). Examples of specific vectors that may be used with the systems described herein-above are described in *G-protein coupled receptors*, Signal Transduction Series, edited by Tatsuya Haga and Gabriel Berstein, 1st ed., CRC Press—Boca Raton Fla.; September 1999.

In bacterial systems, a number of cloning and expression vectors may be selected depending upon the use intended for polynucleotide sequences encoding T1R2-TMD or CSR:T1R. For example, routine cloning, subcloning, and propagation of polynucleotide sequences encoding a GPCR can be achieved using a multifunctional *E. coli* vector such as pBLUESCRIPT (Stratagene, La Jolla Calif.) or pSPORT1 plasmid (Life Technologies). Ligation of sequences encoding a GPCR into the vector's multiple cloning sites disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. When large quantities of a GPCR are needed, for example, for the production of antibodies, vectors which direct high level expression of a GPCR may be used. For example, vectors containing the strong, inducible SP6 or T7 bacteriophage promoter may be used.

Yeast expression systems may be used for production of a GPCR. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation.

To express heterologous proteins in insect cell lines, derivatives of the *Lepidopteran baculovirus* or the *Autographa californica* multicapsid nucleo-virus (AcM-NPV) can be used, for example. In this system, foreign gene expression is directed by a very strong late viral promoter, either the polyhedrin or p10 promoters, and a wide array of vectors is available that optimises expression and recovery of recombinant proteins. These vectors enable expression of both membrane-bound and secreted proteins at high levels, and also many post-translational modifications known to occur in mammalian systems, including N- and O-linked glycosylation, phosphorylation, acylation, proteolysis and secreted vaccine components. A number of vectors are commercially available, for example the InsectSelect™ System from Invitrogen.

Expression Systems

In order to express cDNAs encoding the desired proteins (e.g., G-protein and either CSR:T1R or T1R2-TMD), one typically subclones the appropriate cDNA into an expression vector that contains a strong promoter to direct transcription, a transcription/translation terminator, and a ribosome-binding site for translational initiation. Suitable bacterial promoters are well known in the art, for example, *E. coli, Bacillus* sp., and *Salmonella*, and kits for such expression systems are commercially available. Similarly, eukaryotic expression systems for mammalian cells, yeast, and insect cells are commercially available. The eukaryotic expression vector may be, for example, an adenoviral vector, an adeno-associated vector, or a retroviral vector.

In addition to the promoter, the expression vector typically contains a transcription unit or expression cassette that contains all the additional elements required for the expression of the protein-encoding nucleic acid in host cells. A typical expression cassette thus contains a promoter operably linked to the nucleic acid sequence encoding the protein and signals required for efficient polyadenylation of the transcript, ribosome binding sites, and translation termination. The nucleic acid sequence encoding the protein may typically be linked to a membrane-targeting signal such as the N-terminal 45 amino acids of the rat somatostatin-3 receptor sequence to promote efficient cell-surface expression of the recombinant protein, which is useful for cell-surface receptors. Additional vector elements may include, for example, enhancers. An expression cassette should also contain a transcription termination region downstream of the structural gene to provide for efficient termination. The termination region may be obtained from the same gene as the promoter sequence or may be obtained from different genes.

For expression of the proteins, conventional vectors for expression in eucaryotic or procaryotic cells well known in the art may be used. Examples of vectors include bacterial expression vectors, for example, plasmids including pBR322-based plasmids, pSKF, and pET23D, and fusion expression systems, for example, GST and LacZ.

Expression vectors containing regulatory elements from eukaryotic viruses are typically used in eukaryotic expression vectors, for example SV40 vectors, cytomegalovirus vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, pcDNA3.1, pIRES and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells. Some expression systems have markers that provide gene amplification such as thymidine kinase, hygromycin B phosphotransferase, dihydrofolate reductase and the like.

The elements that are typically included in expression vectors may also include a replicon that functions in *E. coli*, a gene encoding drug resistance to permit selection of bacteria that harbor recombinant plasmids, and unique restriction sites in non-essential regions of the plasmid to allow insertion of eukaryotic sequences. The particular drug resistance gene chosen is not critical. Any of the many drug resistance genes known in the art are suitable. The prokaryotic sequences are optionally chosen such that they do not interfere with the replication of the DNA in eukaryotic cells, for vectors that will be used in both prokaryotic and eukaryotic cells.

In bacterial systems a T1R2-TMD or CSR:T1R cDNA fragment may be expressed alone or as a fusion protein wherein the T1R2-TMD or CSR:T1R of interest is fused to the *E. coli* periplasmic maltose-binding protein (MBP) wherein the MBP, including its signal peptide, is linked to the amino terminus of the T1R2-TMD or CSR:T1R. The T1R2-TMD or CSR:T1R cDNA or the MBP fusion with T1R2-TMD or CSR:T1R protein cDNA is subcloned into a suitable plasmid, for example pBR322, wherein *E. coli* GPCR expression is driven by the lac wild-type promoter. Methods of expression of GPCRs in *E. coli* are described, for example, in *G-protein coupled receptors*, Signal Transduction Series, edited by Tatsuya Haga and Gabriel Berstein, 1st ed., CRC Press—Boca Raton Fla.; September 1999

Genetically engineered yeast systems and insect cell systems which lack endogenous GPCRs provide the advantage of a null background for CSR:T1R activation screening or for T1R2-TMD activation screening. Genetically engineered yeast systems substitute a human GPCR and Gα protein for the corresponding components of the endogenous yeast pheromone receptor pathway. Downstream signalling pathways are also modified so that the normal yeast response to the signal is converted to positive growth on selective media or to reporter gene expression (described by Broach, J. R. and J. Thomer, 1996, *Nature,* 384 (supp.):14-16). Genetically engineered insect systems incorporate a human GPCR and Gα protein that enables receptor coupling to the phospholipase C signalling pathway (see, for example, Knight and Grigliatti, 2004, *J. Receptors and Signal Transduction,* 24: 241-256). Amphibian cell systems, in particular melanophore cells, are described, for example, in WO 92/01810, which describes a GPCR expression system.

Overexpression of T1R2-TMD or CSR:T1R

T1R2-TMD or CSR:T1R may be overexpressed by placement under the control of a strong constitutive promoter, for example the CMV early promoter. Alternatively, certain mutations of conserved GPCR amino acids or amino acid domains can be introduced to render the employed GPCR constitutively active.

Inducible promoters may also be used to direct, control, and regulate expression of T1R2-TMD or CSR:T1R. For example, without limitation, the T-Rex™ expression system (Invitrogen Corp., Carlsbad, Calif.) may be used. The T-Rex™ System is a tetracycline-regulated mammalian expression system that uses regulatory elements from the *E. coli* Tn10-encoded tetracycline (Tet) resistance operon. Tetracycline regulation in the T-Rex™ System is based on the binding of tetracycline to the Tet repressor and de-repression of the promoter controlling expression of the gene of interest.

Transfection of T1R2-TMD or CSR:T1R Expression Vector Constructs into Cells

Standard transfection methods can be used to produce bacterial, mammalian, yeast or insect cell lines that express large quantities of the protein of interest, such as T1R2-TMD or CSR:T1R. Any known method for introducing nucleotide sequences into host cells may be used. It is only necessary that the particular genetic engineering procedure used be capable of successfully introducing the relevant genes into the host cell capable of expressing the proteins of interest. These methods may involve introducing cloned genomic DNA, cDNA, synthetic DNA or other foreign genetic material into a host cell and include the use of calcium phosphate transfection, polybrene, protoplast fusion, electroporation, liposomes, microinjection, plasma vectors, viral vectors and the like.

Cell Culture

After transfection, the transfected cells may be cultured using standard culturing conditions well known in the art. It will be apparent to the skilled person that different cells require different culture conditions including appropriate temperature and cell culture media.

T1R2-TMD or CSR:T1R Receptor Protein Recovery

If desired, the protein may be recovered from the cell culture using standard techniques. For example, the cells may be burst open either mechanically or by osmotic shock before being subject to precipitation and chromatography steps, the nature and sequence of which will depend on the particular recombinant material to be recovered. Alternatively, the recombinant protein may be recovered from the culture medium in which the recombinant cells had been cultured.

Taste Modulators that May be Identified by the Assays Herein

Modulators (various types including ligands, agonists, partial agonists, antagonists, inverse agonists, inhibitors, enhancers) of T1R receptor activity can be identified by the assays described herein. The type of modulator may include more than one type at a time, and may depend on the concentration. For example, an agent may act as an agonist in a certain concentration range, but act as an enhancer of another agonist (for example a sweetener or sugar) in another concentration range. Therefore, agents should be tested at different concentrations to determine their modulator activity. There now follows a definition of the agents that can be identified in the methods described herein.

An enhancer is an agent that causes an increase in one or more of the following: the cell surface expression of a receptor, the binding of a ligand to a receptor, ligand-induced receptor activity, or the intracellular response initiated by an active form of the receptor (either in the presence or absence or an agonist). An inhibitor is an agent that causes a decrease in one or more of the following: the cell surface expression of a receptor, the binding of a ligand to a receptor, ligand-induced receptor activity, or the intracellular response initiated by an active form of the receptor (either in the presence or absence or an agonist). The enhancer can itself be an agonist that binds to the receptor, activates it and thereby modulates an increase in the cellular response.

Enhancers include various types of compounds, including small molecules, peptides, proteins, nucleic acids, antibodies or fragments thereof. These can be derived from various sources including synthetic or natural, extracts of natural material, for example from animal, mammalian, insect, plant, bacterial or fungal cell material or cultured cells, or conditioned medium of such cells.

A ligand is an agent that binds to the receptor; it may be an agonist, partial agonist, enhancer, inhibitor, antagonist, or inverse agonist. An agonist is a ligand of the T1R receptor that activates the receptor and increases an intracellular response when it binds to a receptor compared to the intracellular response in the absence of the agonist. Additionally or alternatively, an agonist may decrease internalization of a cell surface receptor such that the cell surface expression of a receptor is increased as compared to the number of cell surface receptors present on the surface of a cell in the absence of an agonist. Agonists of T1R include, for example, calcium, p-ethoxybenzaldehyde, perillartine, cyclamate, NDHC, and cinnamonitrile. Ligands of the CSR:T1R chimeric protein comprise CSR-domain-ligands (e.g. calcium) and TAS1R-domain ligands (e.g. candidate sweetness enhancers that bind to the T1R2 or T1R3 transmembrane domains).

A partial agonist is an agonist that only partially activates the receptor in comparison to other agonists that maximally activate the receptor. An antagonist is a ligand which binds to the receptor at the same (competitive antagonist) or at a different site (alllosteric antagonist) as an agonist, but does not activate an intracellular response initiated by an active form of a receptor, thereby inhibiting the intracellular response induced by an agonist as compared to the intracellular response in the presence of an agonist and in the absence of an antagonist. An inverse agonist, binding to a receptor, decreases the constitutive intracellular response mediated by a receptor as compared to the intracellular response in the absence of the inverse agonist. An inhibitor decreases the binding of an agonist to the receptor as compared to the binding of the agonist in the absence of inhibitor, and/or decreases the intracellular response induced by an agonist.

The activity or changes in activity, of a receptor binding a ligand and transmitting the signal through, for example, a G-protein (i.e. due to different interactions with enhancers) can be determined by the assays described herein-below.

Assays to Identify Enhancers of the T1R2-TMD or CSR:T1R Receptor

Enhancers can be identified using a wide variety of in vitro and in vivo assays to determine and compare functional effects/parameters, or alternatively by binding assays. The effects of the test agents upon the function of the receptors can be measured by examining suitable functional parameters.

Any physiological change that is affected by receptor activity can be used to identify enhancers.

Such functional assays are well-known in the art, for example, assays that use intact cells or tissues isolated from animals and that are based on measuring the concentration, activity, or change thereof of a secondary messenger (including, for example, intracellular calcium (Ca2+), cAMP, cGMP, inositol phospate ($IP_3$), diacylglycerol/DAG, arachinoid acid, MAP kinase or tyrosine kinase), ion flux, phosphorylation levels, transcription levels, neurotransmitter levels, and assays based on GTP-binding, GTPase, adenylate cyclase, phospholipid-breakdown, diacylglycerol, inositol triphosphate, arachidonic acid release, PKC, kinase and transcriptional reporters. Some suitable assays are, for example, described in WO 01/18050.

Receptor activation typically initiates subsequent intracellular events, for example, increases in second messengers, for example, IP3, which releases intracellular stores of calcium ions. Activation of some G-protein coupled receptors stimulates the formation of inositol triphosphate (IP3) through phospholipase C-mediated hydrolysis of phosphatidylinositol. $IP_3$ in turn stimulates the release of intracellular calcium ion stores. Thus, a change in cytoplasmic calcium ion levels, or a change in second messenger levels such as $IP_3$ can be used to determine G-protein coupled receptor activity. All functional assays may be performed with, for example, samples containing cells expressing the receptor on their surfaces or on isolated cell membrane fractions. Useful cells are described herein-above. Also, for example, tissues from transgenic animals may be used.

To identify an enhancer which is not an agonist itself (e.g. instead it is an antagonist, partial agonist, inverse agonist, inhibitor, or enhancer), samples with and without test agent both containing an agonist are compared. As agonist, for example, calcium can be used if the receptor is CSR:T1R. Using calcium has the advantage that both TMDs will be accessible. Other known or identified agonists can also be used, for example, perillartine, p-ethoxybenzaldehyde, cyclamate, neohesperidine dihydrochalone (NDHC), and cinnamonitrile. However, these will partially occupy ligand/agonist binding sites which may coincide with the enhancer binding site of the putative enhancer, and may cause lower signals. For example, a control (with agonist but without enhancer) is assigned a relative receptor activity value of 100. A decrease in activity relative to the control identifies an inhibitor, antagonist or inverse agonist, whereas an increase identifies an enhancer. An increase or decrease in the measured activity of, for example, 10% or more (or any statistically significant difference) can be considered significant in a sample with test agent compared to a sample without test agent; or in a sample with test agent compared to a control sample with test agent but in which the cells do not express T1R2-TMD or CSR:T1R (mock-transfected cells).

Identification of Agonists or Partial Agonists

To identify an agonist or partial agonist that does not bind in the VFT domains, a sample with test agent is compared to a positive control with an agonist (for example calcium chloride (if the receptor is CSR:T1R), perillartine, cyclamate, neohesperidin dihydrochalcone (NDHC), cinnamonitrile, or another identified ligand/agonist). Alternatively/additionally, samples with and without test agent are compared in their activity with the T1R2-TMD or CSR:T1R chimeric protein. For example, an agonist or partial agonist will have a biological activity corresponding to at least 10% of the maximal biological activity of the positive control sweet agonist when the agonist or partial agonist is present at 100 mM or less, for example it may have a maximal biological activity comparable to the agonist's or higher. Maximal biological activity is defined as the maximal achievable receptor response to an agonist, for example calcium chloride, perillartine, p-ethoxybenzaldehyde, cyclamate, neohesperidin dihydrochalcone (NDHC), cinnamonitrile that can be achieved within a given receptor assay format and this response fails to increase further despite application of increasing concentrations of that same agonist.

The above-mentioned agonists may, at a different concentration, also act as enhancers of an agonist of the T1R2-TMD or CSR:T1R chimeric protein. This may be tested in a screening method by using calcium or other agonist to test the agonist-test agent for signals indicating a sweetness enhancing effect. Alternatively, an increase in the measured activity of, for example, 10% or more in a sample with test agent is compared to a sample without test agent or is compared to a sample with test agent but based on cells that do not express T1R2-TMD or CSR:T1R (mock-transfected cells). To identify antagonists, receptor activity in the presence of a known agonist with and without a test agent is compared. Antagonists show a reduction of agonist-stimulated receptor activity, for example by at least 10%. To identify inverse agonists, receptor activity with and without a test agent is compared in samples comprising animals/cells/membranes that overexpress the receptor as described herein-above. Inverse agonists show a reduction of constitutive activity of the receptor, for example by at least 10%.

Many screens rely on calcium activity, and for these a buffer system low in calcium should be used to avoid unspecific stimulation of cells, receptor, enzyme or reporter genes. To detect changes in cytoplasmic ion concentration or membrane voltage, cells can be loaded with ion sensitive dyes to report receptor activity, as described in detail in *G-protein coupled receptors*, Signal Transduction Series, edited by Tatsuya Haga and Gabriel Berstein, 1st ed., CRC Press—Boca Raton Fla.; September 1999. Changes in the concentration of ions in the cytoplasm or membrane voltage are measured using an ion sensitive or membrane voltage fluorescent indicator, respectively. Various examples of suitable detection methods that measure T1R2-TMD or CSR:T1R receptor activity in assays described above follow.

Calcium Flux Assay

Intracellular calcium release induced by the activation of GPCRs is detected using cell-permanent dyes that bind to calcium. The calcium-bound dyes generate a fluorescence signal that is proportional to the rise in intracellular calcium. The method allows for rapid and quantitative measurement of receptor activity.

Cells used are transfected cells that co-express the T1R2-TMD or CSR:T1R GPCRs and a G-protein which allows for coupling to the phospholipase C pathway as described above. Negative controls include cells or their membranes not expressing T1R2-TMD or CSR:T1R (mock transfected), to exclude possible non-specific effects of the candidate compound. The calcium flux detection protocol is described in detail in *G-protein coupled receptors*, Signal Transduction Series, edited by Tatsuya Haga and Gabriel Berstein, 1st ed., CRC Press—Boca Raton Fla.; September 1999, and an adapted version is summarized below:

Day 0: 96-well plates are seeded with 8500 cells per well and maintained at 37° C. overnight in nutritive growth media.

Day 1: Cells are transfected using 150 ng of GPCR DNA and 0.3 μl of Lipofectamine 2000 (Invitrogen) per well. Transfected cells are maintained at 37° C. overnight in nutritive growth media.

Day 2: Growth media is discarded and cells are incubated for 1 hour (at room temperature in the dark) with 50 μl of calcium assay solution consisting of 1.5 µM Fluo-4 AM (Molecular Probes) and 2.5 µM probenicid dissolved in a reduced calcium C1 buffer solution (see example 1 below for standard C1 buffer formulation) which contains 130 mM NaCl, 5 mM KCl, 10 mM Hepes, 0.5 mM $CaCl_2$ and 10 mM glucose (pH 7.4) at 37° C. 125 µl of the reduced calcium C1 buffer is added to each well and the plate is further incubated for 30 minutes at room temperature in the dark. Buffer solutions are discarded and plate is washed 5 times with 100 µl reduced calcium C1 buffer as a washing buffer and cells are reconstituted in 200 µl of reduced calcium C1 buffer. Then the plate is placed in a fluorescence microplate reader, for example, the Flexstation (Molecular Devices) or the FLIPR (Fluorescent Imaging Plate Reader) (Molecular Devices) and receptor activation is initiated following addition of 20 µl of a 10× concentrated ligand stock solution. Fluorescence is continuously monitored for 15 seconds prior to ligand addition and for 45-110 seconds after ligand addition. Receptor activation levels are defined by the two following equations: % Activation=((Maximum fluorescence−baseline fluorescence)/baseline fluorescence)*100, or Fluorescence Increase=Maximum Fluorescence−baseline fluorescence, where baseline fluorescence represents the average fluorescence levels prior to ligand addition. Alternatively, receptor activation can be determined by the increase in peak fluorescence (F) normalized to the baseline fluorescence ($F_0$). The data are normalized using the following equation: $\Delta F/F=(F-F_0)/F_0$, where F is the peak fluorescence signal and $F_0$ is the baseline fluorescence signal, wherein the baseline fluorescence represents the mean fluorescence calculated for the first 10 to 15 seconds prior to ligand addition.

Useful cells are, without limitation, mammalian cells as described herein-above, for example HE 93T cells and BEK293 T-Rex™ cells. Cells may be transfected with a GPCR and a G-Protein transiently or stably as is well known in the art. An excellent heterologous expression system is described in detail in WO 2004/055048. A calcium flux assay can be performed, for example, as described in example 1 herein-below. The identification of an enhancer is performed as described above subject to the following modifications. The signals are compared to the baseline level of T1R2-TMD or CSR:T1R activity obtained from recombinant cells expressing T1R2-TMD or CSR:T1R in the presence of an agonist but in the absence of a test agent. An increase or decrease in T1R2-TMD or CSR:T1R activity, for example any statistically significant increase in activity, such as, without limitation, by 10%, 20%, 50%, or 100% or more identifies an enhancer. Alternatively, the identification involves a statistically significant increase or decrease in fluorescence intensity of, for example, without limitation, 10% or more, when compared to a sample without enhancer, or when compared to a sample with enhancer but in cells that do not express the T1R2-TMD or CSR:T1R polypeptide (mock-transfected cells).

Adenylate Cyclase Activity

Assays for adenylate cyclase activity are performed, for example, as described in detail by Kenimer & Nirenberg, 1981, *Mol. Pharmacol.* 20: 585-591. Reaction mixtures are incubated usually at 37° C. for less than 10 minutes. Following incubation, reaction mixtures are deproteinized by the addition of 0.9 ml of cold 6% trichloroacetic acid. Tubes are centrifuged and each supernatant solution is added to a Dowex AG50W-X4 column. The cAMP fraction from the column is eluted with 4 ml of 0.1 mM imidazole-HCl (pH 7.5) into a counting vial in order to measure the levels of cAMP generated following receptor activation by the agonist. Control reactions should also be performed using protein homogenate from cells that do not express a T1R2-TMD or CSR: T1R polypeptide.

$IP_3/Ca^{2+}$ Signals

In cells expressing G-proteins, signals corresponding to inositol triphosphate ($IP_3$)/$Ca^{2+}$ and thereby receptor activity can be detected using fluorescence. Cells expressing a GPCR may exhibit increased cytoplasmic calcium levels as a result of contribution from both intracellular stores and via activation of ion channels, in which case it may be desirable, although not necessary, to conduct such assays in calcium-free buffer, optionally supplemented with a chelating agent such as EDTA, to distinguish fluorescence response resulting from calcium release from internal stores (see *G-protein coupled receptors*, Signal Transduction Series, edited by Tatsuya Haga and Gabriel Berstein, 1st ed., CRC Press—Boca Raton Fla.; September 1999).

Phospholipase C/Intracellular $Ca^{2+}$ Signals

T1R2-TMD or CSR:T1R is expressed in a cell with a G-protein that links the receptor to a phospholipase C signal transduction pathway. Changes in intracellular $Ca^{2+}$ concentration are measured, for example using fluorescent $Ca^{2+}$ indicator dyes and/or fluorometric imaging (see *G-protein coupled receptors*, Signal Transduction Series, edited by Tatsuya Haga and Gabriel Berstein, 1st ed., CRC Press—Boca Raton Fla.; September 1999).

GTPase/GTP Binding

For a GPCR including T1R2-TMD or CSR:T1R, a measure of receptor activity is the binding of GTP by cell membranes containing T1R2-TMD or CSR:T1R. The method measures the G-protein coupling to membranes by detecting the binding of labeled GTP. Membranes isolated from cells expressing the receptor are incubated in a buffer containing 35S-GTPγS and unlabelled GDP. Active GTPase releases the label as inorganic phosphate, which is detected by separation of free inorganic phosphate in a 5% suspension of activated charcoal in 20 mM $H_3PO_4$, followed by scintillation counting. The mixture is incubated and unbound labeled GTP is removed by filtration onto GF/B filters. Bound and labeled GTP is measured by liquid scintillation counting. Controls include assays using membranes isolated from cells not expressing T1R2-TMD or CSR:T1R (mock-transfected), in order to exclude possible non-specific effects of the test agent. The method is described in detail by Traynor and Nahorsi, 1995, *Mol. Pharmacol.,* 47: 848-854.

To identify enhancers or inhibitors, as described herein-above, a statistically significant change (increase or decrease) of, for example, 10% or more in GTP binding or GTPase activity is usually sufficient. However, to identify agonists, the assays described herein-above are performed subject to the following modifications. An agent is identified as an agonist usually if the activity is at least 50% of that of a known agonist (for example perillartine) when the compound is present at 100 mM or less, such as within a range of 10 µM to 500 µM, for example about 100 µM, or if it will induce a level the same as or higher than that induced by a known agonist.

Microphysiometer or Biosensor

Such assays can be performed as described in detail in Hafner, 2000, *Biosens. Bioelectron.* 15: 149-158.

Arachinoid Acid

The intracellular level of arachinoid acid is employed as an indicator of receptor activity. Such a method is described in detail by Gijon et al., 2000, *J. Biol. Chem.,* 275:20146-20156.

cAMP/cGMP

Intracellular or extracellular cAMP can be measured using a cAMP radioimmunoassay (RIA) or cAMP binding protein, for example as described by Horton & Baxendale, 1995,

*Methods Mol. Biol.* 41: 91-105. A number of kits for the measurement of cAMP also are commercially available, for example the High Efficiency Fluorescence Polarization-based homogeneous assay by LJL Biosystems and NEN Life Science Products. Alternatively, the intracellular or extracellular levels of cGMP also can be measured, for example, using an immunoassay. For example, the method described in Felley-Bosco et al., *Am. J. Resp. Cell and Mol. Biol.,* 11: 159-164 (1994), may be used to determine the level of cGMP. Alternatively an assay kit for measuring cAMP and/or cGMP as described in U.S. Pat. No. 4,115,538 can be used. Negative controls with mock-transfected cells or extracts thereof to exclude possible non-specific effects of test agents may be used.

DAG/IP$_3$

Second messengers diacylglycerol (DAG) and/or inositol triphosphate (IP$_3$), which are released by phospholipid breakdown, caused by receptor activity, can be detected and used as an indicator of GPCR (T1R2-TMD or CSR:T1R) activity, for example as described in *Phospholipid Signaling Protocols*, edited by Ian M. Bird, Totowa, N.J., Humana Press, 1998. Kits for the measurement of inositol triphosphates, available commercially from e.g. Perkin Elmer and CisBio International also can be used. Negative controls with mock-transfected cells or extracts thereof to exclude possible non-specific effects of test agents may be used.

PKC Activity

Growth factor receptor tyrosine kinases can signal via a pathway involving activation of protein kinase C (PKC), which is a family of phospholipid- and calcium-activated protein kinases. Increases in gene products induced by PKC show PKC activation and thereby receptor activity. These gene products include, for example, proto-oncogene transcription factor-encoding genes (including c-fos, c-myc and c-jun), proteases, protease inhibitors (including collagenase type I and plasminogen activator inhibitor), and adhesion molecules (including intracellular adhesion molecule I (ICAM I)). PKC activity may be directly measured as described by Kikkawa et al., 1982, J. Biol. Chem., 257: 13341, where the phosphorylation of a PKC substrate peptide, which is subsequently separated by binding to phosphocellulose paper, is measured. It can be used to measure activity of purified kinase, or in crude cellular extracts. Protein kinase C sample can be diluted in 20 mM HEPES/2 mM DTT immediately prior to the assay. An alternative assay can be performed using the Protein Kinase C Assay Kit commercially available by PanVera.

The above-described PKC assays are performed on extracts from cells expressing T1R2-TMD or CSR:T1R. Activity also can be measured through the use of reporter gene constructs driven by the control sequences of genes activated by PKC activation. Negative controls with mock-transfected cells or extracts thereof to exclude possible non-specific effects of test agents may be used.

MAP Kinase Activity

MAP kinase activity can be measured using commercially available kits such as, for example, the p38 MAP Kinase assay kit by New England Biolabs, or the FlashPlate™ MAP Kinase assays by Perkin-Elmer Life Sciences. p42/44 MAP kinases or ERK1/2 can be measured to show GPCR (CSR: T1R) activity when cells expressing Gq and Gi coupled GPCRs are used, and an ERK1/2 assay kit is commercially available from TGR Biosciences, which measures the phosphorylation of endogenous ERK1/2 kinases following GPCR activation. Direct measurements of tyrosine kinase activity through known synthetic or natural tyrosine kinase substrates and labeled phosphate are well known and also can be used; the activity of other types of kinases (for example, serine/threonine kinases) can be measured similarly.

All kinase assays can be performed with either purified kinases or crude extracts prepared from cells expressing one or more T1R2-TMD or CSR:T1R polypeptide. The substrates of kinases that are used can be either full-length protein or synthetic peptides representing the substrate. Pinna & Ruzzene (1996, *Biochem. Biophys. Acta* 1314: 191-225) lists a number of phosphorylation substrate sites useful for detecting kinase activities. A number of kinase substrate peptides are commercially available. One that is particularly useful is the "Src-related peptide," RRLIEDAEYAARG (commercially available from Sigma), which is a substrate for many receptor and nonreceptor tyrosine kinases. Some methods require the binding of peptide substrates to filters, then the peptide substrates should have a net positive charge to facilitate binding. Generally, peptide substrates should have at least 2 basic residues and a free-amino terminus. Reactions generally use a peptide concentration of 0.7-1.5 mM. Negative controls with mock-transfected cells or extracts thereof to exclude possible non-specific effects of test agents may be used.

Transcriptional Reporters/T1R-TMD or CSR:T1R-Responsive Promoter/Reporter Gene Assays To identify enhancers with reporter gene assays, a 100% increase, for example, in reporter gene expression is significant. An agonist stimulates for example 100, 500, or 1000% higher reporter gene expression in the presence of the test agent than in the absence of the test agent. The intracellular signal initiated by binding of an agonist to T1R2-TMD or CSR:T1R sets in motion a cascade of intracellular events, the ultimate consequence of which is a rapid and detectable change in the transcription or translation of one or more genes. The activity of the receptor can therefore be determined by measuring the expression of a reporter gene driven by a promoter responsive to T1R2-TMD or CSR:T1R activation.

A "promoter" as used herein is one or more transcriptional control elements or sequences necessary for receptor-mediated regulation of gene expression, including one or more of basal promoter, enhancers and transcription-factor binding sites necessary for receptor-regulated expression. Promoters responsive to the intracellular signals resulting from agonist binding to T1R2-TMD or CSR:T1R are selected and operatively linked to a corresponding promoter-controlled reporter gene whose expression or gene product activity is readily detectable and measurable.

Reporter genes may be selected, for example, from luciferase, CAT, GFP, β-lactamase, β-galactosidase, and the so-called "immediate early" genes, c-fos proto-oncogene, transcription factor CREB, vasoactive intestinal peptide (VIP) gene, the somatostatin gene, the proenkephalin gene, the phosphoenolpyruvate carboxy-kinase (PEPCK) gene, genes responsive to NF-κB, and AP-1-responsive genes (including the genes for Fos and Jun, Fos-related antigens (Fra) 1 and 2, IκBα, ornithine decarboxylase, and annexins I and II). Promoters will be selected according to the selected reporter gene, as will be apparent to the skilled person. Luciferase, CAT, GFP, β-lactamase, β-galactosidase and assays for the detection of their products are well known in the art. Examples of further reporter genes are described herein-below.

The "immediate early" genes are suitable and are rapidly induced (for example within minutes of contact between the receptor and the effector protein or ligand). Preferable properties in reporter genes include one or more of the following: rapid responsiveness to ligand binding, low or undetectable expression in quiescent cells; induction that is transient and independent of new protein synthesis; subsequent shut-off of transcription requires new protein synthesis; and mRNAs transcribed from these genes which have a short half-life of several minutes to a few hours. Similarly, the promoter preferably has one, several or all of these properties.

The c-fos proto-oncogene is an example of a gene that is responsive to a number of different stimuli and has a rapid induction. The c-fos regulatory elements include a TATA box that is required for transcription initiation; two upstream elements for basal transcription, and an enhancer, which includes an element with dyad symmetry and which is required for induction by TPA, serum, EGF, and PMA. The 20 bp c-fos transcriptional enhancer element located between −317 and −298 bp upstream from the c-fos mRNA cap site, is essential for serum induction in serum starved NIH 3T3 cells. One of the two upstream elements is located at −63 to −57 and it resembles the consensus sequence for cAMP regulation.

The transcription factor CREB (cyclic AMP responsive element binding protein) is responsive to levels of intracellular cAMP. Therefore, the activation of a receptor that signals via modulation of cAMP levels can be determined by detecting either the binding of the transcription factor, or the expression of a reporter gene linked to a CREB-binding element (termed the CRE, or cAMP response element). The DNA sequence of the CRE is TGACGTCA. Reporter constructs responsive to CREB binding activity are described in U.S. Pat. No. 5,919,649.

Other suitable reporter genes and their promoters include the vasoactive intestinal peptide (VIP) gene and its promoter which is cAMP responsive; the somatostatin gene and its promoter which is cAMP responsive; the proenkephalin and its promoter which is responsive to cAMP, nicotinic agonists, and phorbol esters; and the phosphoenolpyruvate carboxykinase (PEPCK) gene and its promoter which is cAMP responsive. Additional examples of reporter genes and their promoters that are responsive to changes in GPCR activity include the AP-1 transcription factor and NF-κB. The AP-1 promoter is characterized by a consensus AP-1 binding site which is the palindrome TGA(C/G)TCA. The AP-1 site is also responsible for mediating induction by tumor promoters including the phorbol ester 12-O-tetradecanoylphorbol-β-acetate (TPA), and is therefore sometimes also referred to as a TRE, for TPA-response element. AP-1 activates numerous genes that are involved in the early response of cells to growth stimuli. Examples of AP-1-responsive genes include the genes for Fos and Jun (which proteins themselves make up AP-1 activity), Fos-related antigens (Fra) 1 and 2, IκBα, ornithine decarboxylase, and annexins I and II.

The NF-κB promoter/binding element has the consensus sequence GGGGACTTTCC (SEQ ID NO: 29). A large number of genes have been identified as NF-κB responsive, and their control elements can be linked to a reporter gene to monitor GPCR activity. Genes responsive to NF-κB include for example those encoding IL-1β, TNF-α, CCR5, P-selection, Fas ligand, GM-CSF and IκB α. Vectors encoding NF-κB-responsive reporters are known in the art or can be readily formed using ordinary skill in the art, for example, synthetic NF-κB elements and a minimal promoter, or using the NF-κB-responsive sequences of a gene known to be subject to NF-κB regulation. Further, NF-κB responsive reporter constructs are commercially available from, for example, CLONTECH.

A given promoter construct can easily be tested by exposing GPCR (T1R2-TMD or CSR:T1R)-expressing cells, transfected with the construct, to an agonist (for example perillartine). An increase of, for example, 100% in the expression of reporter gene in response to the agonist indicates that the reporter is suitable to measure GPCR (T1R2-TMD or CSR:T1R) activity. Controls for transcription assays include both cells not expressing GPCR (T1R2-TMD or CSR:T1R), but carrying the reporter construct, and cells with a promoterless reporter construct.

Agents that modulate GPCR (T1R2-TMD or CSR:T1R) activity as shown by reporter gene activation can be verified by using other promoters and/or other receptors to verify GPCR (T1R2-TMD or CSR:T1R) specificity of the signal and determine the spectrum of their activity, thereby excluding any non-specific signals, for example non-specific signals via the reporter gene pathway.

Inositol Phosphates (IP) Measurement

Phosphatidyl inositol (PI) hydrolysis may be determined as described in U.S. Pat. No. 5,436,128, which involves labeling of cells with $^3$H-myoinositol for at least 48 hours or more. The labeled cells are contacted with a test agent for one hour, then these cells are lysed and extracted in chloroform-methanol-water. This is followed by separating the inositol phosphates by ion exchange chromatography and quantifying them by scintillation counting. For agonists, fold stimulation is determined by calculating the ratio of counts per minute (cpm) in the presence of tested agent, to cpm in the presence of buffer control. Likewise, for inhibitors, antagonists and inverse agonists, fold inhibition is determined by calculating the ratio of cpm in the presence of test agent, to cpm in the presence of buffer control (which may or may not contain an agonist).

Binding Assays

In addition to the functional assays described herein-above that measure a change in parameters caused by a functional response to ligand binding, ligand binding may be determined by binding assays that measure the binding of a ligand to a T1R2-TMD or CSR:T1R receptor. Binding assays are well known in the art and can be tested in solution, in a bilayer membrane, optionally attached to a solid phase, in a lipid monolayer, or in vesicles. Binding of an enhancer to a T1R2-TMD or CSR:T1R polypeptide can be determined, for example, by measuring changes in spectroscopic characteristics (for example fluorescence, absorbance, or refractive index), hydrodynamic methods (employing for example shape), and chromatography, measuring solubility properties of a T1R2-TMD or CSR:T1R polypeptide. In one embodiment, binding assays are biochemical and use membrane extracts from cells/tissue expressing recombinant T1R2-TMD or CSR:T1R polypeptides. A binding assay may, for example, be performed as described for T1Rs by Adler et al. in US20050032158, paragraphs [0169] to [0198].

T1R2-TMD or CSR:T1R Receptor Polypeptide and Nucleic Acids and Substantially Homologous Polypeptides and Nucleic Acids The CSR:T1R chimeric protein useful in methods described herein may be selected from the group consisting of the polypeptide selected from SEQ ID NO:14, SEQ ID NO:16, the chimeric heterodimer of SEQ ID NO: 14 and SEQ ID NO:16, a heterodimer of SEQ ID NO:14 with wildtype T1R3, and a heterodimer of SEQ ID NO: 16 with wildtype T1R2. Alternatively, the CSR:T1R chimeric protein (or nucleic acid sequence encoding the CSR:T1R) may be a protein (or nucleic acid sequence encoding such a CSR:T1R receptor) that is substantially homologous to the above polypeptides (% sequence identity of at least 90%, for example at least 95% or at least 98%) and remains functional (i.e. binds to ligands and/or is activated by ligands, or encodes such a receptor).

The T1R2-TMD receptor useful in methods according to the invention may be the receptor of SEQ ID NO:2, or alternatively a receptor (or nucleotide sequence that encodes the T1R2-TMD receptor) that is substantially homologous to SEQ ID NO:2 and remains functional (i.e. binds to ligands and is activated by ligands). Such homologous receptors could be at least 90% identical to SEQ ID NO:2, preferably at least 95% identical SEQ ID NO:2. Such homologous receptors may be, for example, an allelic variant of SEQ ID NO:2, or the corresponding homologous sequence of a different species including rat (about 77.9% aminoacid sequence identity and about 81.2% nucleic acid identity), mouse (about 76.2% aminoacid sequence identity and about 80.9% nucleic acid identity), dog (about 74.4% aminoacid sequence identity and about 82.6% nucleic acid identity), or any other species having sufficient amino acid sequence identity to the human receptor.

A substantially homologous CSR:T1R chimeric protein includes such proteins where the T1R2 or T1R3 part is replaced with the relevant part of an allelic variant or different species, including T1R2 and/or T1R3 from mouse, rat, hamster, ape, and dog. Further, substantially homologous T1R2-TMD or CSR:T1R nucleotide or polypeptide sequences may be formed by conservative mutations and/or point mutations and include any conservatively modified variant as detailed below.

With respect to nucleic acid sequences, conservatively modified variants means nucleic acids which encode identical or essentially identical amino acid sequences (conservatively substituted amino acids, i.e. lysine switched to arginine and further examples as explained herein-below).

Because of the degeneracy of the genetic code, a large number of nucleic acids different in sequence but functionally identical encode any given polypeptide/protein. Such nucleic acid variations are "silent variations," which are one species of conservatively modified variations. Each nucleic acid sequence which encodes a polypeptide also describes every possible silent variation of the nucleic acid. Therefore, each codon in a nucleic acid (except AUG, which is ordinarily the only codon for methionine, and TGG, which is ordinarily the only codon for tryptophan) can be modified to yield a functionally identical nucleic acid sequence that will produce an identical polypeptide. Accordingly, each silent variation of a nucleic acid which encodes a polypeptide is implicit in each given nucleic acid sequence.

With respect to amino acid sequences, amino acid substitutions may be introduced using known protocols of recombinant gene technology including PCR, gene cloning, site-directed mutagenesis of cDNA, transfection of host cells, and in-vitro transcription which may be used to introduce such changes to the T1R2-TMD or CSR:T1R sequence. The variants can then be screened for taste-cell-specific GPCR functional activity. Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (l); 5) Isoleucine (I), Leucine (L), Methionine (M), Valine (V); and 6) Phenylalanine (F), Tyrosine (Y), Tryptophan (W). Another alternative guideline is to allow for all charged amino acids as conservative substitutions for each other whether they are positive or negative. In addition, individual substitutions, deletions or additions that alter, add or delete a single amino acid or a small percentage (for example up to 26%, up to 20%, up to 10%, or up to 5%) of amino acids in an encoded sequence are also considered to be conservatively modified variations. Substantially homologous nucleotide or polypeptide sequences have the degree of sequence identity or hybridize under certain stringent hybridization conditions as indicated below.

% Sequence Identity

For CSR:T1R, a substantially homologous nucleotide sequence has a percentage sequence identity of, for example, at least 90%, at least 95%, or at least 98%. Further, for CSR:T1R a substantially homologous polypeptide sequence has a % sequence identity of at least 90%, at least 95% or at least 98%.

For T1R2-TMD, a substantially homologous nucleotide sequence has a % sequence identity of at least 65%, at least 70%, at least 75%, at least 85%, at least 90%, at least 95%, or at least 98%. Further, for T1R2-TMD a substantially homologous polypeptide sequence has a % sequence identity of at least 74%, at least 75%, at least 80%, at least 85%, at least 90%, at least 95% or at least 98%.

Calculation of % Sequence Identity is determined as follows: BLAST (Basic Local Alignment Search Tool) is the heuristic search algorithm employed by the program blastn which is available at the National Center for Biotechnology Information website. To determine % identity of a nucleotide query sequence against another nucleotide sequence, Blastn is used, using default parameters of BLAST version 2.2.1.3, including an EXPECT (statistical significance threshold for reporting matches against database sequences) of 10, and DUST filtering. To determine % identity of a polypeptide query sequence against another polypeptide sequence, Blastp is used, using default parameters of BLAST version 2.2.1.3, including an EXPECT of 10, and DUST filtering.

Stringent Hybridization Conditions

Nucleotide sequences also are considered substantially homologous if they are capable of selectively hybridizing to the nucleotide sequences presented herein, or to their complement, under stringent hybridization conditions detailed below.

Stringent hybridization conditions are temperature of 42° C. in a solution consisting of 50% formamide, 5×SSC, and 1% SDS and washing at 65° C. in a solution consisting of 0.2×SSC and 0.1% SDS (1×SSC=0.15 M NaCl, 0.015 M sodium citrate pH 7.0). Background hybridization may occur because of other nucleotide sequences present, for example, in the cDNA or genomic DNA library being screened. A positive signal that is is at least 2 times background, optionally 10 times background hybridization, is considered a specific interaction with the target DNA. The intensity of interaction may be measured, for example, by radiolabelling the probe, e.g. with $^{32}P$.

Kit to Identify an Enhancer

The invention comprises in one embodiment a kit, for example, a screening kit or high throughput screening kit, that comprises recombinant cells that express the T1R2-TMD or CSR:T1R, or a sequence substantially homologous thereto; and that comprises an agonist of the T1R2-TMD or CSR: T1R, for example, without limitation, calcium chloride, perillartine, p-ethoxybenzaldehyde, NDHC, cyclamate, and cinnamonitrile. Using a kit comprising calcium has the advantage of binding to and activating the chimeric protein only, but not the wild-type receptor or the T1R2 and T1R3 part of the chimeric protein. Optionally, the cells further comprise a G-protein for example for calcium signalling.

Suitable G-proteins are known and described herein-above; the skilled person is aware how to introduce them into the cells if necessary. A very useful chimeric G-protein is Galpha16-gustducin 44. The agonist is provided in suitable concentrations, for example 1 nM to 10 mM, or 0.1 µM to 1 mM, for example 0.1 µM to 100 µM. Useful concentrations are, for example, for calcium chloride 0.2 to 20 mM, for p-ethoxybenzaldehyde 5 to 500 µM, for perillartine 5 to 500 µM, for cinnamonitrile 10 to 1000 µM, for cyclamate 0.01 to 5 mM, for neohesperidin dihydrochalcone (NDHC) 0.033 to 3.3 mM.

Optional kit components may include a suitable medium for culturing the recombinant cells provided, and a solid support to grow the cells on, for example, a cell culture dish or microtiter plate. These optional components will be readily available to the skilled person.

The kit may be used as follows:

(i) Recombinant cells that express the CSR:T1R chimeric proteins are grown on the solid support.

(ii) test agents at concentrations from about 1 nM or less to 100 mM or more are added to the culture medium of defined plates or wells in the presence of the agonist in a suitable concentration (iii) a change in a functional response of the cells is determined by comparing the response in the presence and absence of the test agent, and it is thereby determined whether the test agent may be an enhancer.

For example, (iii) may be performed according to any one of the assays described herein above, in combination with any one of the detection methods that report receptor activity described herein-above. This may require specifically chosen or adapted recombinant cells, which are also described herein-above. A suitable assay is, for example, the calcium flux assay to determine activation of CSR:T1R and its change in response to a test agent.

The kit may be used to identify an enhancer as follows:

(i) Recombinant cells that express the CSR:T1R chimeric protein are grown on the solid support.

(ii) test agents at concentrations from about 1 nM to 100 mM or more are added to the culture medium of defined plates or wells in the presence of the calcium agonist (for example, without limitation, in form of calcium chloride) in a suitable concentration. A suitable calcium chloride concentration is, for example, from about 0.2 to 20 mM, or 0.5 to 10 mM, or about 1 mM.

(iii) a change in a functional response of the cells to calcium is determined by comparing the response in presence and absence of the test agent, and it is thereby determined whether the test agent may be an enhancer.

Confirmation of identified enhancers: An enhancer identified by a method described herein-above may easily be confirmed by simple sensory experiments using a panel of flavorists or test persons to taste the identified enhancers. The compounds are tasted e.g. in water to confirm sweet taste or together with sweet tastants in comparison to a negative control without enhancer to confirm a modulator that enhances the sweet taste.

Large Scale Screening Assays

Transcriptional reporter assays and most cell-based assays described herein-above are well suited for screening libraries for agents that modulate CSR:T1R or T1R-TMD activity. The assays may be designed to screen large chemical libraries by automating the assay steps and providing compounds from any convenient source to the assays, which are typically run in parallel (for example in microtiter formats on microtiter plates in robotic assays). Assays may be run in high throughput screening methods that involve providing a combinatorial chemical or peptide library containing a large number of potential enhancers. Such libraries are then screened in one or more assays described herein-above to identify those library agents (particular chemical species or subclasses) that display the activity described herein-above. The enhancers thus identified can be directly used or may serve as leads to identify further enhancers by making and testing derivatives. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.).

Libraries of Test Agents

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks. A rare-chemical library is available from Aldrich (Milwaukee, Wis.).

Libraries of natural compounds in the form of bacterial, fungal, plant and animal extracts are commercially available for example from Pan Laboratories (Bothell, Wash.) or Myco-Search (NC), or are readily producible by methods well known in the art. Additionally, natural and synthetically produced libraries and compounds are readily modified through conventional chemical, physical, and biochemical means. Other libraries include protein/expression libraries, cDNA libraries from natural sources, including, for example, foods, plants, animals, bacteria, libraries expressing randomly or systematically mutated variants of one or more polypeptides, and genomic libraries in viral vectors that are used to express the mRNA content of one cell or tissue.

In a high throughput assay, it is possible to screen up to several thousand different enhancers or ligands in a single day. In particular, each well of a microtiter plate can be used to run a separate assay against a selected potential enhancer, or, if concentration or incubation time effects are to be observed, every 5-10 wells can test a single enhancer. Thus, a single standard microtiter plate can assay about 100 enhancers. If 1536-well plates are used, then a single plate can easily assay from about 100 to about 1500 different compounds. It is possible to assay several different plates per day; assay screens for up to about 6,000-20,000 different compounds are possible.

Types of Test Agents that May be Tested for their T1R-TMD or CSR:T1R Modulating Effect in the Assay Methods The test agents may be any agent including small chemical compounds, chemical polymers, biological polymers, peptides, proteins, sugars, carbohydrates, nucleic acids and lipids. An agent can be a synthetic compound, a mixture of compounds, a natural product or natural sample, for example plant extract, culture supernatant, or tissue sample. As examples of compounds that may modify sweet taste there may be mentioned methyl chavicol, Theasaponin E1, Acesulfame K, Alitame, Aspartame, CH 401, Dulcin, Neotame, sodium Cyclamate, Sucralose, Superaspartame, Cynarin, Glycyphyllin, Rebaudioside C, Abrusoside A, Abrusoside B, Abrusoside C, Abrusoside D, Abrusoside E, Apioglycyrrhizin, Araboglycyrrhizin, Baiyunoside, Brazzein, Bryodulcoside, Carnosifloside V, Carnosifloside VI, D. cumminsii, Cyclocarioside A, Cyclocarioside I, Dulcoside A, Glycyrrhizic Acid, Hernandulcin, Hernandulcin, 4beta-hydroxy-Hesperitin-7-Glucoside Dihydrochalcone, Huangqioside E, Huangqioside E, 3-Hydroxyphloridzin, 2,3-Dihydro-6-Methoxy 3-O-Acetate, Mabinlin Maltosyl-Alpha-(1,6)-Neohesperidin Dihydrochalcone, Mogroside IIE, Mogroside III, Mogroside IIIE, Mogroside IV, Mogroside V, 11-Oxo Mogroside V, Monatin, Monoammonium Glycyrrhizinate (Mag), Mukuroziosid Iib, Naringin Dihydrochalcone, Neohesperidin Dihydrochalcone (NHDHC), Neomogroside, Osladin, Periandrin I, Periandrin II, Periandrin III, Periandrin IV, Periandrin V, Phlomisoside I, Phlorizin, Phyllodulcin, Polypodoside A, Potassium magnesium calcium glycyrrhizin, Pterocaryosides A, Pterocaryosides B, Rebaudioside A, Rebaudioside B, Rubusoside, Scandenoside R6, Siamenoside I, Sodium glycyrrhizinate, Steviolbioside, Stevioside, alpha-Glycosyl Suavioside A, Suavioside B, Suavioside G, Suavioside H, Suavioside I, Suavioside J, Thaumatin, Triammonium Glycyrrhizinate (TAG), Trilobatin Curculin, Strogin 1, Strogin 2, Strogin 4, Miraculin, Hodulcin, Jujubasaponin II, Jujubasaponin III, Abrusoside E, Periandrinic acid I, monoglucuronide, Periandrinic acid II, monoglycuronide, Chlorogenic Acid, beta-(1,3-Hydroxy-4-methoxybenzyl)-Hespertin Dihydrochalcone, 3'-Carboxy-Hespertin Dihydrochalcone, 3'-Stevioside analogue.

Sweetness enhancers identified by the methods described herein may include, for example, enhancers of artificial sweeteners that are able to elicit a sweet taste sensation. Consumables include food products, beverages, oral care products, and compositions for admixture to such products, in particular flavour compositions. Flavour compositions may be added to processed foods or beverages during their processing, or they may actually be consumables in their own right, e.g. condiments such as sauces and the like. Sweet tastants are particularly useful in confectionary and other sweet consumables including desserts and savoury and sweet-sour consumables. Examples of consumables include confectionary products, cakes, cereal products, baker's products, bread products, gums, chewing gums, sauces (condiments), soups, processed foods, cooked fruits and vegetable products, meat and meat products, egg products, milk and dairy products, cheese products, butter and butter substitute products, milk substitute products, soy products, edible oils and fat products, medicaments, beverages, alcoholic drinks, beers, soft drinks, food extracts, plant extracts, meat extracts, condiments, sweeteners, nutraceuticals, tablets, lozenges, drops, emulsions, elixirs, syrups and other preparations for making beverages, instant beverages and effervescent tablets.

Sequences of Nucleic Acids and Proteins

The sequences employed in the constructs and methods described-herein can be found in the sequence listing hereinbelow.

T1R2-TMD Sequences

The sequences are shown in the sequence listing hereinbelow. SEQ ID NO:1 corresponds to the nucleotide/nucleic acid sequence encoding the T1R2-TMD receptor, SEQ ID NO: 2 corresponds to the polypeptide/amino acid sequence of the T1R2-TMD receptor protein.

In the transfected construct, the SST TAG (SEQ ID NO:3) is followed by the nucleic acid coding for the novel T1R2-TMD protein (SEQ ID NO:1), which is followed by the HSV TAG nucleic acid (SEQ ID NO:5).

The resulting protein will accordingly comprise the following amino acids in the order indicated: amino acids of SEQ ID NO:4, SEQ ID NO:2, and SEQ ID NO:6.

SEQ ID NOS: 1+2: T1R2-TMD nucleic acid and protein
SEQ ID NOS: 3+4: SST TAG nucleic acid and protein
SEQ ID NOS: 5+6: HSV TAG nucleic acid and protein
SEQ ID NOS: 7+8: Forward and reverse primer for T1R2-TMD vector construct
SEQ ID NOS: 9+10: T1R2 full length (nucleic acid and protein)
SEQ ID NOS: 11+12: T1R3 full length (nucleic acid and protein)

CSR:T1R Sequences

SEQ ID NO:13 corresponds to the nucleotide/nucleic acid sequence encoding the CSR:T1R2 chimeric protein, SEQ ID NO: 14 corresponds to the polypeptide/amino acid sequence of the CSR:T1R2 chimeric protein.

SEQ ID NO:15 corresponds to the nucleotide/nucleic acid sequence encoding the CSR:T1R3 chimeric protein, SEQ ID NO: 16 corresponds to the polypeptide/amino acid sequence of the CSR:T1R3 chimeric protein.

Together as a complex comprising two subunits, the CSR:T1R2 chimeric protein and the CSR:T1R3 chimeric protein form a functional chimeric sweet receptor.

The transfected construct will, for example, comprise SEQ ID NO:13 or 15 followed by the SEQ ID NO:17, the HSV tag at the C-terminus.

The resulting protein will accordingly comprise the following amino acids: amino acids of SEQ ID NO:14 followed by SEQ ID NO:18, or SEQ ID NO: 16 followed by SEQ ID NO:18.

The known full length hCaSR receptor nucleic acid and protein sequences are given in SEQ ID NO: 19+20.

SEQ ID NO: 13+14: CSR:T1R2 nucleic acid+protein
SEQ ID NO: 15+16: CSR:T1R3 nucleic acid+protein
SEQ ID NO: 17+18: HSV tag at C-terminus nucleic acid+protein
SEQ ID NO: 19+20: hCaSR nucleic acid+protein
SEQ ID NO: 21-24: primer sequences, compare example 13 and example 15
SEQ ID NO: 25-26: primer sequences
SEQ ID NO: 27-28: T1R3 TMD nucleic acid+protein There now follows a series of examples that serve to illustrate the above-described methods. The following examples are merely illustrative and should not be construed as limiting the methods or kit in any manner.

Examples

An overview of the examples is given below.
Example 1 describes a general method for measuring taste receptor activity.
Examples 2-5 describe the preparation of the different T1R vector constructs.
Examples 6-8 describe the transfection of cells with the constructs.
Examples 9-12 describe the identification, without limitation, of a variety of sweetness enhancers.
Example 13 describes a general method of measuring sweetness.
Examples 14-20 describe control experiments measuring sweetness of an enhancer in the absence of another sweet tastant.
Examples 21-29 relate to mixtures of sweetness enhancers with sweet tastants.
Examples 30-33 describe control experiments measuring sweetness of an enhancer in the absence of another sweet tastant.
Example 34-36 shows admixtures of two or more sweetness enhancers together with a sweet tastant.

1. Fluo-4 Calcium Assay

Fluo-4 is a fluorescent indicator for intracellular calcium and allows the determination of changes in calcium concentration, in particular an increase in response to receptor activation occurring after ligand addition.

HEK293 cells stably expressing Gα16-gustducin 44 (Gα16gust44) were used as host cells and transfected with various constructs as described in examples 2-5.

Black, clear-bottom 96-well plates were used for all assays. They were seeded the day before the assay with 8500 transfected cells per well and maintained at 37° C. overnight in a growth medium appropriate for the cells used. For EK293 cells, Dulbecco's Modified Eagle medium containing high glucose, L-glutamine, pyroxidine hydrochloride, and supplemented with 10% fetal bovine serum was used for growth and maintenance of the BEK293 cells.

At the time of the assay, the growth medium was discarded and cells were incubated for 1 hour (at 37° C. in the dark) with 50 μl of a calcium assay solution consisting of 1.5 μM Fluo-4 AM (Molecular Probes™, Invitrogen, US) and 2.5 μM probenicid (Sigma-Aldrich) dissolved in a C1 buffer solution. C1 buffer solution contains 130 mM NaCl, 5 mM KCl, 10 mM Hepes, 2 mM $CaCl_2$ and 10 mM glucose (pH 7.4).

After the initial 1 hour loading period, the plates were washed 5 times with 100 μl per well of C1 buffer using an automated plate washer (BioTek) and after washing, the cells were further incubated in 100 μl C1 buffer per well for 30 minutes at room temperature in the dark to allow for complete de-esterification of the Fluo-4-AM. The buffer solutions were discarded, the plate was washed 5 times with 100 μl C1 wash buffer and finally the cells were placed in 180 μl of C1 wash buffer.

For assay reading, the plate was placed in a FLIPR (fluorescence imaging plate reader (FLIPR-Tetra, Molecular Devices), and receptor activation was initiated following addition of 20 μl of a 10× concentrated ligand stock solution.

Fluorescence was continuously monitored for 15 seconds prior to ligand addition and for 105 seconds after ligand addition (45-105 sec may be sufficient).

Receptor activation is given in relative fluorescence units (RFU) and is defined by the following equation:

> Fluorescence Increase=Maximum Fluorescence-baseline fluorescence, wherein the baseline fluorescence represents the mean fluorescence calculated for the first 10 to 15 seconds prior to ligand addition.

Alternatively, Receptor activation is determined by the increase in peak fluorescence (F) normalized to the baseline fluorescence ($F_0$). The data are normalized using the following equation: $\Delta F/F=(F-F_0)/F_0$, where F is the peak fluorescence signal and $F_0$ is the baseline fluorescence signal, wherein the baseline fluorescence represents the mean fluorescence calculated for the first 10 to 15 seconds prior to ligand addition.

As a negative control, mock transfected cells were exposed to the same concentration of ligand and the concentration of calcium traces not corresponding to a signal was determined. Cells with an activated receptor were identified by the signal (RFU or ΔF/F) being significantly above the negative control.

2. Preparation of a T1R2-TM) Vector Construct

PCR using Pfu polymerase (Invitrogen) was used to generate the T1R2-TMD construct using the specific primers listed below:

```
T1R2-TMD Forward Primer (Seq ID NO: 7):
5'-TAT AGA ATT CGC ACC CAC CAT CGC TGT GGC C-3'

T1R2-TMD Reverse Primer (Seq ID NO: 8):
5'-ATA TGC GGC CGC AGT CCC TCC TCA TGG T-3'
```

The template for the PCR amplification was a full length cDNA for human T1R2 isolated from a cDNA library generated from human fungiform papillae taste tissue. Reaction parameters were: 94° C. for 5 min followed by 35 cycles of 94° C. for 45 seconds, 54° C. for 15 seconds and 68° C. for 1 minute, followed by a final extension cycle of 68° C. for 10 minutes.

The resulting nucleic acid fragment (compare Seq ID NO:1) was separated by gel electrophoresis, purified and sub-cloned into the pCR-Topo-II vector (Invitrogen) and the resulting clones were verified by DNA sequencing to ensure absence of mutations arising from the PCR amplification. After sequencing, the T1R2-TMD insert was sub-cloned into an expression cassette based on pcDNA4-TO (Invitrogen). The cloning cassette already contains the first 45 amino acids of the rat somatostatin type 3 receptor at the N-terminus to facilitate cell surface membrane targeting of the transgene (described by Bufe et al., 2002, *Nat. Genet.*, 32(3), 397-401). The C-terminus of this vector encodes the herpes simplex virus (HSV) glycoprotein D epitope, which can be used for immunocytochemistry studies using a specific antibody that binds to this epitope. The resulting vector construct allows for expression of the T1R2-TMD protein of joined amino acid sequences of Seq ID NO:2 (T1R2-TMD) preceded by Seq ID NO:4 (45 amino-acids of rat somatostatin) and followed by Seq ID NO:6 (HSV epitope) (in amino terminus to C terminus direction).

By methods analogous to those outlined above a T1R3-TMD receptor, which has been truncated to remove the extracellular domain of T1R3, can be created. This entails the use of T1R3 cDNA as a PCR template (with accordingly different forward and reverse primers specific to the 5' and 3' end of the T1R3 transmembrane domain-encoding region). The T1R3-TMD receptor can then be used to carry out similar assays to the T1R2-TMD as disclosed herein. For example, T1R3-TMD alone can be used in binding assays, or it can be used e.g. in conjunction with T1R2-TMD in either binding or activation assays.

3. Preparation of CSR:T1R2 Vector Construct

The CSR:T1R chimeric cDNA vector construct was generated by joining two DNA fragments generated by PCR via a common restriction enzyme site in both PCR products, a fragment that encodes the extra-cellular amino terminal domain (ATD) of hCaSR (1–$Phe^{539}$) and a fragment that encodes containing the cysteine-rich domain (CRD), transmembrane (TMD) and C-terminus of T1R2 beginning at $Ser^{493}$.

To facilitate the preparation of the CSR:T1R2 chimeric DNA, a Sac II site was introduced into the primers that were used to form the two fragments described herein above. Using these introduced sites and the appropriate restriction enzyme in buffers under conditions well known in the art, the fragments were joined by enzymatic ligation.

These Sac II sites in the formed PCR-products/fragments are located at the C-terminal end of the hCaSR ATD fragment and the N-terminal end of the T1R2 fragment, respectively, allowing for ligation of the two PCR-products/fragments of the chimeric DNA. Incorporation of this Sac II site converts $Phe^{539}$ in the hCaSR into an arginine residue. PCR was used to amplify the fragments that comprise the CSR:T1R2 chimeric cDNA fragment using the specific primers of SEQ ID NO:21-24 which are given below. F designates the forward primer, R the reverse primer.

The underlined letters designate restriction sites located within the primers for subsequent sub-cloning of the PCR products.

```
hCaSR-ATD primer F (Seq ID NO: 21):
CACCAAGCTTATGGCATTTTATAGCTGC hCaSR-ATD primer R (Seq ID NO: 22):
ATATCCGCGGCACCTCCCTGGAGAACCC T1R2-fragment primer F (Seq ID NO: 23):
ATATCCGCGGTCCATGTGTTCCAAGAGG T1R2-fragment primer R (Seq ID NO: 24):
ATATGCGGCCGCAGTCCCTCCTCATGGT
```

The templates for the PCR amplifications were full length cDNAs encoding the human CaSR (commercially available from Origene Inc., USA), and the human T1R2, which was isolated from a cDNA library generated from human fungiform papillae taste tissue. PCR reaction parameters were: 94° C. for 5 min followed by 35 cycles of 94° C. for 45 seconds, 54° C. for 15 seconds and 72° C. for 2 minutes, followed by a final extension cycle of 72° C. for 10 minutes.

The resulting nucleic acid fragments were separated by gel electrophoresis, purified and sub-cloned into the pCR-Topo-II vector (Invitrogen) and the resulting clones were verified by DNA sequencing to ensure absence of mutations arising from the PCR amplification. After sequencing, the inserts were sub-cloned into an expression cassette vector construct based on the pcDNA4/T0 vector (purchased from Invitrogen, USA) via 3-piece ligation, allowing for assembly of the CSR:T1R2 chimeric cDNA fragment in the vector construct.

The C-terminus of the resulting insert encodes the herpes simplex virus (HSV) glycoprotein D epitope (provided by the pcDNA4/T0 vector), which can be used for immunocytochemistry studies using a specific antibody that binds to this epitope. The resulting CSR:T1R2 vector construct with CSR:T1R2 cDNA allows for expression of the CSR:T1R2:HSV protein of joined amino acid sequences of Seq ID NO: 14 (CSR:T1R2) followed by Seq ID NO: 18 (HSV epitope) (in amino terminus to C terminus direction).

4. Preparation of the CSR:T1R3 Vector Construct

The CSR:T1R3 chimeric cDNA vector construct was generated by joining two DNA fragments generated by PCR via a common restriction enzyme site in both PCR products, namely the joining of a PCR product encoding the extracellular amino terminal domain (ATD) of hCaSR (1-Phe$^{539}$) to a fragment of T1R3 encoding the cysteine-rich domain (CRD), trans-membrane (TMD) and C-terminus beginning at Ser$^{497}$.

To facilitate the preparation of the CSR:T1R3 chimeric cDNA vector construct, a Sac II site was introduced into the primers which were used to make the above-described two fragments.

These Sac II sites in the formed PCR-products/fragments are located at the C-terminal end of the hCaSR-ATD fragment and the N-terminal end of the T1R3 fragment, respectively, allowing for ligation of the two fragments. Incorporation of this Sac II site results in a vector construct that encodes an arginine instead of phenylalanine at position 539 of the original hCaSR. Using the introduced ligation sites and the appropriate restriction enzyme in buffers and under conditions well known in the art, the fragments were joined by enzymatic ligation.

PCR was used to amplify the fragments that comprise the CSR:T1R3 chimeric cDNA fragment using the specific primers of Seq ID NO: 25 and Seq ID NO:26 listed below. Afterwards, the amplified PCR-products of T1R3 and the amplified PCR products of hCaSR (the latter formed as described in example 2 above) were ligated via the restriction sites indicated in the primer listed below. F designates the forward primer, R the reverse primer. The underlined letters designate restriction sites located within the primers for subsequent ligation and sub-cloning of the amplified PCR products.

hCaSR-ATD F and hCaSR-ATD R:

Seq ID NO: 25 and Seq ID NO: 26 as indicated in example 3 above.

```
T1R3-fragment primer F (Seq ID NO: 25):
ATATCCGCGGTCCCGGTGCTCGCGGCAG

T1R3-fragment primer R (Seq ID NO: 26):
ATATGCGGCCGCACTCATGTTTCCCCTGATT
```

The template for the PCR amplification was a full length cDNA for either the hCaSR (purchased from Origene Inc., USA), or the hT1R3, which was isolated from a cDNA library generated from human fungiform papillae taste tissue. PCR reaction parameters were: 94° C. for 5 min followed by 35 cycles of 94° C. for 45 seconds, 54° C. for 15 seconds and 72° C. for 2 minutes, followed by a final extension cycle of 72° C. for 10 minutes.

The resulting nucleic acid fragments (ligation is performed later after the fragments are verified) were separated by gel electrophoresis, purified and sub-cloned into the pCR-Topo-II vector (Invitrogen, USA). The resulting clones were verified by DNA sequencing to ensure absence of mutations arising from the PCR amplification.

After sequencing, the inserts were sub-cloned into an expression cassette vector construct based on the pcDNA4/T0 vector (purchased from Invitrogen, USA) via 3-piece ligation, forming the CSR:T1R3 vector construct. The C-terminus of the vector construct encodes the herpes simplex virus (HSV) glycoprotein D epitope, which can be used for immunocytochemistry studies using a specific antibody that binds to this epitope. The resulting vector construct allows for expression of the CSR:T1R3:HSV protein of joined amino acid sequences of Seq ID NO: 16 (CSR:T1R3) followed by Seq ID NO: 18 (HSV epitope) (in amino terminus to C terminus direction).

5. Preparation of the T1R2 T1R3 Vector Constructs (Wild-type Receptors for Comparison)

To form the T1R2 and T1R3 vector construct, cDNA fragments containing the entire protein coding sequences for human T1R2 and T1R3 were isolated from a human fungiform cDNA library, fully sequenced and then sub-cloned into pCDNA3.1 (invitrogen) by standard methods.

6. Transfection of T1R2-TMD into Cells, Cells Stably Expressing T1R2-TMD and G α16gust44

Human cell lines that stably express human T1R2-TMD were generated by transfecting a linearized pcDNA 4-T0 vector (Invitrogen) containing the human T1R2-TMD (formed as described in example 2) into a Gα16gust44 expressing cell line (which was formed as described in WO 2004/055048). This cell line shows enhanced coupling to taste receptors, is tetracycline inducible, stably expresses the Gα16gust44 promiscuous G-protein, and is based on the HEK-293-T-Rex cell line (commercially available from invitrogen, USA).

Transfection was performed as follows:

On day 0, the HEK293T/Gα16gust44 cells were plated in 6-well black, clear-bottom plates at a density of 900,000 cells per well and grown overnight in selective growth media. On day 1, the media was changed to an antibiotic-free and serum-free growth medium and the cells were transfected using 4 µg of linearized T1R2 TMD vector construct DNA and 0.3 µl of Lipofectamine 2000 (Invitrogen). The lipofectamine/DNA mixture was incubated on the cells for 3-4 hours and then replaced with an antibiotic-free, serum-containing growth medium. After 24 hours the cells were re-plated in selective medium containing DMEM supplemented with 10% FBS, 0.005 mg/ml blasticidin, 0.36 mg/ml G418, and 0.1 mg/ml zeocin (Invivogen) at 37° C. After 2-4 weeks zeocin-resistant colonies were selected, expanded, and tested by calcium imaging as described in example 1 for responses to 50 µM perillartine.

Resistant colonies were expanded, and identified as containing T1R2-TMD by their response to 50 µM perillartine, which was determined via automated fluorimetric imaging on the FLIPR-Tetra instrumentation (Molecular Devices) using the methods described in example 1 following induction of T1R2-TMD expression with 10 µg/ml tetracycline.

All potential clones were also evaluated for a functional response to 50 µM perillartine in the absence of tetracycline induction to identify any clones that are basally expressing low-level but functionally sufficient levels of the T1R2-TMD receptor (the tetracycline-regulated systems such as the T-Rex HEK-293 (Invitrogen) are known to have a low-level basal expression of transgenes due to the inherent leakiness of the system).

As a result of said evaluation, it was determined that when these cell lines are exposed to perillartine, many cell clones respond to this stimulus with a significant increase in fluorescence which is greater than 10-times the signal compared to the signal of the negative control (cells that express Gα16gust44 promiscuous G-protein but not T1R2-TMD).

Signals are significantly lower in cells treated with tetracycline to induce over-expression of the T1R2-TMD. The lack of response in the tetracycline-induced T1R2-TMD cells may be due to cellular toxicity arising from tetracycline-induced over-expression of the T1R2-TMD.

|  | AVERAGE [RFU] | S.D. [RFU] |
|---|---|---|
| T1R2-TMD/Gα16gust44 | 973.06 | 69.48 |
| Gα16gust44 ONLY (neg. control) | 73.78 | 55.43 |

7. Transfection of Cells Stably Expressing the T1R2/T1R3 Sweet Receptor Heterodimer and Gα16gust 44

T1R3 was constitutively over-expressed in the presence of a tetracycline-regulated T1R2 to avoid possible cytotoxic effects of constitutive over-expression of both proteins. Placing one subunit of the heterodimer (T1R2) in a tetracycline-regulated vector allows regulating its expression level so that viability and functionality of the stable clonal lines can be optimised accordingly.

Human cell lines that stably express the human T1R2/T1R3 sweet heterodimer were generated by first transfecting a linearized pIRES-Puro vector (Clontech) containing the human T1R3 into a Gα16gust44 expressing cell line, which was formed as described in WO 2004/055048. This cell line shows enhanced coupling to taste receptors, is tetracycline inducible, stably expresses the Gα16gust44 promiscuous G-protein, and is based on the HEK-293-T-Rex cell line (commercially available from Invitrogen, USA). After generation of a heterogeneous population of cells stably expressing T1R3, a linearized pcDNA4-TO vector (Invitrogen) containing human T1R2 cDNA was transfected.

After 24 hours the cells were re-plated at 10× dilutions up to 1:150,000 in selective medium containing Glutamax DMEM (Invitrogen) supplemented with 10% FBS, 0.005 mg/ml blasticidin, 0.36 mg/ml G418, and 0.4 µg/ml puromycin at 37° C. After 2 weeks a puromycin-resistant heterogeneous population of T1R3-expressing cells were then transfected with 4 µg of the linearized T1R2 vector construct DNA and 0.3 µl of Lipofectamine 2000 (invitrogen). The lipofectamine/DNA mixture was incubated on the cells for 3-4 hours and then replaced with an antibiotic-free, serum-containing growth medium. After 24 hours the cells were re-plated in selective medium containing Glutamax DMEM supplemented with 10% FBS, 0.005 mg/ml blasticidin, 0.36 mg/ml G418, 0.4 g/ml puromycin, and 0.1 mg/ml zeocin at 37° C.

Resistant colonies were expanded, and identified as containing the T1R2/T1R3 sweet heterodimer by their response to various sweetener compounds including sucrose, sucralose, aspartame and acesulfame K, which was determined via automated fluorimetric imaging on the FLIPR-Tetra instrumentation (Molecular Devices) using the methods described in example 1. All potential clones were also evaluated for a functional response to sweet tastants in the presence of 10 µg/ml tetracycline (to induce over-expression of T1R2). Potential clones were also tested in the absence of tetracycline induction to identify any clones that are basally expressing T1R2 at a low level, but have sufficient expression of the T1R2 receptor to allow for assembly with T1R3 resulting in a functional sweet heterodimer complex (the tetracycline-regulated systems such as the T-Rex HEK-293 (Invitrogen) are known to have a low-level basal expression of transgenes due to the inherent leakiness of the system).

As a result of said evaluation, it was determined that when these cell lines, which were not treated with tetracycline, are exposed to sweet tastants, many of the cell clones respond to these stimuli with a significant increase in fluorescence (greater than 10-times signal in negative control cells). Signals were lower in cells treated with tetracycline to induce over-expression of the T1R2. The lower response in the tetracycline-induced T1R2/T1R3 cells may be due to cellular toxicity arising from tetracycline-induced over-expression of the T1R2. One clonal cell line exhibiting the greatest response to sweet tastants was propagated and used for subsequent comparisons.

8. Transfections of CSR:T1R2/CSR:T1R3, and T1R2/T1R3 Heterologous Expression

Transfected vector constructs used were those described in examples 3, 4 and 5 formed as described above. For hCaSR, a commercially available pCMV-based vector construct which is based on the fall length cDNA was used (TRUE-CLONE collection, Origene Inc., USA).

HEK293T cells that stably express Gα16gust44 (formed as described in WO 2004/055048) were transfected with the CSR:T1R2 and CSR:T1R3 vector constructs, or with T1R2 and T1R3, or hCaSR as follows:

On day 0, the HEK293T/Gα16gust44 cells were plated in 96-well black, clear-bottom plates at a density of 8500 cells per well and grown overnight in selective growth media. On day 1, the media was changed to an antibiotic-free and serum-free growth medium and the cells were transfected using 75 ng each of CSR:T1R2 and CSR:T1R3 (total 150 ng), T1R2 and T1R3 (total 150 ng), or 75 ng hCaSR vector construct DNA and 0.3 µl of Lipofectamine 2000 (Invitrogen).

The hCaSR vector is used as a positive control for a GPCR that is sensitive to calcium, as it is sensitive to calcium and the calcium binding site lies in the VFT of this receptor, which is where the VFT for the chimera is derived from.

For transfection of either the CSR:T1R2/CSR:T1R3 or T1R2/T1R3 heterodimers, 75 ng of each vector construct was combined for a total of 150 ng per pair and used together with 0.3 μl of Lipofectamine 2000. 75 ng of hCaSR vector DNA was used for this calcium-sensing monomeric GPCR.

The above-described lipofectamine/DNA mixtures were incubated on the cells for 3-4 hours and then replaced with an antibiotic-free, serum-containing growth medium. The cells were grown overnight and the Fluo-4 calcium assay was performed as described in example 1.

The cells transiently transfected with one of the above-described vector constructs were identified using a fluorescence imaging plate reader (FLIPR-Tetra, Molecular Devices) as described in example 1.

9. Identification of p-ethoxybenzaldehyde as T1R2-TMD Agonist

Cells employed were HEK293T cells stably expressing Gα16gust44 and stably transfected with T1R2-TMD, which were formed as described in example 6.

Intracellular calcium responses to 100 μM p-ethoxybenzaldehyde were determined.

Cells were plated in black, clear-bottom plates (Costar) at a density of 8500 cells/well and maintained in selective growth media (as described in example 6) for 48 hours before determining receptor activity as described in example 1.

The cells were not induced with tetracycline since the particular clone selected already basally expressed sufficient levels of the T1R2-TMD to generate a robust increase in intracellular calcium following ligand stimulation.

The data was calculated as described in example 1 and illustrated the net increase in fluorescence over baseline following stimulation of the cells with 100 μM p-ethoxybenzaldehyde. The data represent the mean±Standard deviation of six replicate experiments.

Significant increases in calcium signalling were observed upon stimulation with p-ethoxybenzaldehyde in cells stably expressing the human T1R2-TMD but not in the negative control (host cells expressing the Gα16gust44 chimeric G-protein but not T1R2-TMD).

|  | AVERAGE [RFU] | S.D. [RFU] |
|---|---|---|
| T1R2-TMD/Gα16gust44 | 728.135 | 211.5451 |
| Gα16gust44 ONLY (neg. control) | 46.835 | 29.64899 |

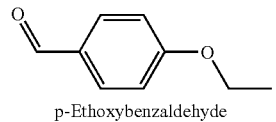

p-Ethoxybenzaldehyde

10. Dose Response Curves of T1R2-TMD Homomer and T1R2/T1R3 Heterodimer to p-ethoxybenzaldehyde The method quantitates T1R2-TMD activity and allows, for example, predictions of the potency of identified candidate enhancers including sweet tastants.

HEK293T cells that stably express Gα16gust44 and T1R2-TMD (formed as described in example 6) are loaded with the calcium dye Fluo-4, and their response to p-ethoxybenzaldehyde is measured by using fluorescent calcium signals as described in example 1. The data was calculated as described in example 1 (net increase in fluorescence over baseline following stimulation of the cells with increasing doses of p-ethoxybenzaldehyde, over a range of 0.1 to 200 μM). The data includes the mean±standard deviation (STD) of three replicate experiments.

To confirm the in vivo relevance, the dose-response curve of signals elicited by p-ethoxybenzaldehyde in T1R2-TMD expressing cells are compared to the signals obtained in cells that stably express the T1R2/T1R3 heterodimer. The two dose-response curves are found to match closely (see FIG. 1).

The results are shown in the table below and the dose response curves are shown in FIG. 1. The data in the table was curve-fit with the GraphPad Prism software package (GraphPad Software, Inc) using a 4-parameter logistic non-linear regression equation, shown below:

$$Y = \text{Bottom} + (\text{Top} - \text{Bottom})/(1+10^{((\log EC50 - X)}$$
$$* \text{HillSlope}) \text{ where:}$$

X is the logarithm of p-ethoxybenzaldehyde concentration, Y is the response, EC50 represents the agonist concentration that elicits a 50% of maximum response.

In a plot of response vs. log concentration, the value of Y is seen to rise with increasing concentration with a sigmoid shape.

The EC50 value, which indicates receptor sensitivity (a lower EC50 value indicates greater sensitivity to an agonist), was calculated from the fluorescence and p-ethoxybenzaldehyde concentration data for concentrations from 200 μM and lower in half-increments (set forth in the table below). The calculated EC50 value for T1R2-TMD is 124 μM and for the T1R2/T1R3 heterodimer is 64.51 μM. The T1R2-TMD exhibited a greater maximal response to the p-ethoxybenzaldehyde but had a similar EC50, which is in the same sensitivity range as the sweet heterodimer, indicating that T1R2-TMD is a biologically relevant receptor.

| Conc. [μM] | T1R2-TMD | | T1R2/T1R3 heterodimer | |
|---|---|---|---|---|
|  | AVERAGE [RFU] | S.D. [RFU] | AVERAGE [RFU] | S.D. [RFU] |
| 200 | 781.84 | 67.74 | 185.00 | 73.73 |
| 100 | 395.79 | 185.27 | 53.26 | 20.38 |
| 50 | 131.38 | 35.88 | 39.07 | 18.27 |
| 25 | 23.25 | 5.16 | 27.74 | 6.16 |
| 12.5 | 18.73 | 8.70 | 19.65 | 6.37 |
| 6.25 | 17.07 | 10.03 | 15.13 | 2.97 |
| 3.125 | 15.71 | 5.31 | 12.55 | 3.53 |
| 1.56 | 16.91 | 6.33 | 15.12 | 3.22 |
| 0.75 | 16.37 | 4.35 | 12.70 | 3.01 |
| 0.35 | 15.87 | 5.90 | 11.24 | 1.51 |
| 0.15 | 16.49 | 3.54 | 9.80 | 2.64 |
| 0.1 | 17.97 | 6.86 | 11.12 | 6.51 |

11. Identification of Compounds that Activate T1R2-TMD a but not the T1R2/T1R3 Heterodimer Using the calcium flux assay described in example 1, a panel of 88 test agents were evaluated for T1R2-TMD receptor-dependent responses. Test agents were tested in duplicate at a final concentration of 100 μM. The signals elicited by the test agents in cells that stably express Gα16gust44 and T1R2-TMD containing cells (formed as described in example 6) were compared to the signals obtained in cells that stably express Gα16gust44 and the T1R2/T1R3 heterodimer (formed as described in example 7), and as a negative control, cells that stably express Gα16gust44 were used.

The data was calculated as described in example 1 (net increase in fluorescence over baseline following stimulation of the cells with test agonist) and the results of the calcium signals for the identified agents that strongly activate the T1R2-TMD but elicit little or no activation of the T1R2/T1R3 heterodimer or the negative control are shown in the table below. The data corresponds to the average of two replicates from one representative experiment, which was confirmed in subsequent tests.

For the identified compound shown in the table below, a significant increase in the calcium signal was observed upon stimulation with said compound in cells stably expressing T1R2-TMD. Cells expressing the T1R2/T1R3 heterodimer showed no signals significantly above the negative control.

The result shows that T1R2-TMD is activated by a compound that does not activate the T1R2/T1R3 heterodimer. Accordingly, assays based on the T1R2-TMD homomer can identify enhancers that cannot be identified using assays performed in the presence of T1R3 and based on the T1R2/T1R3 heterodimer.

Methyl chavicol (FEMA #2411, Estragole; p-Methoxyallylbenzene) is a known flavour described to have a sweet taste and the taste is described as follows: "sweet, herbaceous, anise-fennel odor", "sweet, phenolic, anise, harsh, spice, green, herbal, minty" odor and a "sweet, licorice, phenolic, weedy, spice, celery-like" taste at 10 ppm.

The transfections were performed as described in example 8. Results were calculated as described in example 1 (data indicates the net increase in fluorescence over baseline after stimulation (Relative Fluorescent Units or RFU); the mean (AVG) and the ±Standard deviation (S.D.) of six replicate experiments is given). The following ligands were used to stimulate the transfected cells in the concentrations as indicated in brackets: calcium chloride (2 mM), sucralose (0.5 mM), aspartame (0.85 mM), perillartine (50 µM), cinnamonitrile (100 µM), cyclamate (1 mM), neohesperidin dihydrochalcone (NDHC) (0.33 mM). The signals obtained are the fluorescence in RFU corresponding to the calcium increase of the cell in response to a direct or indirect interaction with the transfected receptor ("signal").

Mock transfected HEK293T/Gα16gust44 cells transfected without construct that do not express a sweet receptor were used as a negative control to determine the background level of fluorescence. The transfected cells are exposed to the sweeteners as indicated and to a positive control (calcium) for the proteins containing calcium-sensing domains, and to a negative control (C1 buffer).

| T1R2-TMD ACTIVITY | T1R2 TMD AVG(RFUs) | T1R2 TMD S.D.EV(RFUs) | SWEET AVG(RFUs) | SWEET S.D.EV(RFUs) | GUST44 AVG(RFUs) | GUST44 S.D.EV(RFUs) |
|---|---|---|---|---|---|---|
| METHYL CHAVICOL | 728.135 | 211.5451357 | 21.195 | 3.896158364 | 46.835 | 29.64898734 |

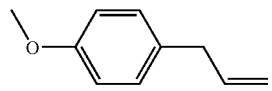

METHYL CHAVICOL

Compounds that specifically bind T1R3-TMD also can be identified by methods analogous to those described in example 11 above, but using a binding assay instead of a functional assay. Further assays can be carried out with a T1R2-TMD/T1R3-TMD heterodimer by methods analogous to those used in examples 12A and 12B below.

12. Activation of CSR:T1R2/CSR:T1R3

While the receptors, nucleic acids, polypeptides, methods and kit described below are illustrative embodiments of the in vitro assays performed in the invention (examples 12A and 12B), other similar embodiments may be used or modifications and additions may be made to the described embodiments for performing the same function(s). Further, all embodiments disclosed are not necessarily exclusive of each other, as various embodiments may be combined to provide the desired characteristics. Variations can be made by one having ordinary skill in the art without departing from the spirit and scope of the disclosure. Therefore, the receptors, nucleic acids, polypeptides, methods and kit should not be limited to any single embodiment, but rather construed in breadth and scope in accordance with the recitation of the claims.

12A. Preparation and Assay of Transiently Transfected Cell Lines Expressing the CSR:T1R2/CSR:T1R3 Heterodimer The intracellular calcium response following stimulation with various ligands was determined in HEK293T cells stably expressing Gα16gust44 and transfected with CSR:T1R2/CSR:T1R3 chimeric heterodimer. The results were compared to results obtained in cells transfected with both the T1R2 vector construct and the T1R3 vector construct which are described in example 5 (to form the T1R2/T1R3 sweet heterodimer) or the hCaSR vector construct described in example 4 (to form monomeric hCaSR).

The results are shown in the table below. The AVG columns give the mean fluorescence and the S.D. columns give the standard deviation for the 6 replicates for each of the various vector constructs tested.

TABLE 1

| | Results | | | | | | | |
|---|---|---|---|---|---|---|---|---|
| | CSR:T1R2/ CSR:T1R3 | | hCaSR | | T1R2/ T1R3 | | Neg. control (mock transfection) | |
| | AVG | S.D. | AVG | S.D. | AVG | S.D. | AVG | S.D. |
| Positive control (Calcium) | 3912 | 295 | 7610 | 1776 | 1361 | 426 | 1570 | 509 |
| Aspartame | 72 | 78 | 41 | 97 | 531 | 154 | −125 | 116 |
| Sucralose | −75 | 130 | 22 | 92 | 601 | 173 | −186 | 36 |
| Perillartine | 2400 | 466 | 73 | 354 | 1840 | 333 | −379 | 327 |
| Cinnamonitrile | 1501 | 194 | 197 | 33 | 632 | 484 | −998 | 36 |
| Cyclamate | 370 | 213 | 196 | 79 | 341 | 132 | −324 | 297 |
| NDHC | 631 | 233 | −257 | 53 | 331 | 129 | −524 | 44 |
| Negative control (C1 buffer) | −115 | 70 | 57 | 101 | −63 | 131 | −217 | 204 |

The negative control/mock transfection shows the signal level corresponding to background signals.

As the positive control (calcium) shows, all transfected cells which have a calcium-sensing domain react to calcium (CSR:T1R2/CSR:T1R3 heterodimer and hCaCSR). The response of the chimeric heterodimer to calcium cannot be compared to those obtained with the sweet heterodimer. Since calcium is not an agonist of the T1R2/T1R3 sweet heterodimer it did not give signals that were greater than mock transfected cells expressing only the Gα16gust44 G-protein.

For aspartame and sucralose, a signal is detected only in the cells transfected with the T1R2/T1R3 heterodimer. This is expected because sucralose and aspartame are believed to bind in the VFT of T1R2, which is absent from the CSR:T1R chimera.

The hCaSR responded only to calcium chloride and could not be activated by any of the sweet tastants tested. For calcium chloride, perillartine, cinnamonitrile, cyclamate and NDHC, a significant increase of the signal was observed in cells expressing the CSR:T1R2/CSR:T1R3 chimeric heterodimer. For perillartine, cinnamonitrile, cyclamate, and NDHC these signals were comparable in intensity to the signal detected for the T1R2/T1R3 heterodimer.

The signals detected in the cells transfected with the chimeric CSR:T1R2/CSR:T1R3 heterodimer were significantly higher than the background obtained in the negative control (mock transfected HEK293T/Gα16-gustducin 44 cells).

The results demonstrate that CSR:T1R2/CSR:T1R3 is activated by calcium, perillartine, cyclamate, cinnamonitrile, naringin dihydrochalcone (NarDHC) and neohesperidin dihydrochalcone (NDHC) but not by sucralose or aspartame. Cyclamate activates the chimeric dimer but not T1R2-TMD, indicating that it requires the T1R3 transmembrane domain for activity. This is consistent with findings in the literature indicating that cyclamate binds in the T1R3 transmembrane domain. The dihydrochalcones appear to have binding sites in both transmembrane domains, based on data from the cell lines.

12B. Preparation of Stable Cell Lines Expressing the CSR:T1R2/CSR:T1R3 Heterodimer A stable cell line was generated in which CSR:T1R3 was constitutively over-expressed in the presence of a tetracycline-regulated CSR:T1R2 to avoid possible cytotoxic effects of constitutive over-expression of both proteins. DNA encoding one subunit of the heterodimer (CSR:T1R2) was placed in a tetracycline-regulated vector to allow regulation of its expression level so that viability and functionality of the stable clonal lines can be optimised.

In sum, human cell lines that stably express the chimeric human CSR:T1R2/CSR:T1R3 heterodimer were generated sequentially by first transfecting a linearized pcDNA4-TO vector (Invitrogen) containing the human CSR:T1R2 into a Gα16gust44 expressing cell line, which was prepared as described in WO 2004/055048. The Gα16gust44 expressing cell line shows enhanced coupling to taste receptors, is tetracycline inducible, stably expresses the Gα16gust44 promiscuous G-protein, and is based on the HEK-293-T-Rex cell line (commercially available from Invitrogen, USA). A clonal cell line expressing CSR:T1R2 was identified and transfected with a linearized pcDNA3.1-Hygro vector (Invitrogen) containing human CSR:T1R3 cDNA to obtain a double stable clonal cell line that expresses both CSR:T1R2 and CSR:T1R3.

24 hours after transfection with 4 micrograms of the linearized CSR:T1R2/pcDNA4TO construct and 0.3 µl of Lipofectamine 2000 (Invitrogen), cells were re-plated at 10× dilutions up to 1:150,000 in selective medium containing DMEM (Invitrogen) supplemented with 10% FBS, 0.005 mg/ml blasticidin, 0.36 mg/ml G418, and 0.2 mg/ml Zeocin at 37° C. After 2-3 weeks, Zeocin-resistant colonies were individually expanded and stable clones were selected based on a functional response to 50 micromolar perillartine following a four hour induction with 10 µg/ml tetracycline to allow for expression of the CSR:T1R2 cDNA. We identified an individual clone (#17) that exhibited minimal basal expression of the CSR:T1R2 cDNA and used this as a recipient for the CSR:T1R3 construct to generate a stable cell line for the heterodimeric receptor complex. Clone 17 containing the inducible CSR:T1R2 was transfected with 4 µg of the linearized CSR:T1R3/pcDNA3.1-Hygro vector construct DNA and 0.3 µl of Lipofectamine 2000 (Invitrogen). The lipofectamine/DNA mixture was incubated on the cells for 3-4 hours and then replaced with an antibiotic-free, serum-containing growth medium. After 24 hours the cells were re-plated in selective medium containing DMEM supplemented with 10% FBS, 0.005 mg/ml blasticidin, 0.36 mg/ml G418, 0.2 mg/ml zeocin, and 0.2 mg/ml hygromycin at 37° C.

Resistant colonies were expanded, and identified as containing the CSR:T1R2/CSR:T1R3 heterodimer on the basis of a response to both perillartine (contributed by binding/activation of CSR:T1R2) and to sodium cyclamate (contributed by binding/activation of CSR:T1R3), which was determined via automated fluorimetric imaging on the FLIPR-Tetra instrumentation (Molecular Devices) using the methods described in example 1. All potential clones were evaluated for a functional response to sweet tastants following induction with 10 µg/ml tetracycline (to induce over-expression of CSR:T1R2). Potential clones were also tested in the absence of tetracycline induction to identify any clones that basally express T1R2 at a low level, but have sufficient expression of the CSR:T1R2 receptor to allow for assembly with CSR:T1R3 resulting in a functional heterodimer complex (the tetracycline-regulated systems such as the T-Rex HEK-293 (Invitrogen) are known to have a low-level basal expression of transgenes due to the inherent leakiness of the system). Stable clones expressing an inducible functional CSR:T1R2/CSR:T1R3 heterodimer were identified on the basis of a response to both 50 micromolar perillartine and to 5 mM sodium cyclamate. One clonal cell line exhibiting the greatest tetracycline-inducible response to multiple sweet tastants was propagated and used for subsequent comparisons.

| Ligand | Ligand Concentration | CSR:T1R2/CSR:T1R3 AVG (dF/F) | CSR:T1R2/CSR:T1R3 S.D. (dF/F) | T1R2/T1R3 AVG (dF/F) | T1R2/T1R3 S.D. (dF/F) | G16gust44 (NEG. CONTROL) AVG (dF/F) | G16gust44 (NEG. CONTROL) S.D. (dF/F) |
|---|---|---|---|---|---|---|---|
| p-ETBZ | 100 micromolar | 1.113128 | 0.046279 | 1.029416 | 0.096094 | 0.159246 | 0.012781 |
| NDHC | 1 mM | 1.635446 | 0.234197 | 1.709872 | 0.052748 | 0.23042 | 0.013033 |
| NarDHC | 1 mM | 1.426728 | 0.226271 | 1.401695 | 0.146196 | 0.220575 | 0.074507 |
| CYCLAMATE | 5 mM | 1.275038 | 0.063317 | 1.596996 | 0.074684 | 0.174427 | 0.057165 |

Data indicates the normalized increase in fluorescence over baseline after stimulation ($\Delta F/F$) using the following equation: $\neq F/F = (F-F_0)/F_0$, where F is the peak fluorescence signal and $F_0$ is the baseline fluorescence signal, which is determined from the average fluorescence signal measured prior to ligand addition. The ΔF/F value obtained corresponds to the calcium increase of the cell in response to a direct or indirect interaction with the transfected receptor ("signal") (the mean (AVG) and standard deviation (S.D.) of three replicate experiments is given).

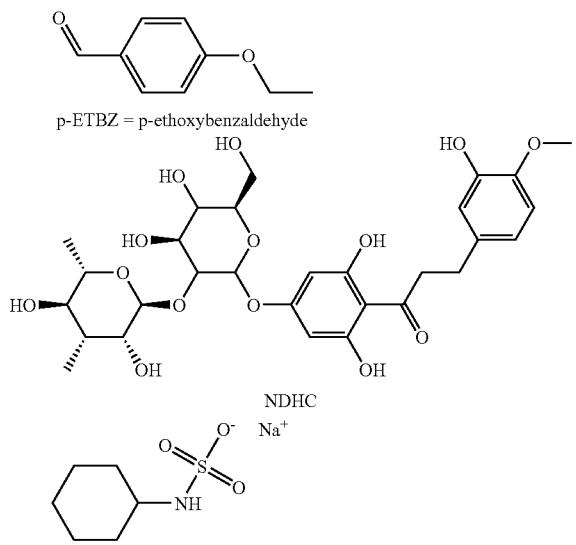

Sodium Cyclamate (sodium ion improves water solubility, doesn't contribute to sweet taste)

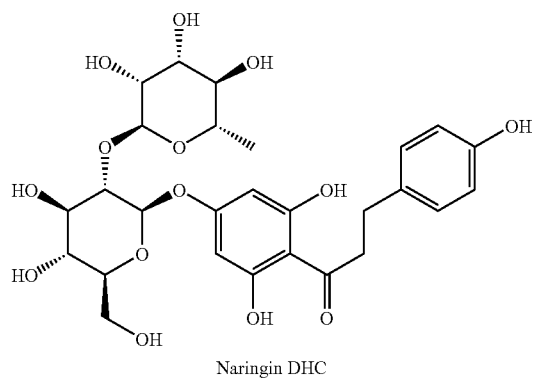

Naringin DHC

By methods analogous to those outlined in examples 12A or 12B assays are carried out using CSR:T1R2/T1R3 or T1R2/CSR:T1R3 heterodimers. In either case the CSR:T1R2 and CSR:T1R3 monomer constructs are created as described in examples 3 and 4 above respectively. The wildtype T1R2 or T1R3 monomer is created as described in example 5 above. Cells that express one of these other heterodimers can then be created by methods analogous to those for the preparation of the CSR:T1R2/CSR:T1R3 heterodimer-expressing cells described in example 12B and elsewhere above. The resultant cell lines express a wildtype VFT domain and can be used to perform assays as described in example 1, including assays for the activity of T1R2/T1R3 transmembrane domain binders in combination with themselves and with VFT domain binders.

Further assays are carried out by methods analogous to those in examples 12A and 12B include creating CSR:T1R2/T1R3-TMD and T1R2-TMD/CSR:T1R3 heterodimer-expressing cell lines. In either case the CSR:T1R2 and CSR:T1R3 monomer constructs are created as described in examples 3 and 4 above respectively. The truncated receptor vector constructs that direct expression of T1R2-TMD or T1R3-TMD are created by methods analogous to those set forth in example 2. The heterodimer-expressing cell lines can then be created by methods analogous to those described in examples 7 and 12B and elsewhere above. The resultant cell line expresses a heterodimer that contains a single CSR extra-cellular domain and can be used to perform assays as described in example 1.

Additionally, assays are carried out by the methods described in examples 12A and 12B for the receptor activity produced by combining two or more agents that bind to the transmembrane domain of the taste receptor. Alternatively methods analogous to those described in examples 12A and 12B can be used to test for receptor activity produced by combining a candidate sweetness enhancer with a ligand for the calcium-sensing receptor. Methods analogous to those for the creation of the CSR:T1R2 or CSR:T1R3 receptors (examples 3 and 4) can be used to create chimeric receptors using alternative class C GPCR extra-cellular domains. These alternative chimeric receptors can then be used in tests similar to those disclosed here. The alternative chimeric receptors include extra-cellular domains from other Class C GPCRs such as metabotropic glutamate receptors (mGluRs), GPRC-type receptors (i.e GPRC5 and GPRC6a), V2R pheromone receptors, and GABA-B receptors.

13. Ranking Tests to Determine the Sweetness Isointensity of Sweetness Enhancers to Sucrose Solutions For comparative ranking, samples of 0.5%, 1%, 1.5%, 7%, 8%, 9%, 10% and 11% sucrose solutions were prepared.

a) Sweetness Isointensity of Sweetness Enhancer in Sucrose Solutions

The sensory evaluation was conducted using a ranking method. Samples at ambient temperature were randomly presented in 15 ml blind aliquots (unidentifiable by panelists). Panels consisted of 10 sweet sensitive subjects and samples were presented in 3 replications over 1 session. After tasting each sample, the mouth was rinsed thoroughly with water at ambient temperature prior to tasting the next sample. Panelists were presented with 7%, 8%, 9%, 10%, 11% sucrose samples and a sixth sample of 7% sucrose with a sweetness enhancer in a concentration near its sweetness detection threshold. They were asked to rank the samples from low to high with respect to perceived sweet taste. R-indices (see below) were calculated for 7% sucrose with the sweetness enhancer versus 7%, 8%, 9%, 10% or 11% sucrose.

b) Near Threshold Sweetness Isointensity of Sweetness Enhancer in Water

The sensory evaluation was conducted using a ranking method. Samples at ambient temperature were randomly presented in 15 ml blind aliquots (unidentifiable by panelists). Panels consisted of 10 sweet sensitive subjects and samples were presented in 3 replications over 1 session. After tasting each sample, the mouth was rinsed thoroughly with water at ambient temperature prior to tasting the next sample. Panelists were presented with either 0.5% and 1% sucrose or 1% and 1.5% sucrose and a third sample of water with a sweetness enhancer in a concentration near its sweetness detection threshold. They were asked to rank the samples from low to high with respect to perceived sweet taste. R-indices were calculated for the sweetness enhancer in water versus either 0.5% and 1% sucrose or 1% and 1.5% sucrose. The R-index is a statistic obtained by an analytical procedure based on signal detection and is a short-cut method for determining the proportion of subjects choosing one sample over another (see O'Mahony, 1992, *J. Sens. Stud.,* 7:1-47). From ranking-style sensory tests, a matrix of responses (see table X below) is constructed such that each cell contains the number of times a given sample was ranked at a particular location.

TABLE X

|  | Position 1 (least sweet) | Position 2 | Position 3 (most sweet) |
| --- | --- | --- | --- |
| Sample X | A | B | C |
| Sample Y | D | E | F |
| Sample Z | G | H | I |

From this matrix, the R-index can be calculated according to the following equation:

$$R\text{-index}(X \text{ vs. } Y) = \frac{A(E+F) + B(F) + 0.5((A*D) + (B*E) + (C*F))}{(A+B+C)*(D+E+F)}$$

Essentially, the R-index is a measure of difference between two samples. The R-index has a chance level of detection of 50%. Thus, when comparing two samples, the derived R-index must be significantly different from 50% in order for them to be considered different. The critical value is the statistically relevant value that the derived R-index must deviate from (i.e greater or less than) in order to be considered significant.

An R-index greater than the higher critical value means that the sweetness enhancer sample is significantly sweeter than the sucrose sample. An R-index not significantly different from the critical value means that the sweetness enhancer sample has an equivalent sweetness to the compared sucrose sample. An R-index below the lower critical value indicates that the sucrose sample is sweeter than the sweetness enhancer sample.

14. Ranking Test of 150 ppm, 200 ppm, 250 ppm Cyclamate in Waters Determining its Sucrose Isointensity Aqueous mixtures containing either 150 ppm, 200 ppm or 250 ppm cyclamate in water were evaluated for isointensity to a 0.5% sucrose solution using a modified version of the ranking method described in example 13 (cyclamate concentration was varied, otherwise the procedures remain the same). The results are presented in the table below.

| cyclamate solution [ppm] | sample sweetness (0.5% sucrose) | R-index [%] | Critical value [%] | p-value |
| --- | --- | --- | --- | --- |
| 150 | isosweet | 41% | 35.39 | P > 0.05 |
| 200 | less sweet | 0% | 35.39 | P < 0.05 |
| 250 | less sweet | 0% | 35.39 | P < 0.05 |

An R-index of 41%, which is not significantly different than chance based on the lower critical value (35.39%), means that the 150 ppm cyclamate sample is isosweet to 0.5% sucrose. An R-index of 0%, which is below the critical value (35.39%), means that both the 200 ppm and 250 ppm cyclamate samples are significantly sweeter than 0.5% sucrose.

15. Ranking Test of 250 ppm Cyclamate in Water, Determining its Sucrose Isointensity A 250 ppm cyclamate in water sample was evaluated for isointensity to sucrose solutions in a concentration of 0.5-1% using the ranking method described in example 13. The results are presented in the table below.

| sucrose solutions [% wt/wt] | sample sweetness (cyclamate, 250 ppm) | R-index [%] | Critical value [%] | p-value |
| --- | --- | --- | --- | --- |
| 0.5% | sweeter | 89% | 64.61 | P < 0.05 |
| 1% | less sweet | 12% | 35.39 | P < 0.05 |

An R-index of 89%, which is above the critical value (64.61%), means that the cyclamate sample was sweeter than 0.5% sucrose. An R-index of 12%, which is below the critical value (35.39%), means the cyclamate sample was significantly less sweet than 1% sucrose. By interpolation, the sweetness of 250 ppm cyclamate was equivalent to about 0.75% sucrose.

16. Ranking Test of 1700-2500 ppm Cyclamate in Waters Determining Levels of Discrimination for Sweetness Solutions of 1700 ppm, 1900 ppm, 2100 ppm, 2300 ppm and 2500 ppm cyclamate in water were ranked for sweetness using a modified version of the method in example 13 (cyclamate used as the suprathreshold sweetener). Subjects were presented five samples containing 1700-2500 ppm cyclamate and asked to rank from the least sweet to the sweetest. The results are presented in the table below.

| cyclamate solution A [ppm] | sweetness A versus B | cyclamate solution B [ppm] | R-index [%] | Critical value [%] | p-value |
| --- | --- | --- | --- | --- | --- |
| 1700 | less sweet than | 1900 | 90% | 64.61 | P < 0.05 |
| 1900 | less sweet than | 2100 | 81% | 64.61 | P < 0.05 |
| 2100 | less sweet than | 2300 | 76% | 64.61 | P < 0.05 |
| 2300 | less sweet than | 2500 | 76% | 64.61 | P < 0.05 |

An R-index 90%, which is above the critical value (64.61%), means that the subjects could distinguish the sweetness of 1700 ppm cyclamate from 1900 ppm cyclamate. An R-index 81%, which is above the critical value (64.61%), means that the subjects could distinguish the sweetness of 1900 ppm cyclamate from 2100 ppm cyclamate. An R-index 76%, which is above the critical value (64.61%), means that the subjects could distinguish the sweetness of 2100 ppm cyclamate from 2300 ppm cyclamate. An R-index 76%, which is above the critical value (64.61%), means that the subjects could distinguish the sweetness of 2300 ppm cyclamate from 2500 ppm cyclamate. Based on these results, panelists could reliably discriminate the five cyclamate concentrations from one another.

17. Ranking Test of 75 ppm p-ethoxybenzaldehyde in Water, Determining its Sucrose Isointensity A 75 ppm p-ethoxybenzaldehyde in water sample was evaluated for isointensity to sucrose solutions in a concentration of 0.5-1% using the ranking method described in example 13. Subjects were required to wear nose clips to remove aroma effects on sweetness. The results are presented in the table below.

| sucrose solutions [% wt/wt] | sample sweetness (p-ethoxybenzaldehyde, 75 ppm) | R-index [%] | Critical value [%] | p-value |
| --- | --- | --- | --- | --- |
| 0.5% | less sweet | 7% | 35.39 | P < 0.05 |
| 1% | less sweet | 0% | 35.39 | P < 0.05 |

An R-index 0% or 7%, which is below the critical value (35.39%), means that the p-ethoxybenzaldehyde sample was less sweet than 0.5% sucrose. By interpolation, the sweetness of 75 ppm p-ethoxybenzaldehyde was equivalent in sweetness to 0.25% sucrose, or below the detection threshold for sweet.

18. Ranking Test of 0.5% Sucrose in Waters Determining its p-ethoxybenzaldehyde Isointensity A 0.5% sucrose solution in water was evaluated for isointensity to p-ethoxybenzaldehyde solutions at concentrations of 100 ppm and 150 ppm using a modified version of the ranking method described in example 13 (modified as for example 14 but with p-ethoxybenzaldehyde concentration varied). Subjects were required to wear nose clips to remove aroma effects on sweetness. The results are presented in the table below.

| p-ethoxybenzaldehyde solutions [ppm] | sample sweetness (0.5% sucrose) | R-index [%] | Critical value [%] | p-value |
|---|---|---|---|---|
| 100 | isosweet | 63% | 64.61 | P > 0.05 |
| 150 | less sweet | 3% | 35.39 | P < 0.05 |

An R-index of 63%, which is within the critical value range (35.39-64.61%), is not significantly different from chance and indicates that the 0.5% sucrose solution was isointense to an aqueous solution of 100 ppm p-ethoxybenzaldehyde. An R-index of 3%, which is below the critical value (35.39%), means the solution of 0.5% sucrose was significantly less sweet than an aqueous solution of 150 ppm p-ethoxybenzaldehyde.

19. Ranking Test of 600-1000 ppm p-ethoxybenzaldehyde in Waters Determining Levels of Discrimination for Sweetness Solutions of 600 ppm, 700 ppm, 800 ppm, 900 ppm and 1000 ppm p-ethoxybenzaldehyde in water were ranked for sweetness using a modified version of the method in example 13 (using p-ethoxybenzaldehyde as the suprathreshold sweetener not sucrose). Subjects were presented five samples containing 600 ppm-1000 ppm p-ethoxybenzaldehyde and asked to rank the samples from the least sweet to the sweetest. Subjects were required to wear nose clips to remove aroma effects on sweetness. The results are presented in the table below.

| p-ethoxybenzaldehyde solution A [ppm] | sweetness A versus B | p-ethoxybenzaldehyde solution B [ppm] | R-index [%] | Critical value [%] | p-value |
|---|---|---|---|---|---|
| 600 | less sweet than | 700 | 74% | 64.61 | P < 0.05 |
| 700 | less sweet than | 800 | 72% | 64.61 | P < 0.05 |
| 800 | less sweet than | 900 | 67% | 64.61 | P < 0.05 |
| 900 | less sweet than | 1000 | 73% | 64.61 | P < 0.05 |

An R-index 74%, which is above the critical value (64.61%), means that the subjects could distinguish the sweetness of 600 ppm p-ethoxybenzaldehyde from 700 ppm p-ethoxybenzaldehyde. An R-index 72%, which is above the critical value (64.61%), means that the subjects could distinguish the sweetness of 700 ppm p-ethoxybenzaldehyde from 800 ppm p-ethoxybenzaldehyde. An R-index 67%, which is above the critical value (64.61%), means that the subjects could distinguish the sweetness of 800 ppm p-ethoxybenzaldehyde from 900 ppm p-ethoxybenzaldehyde. An R-index 73%, which is above the critical value (64.61%), means that the subjects could distinguish the sweetness of 900 ppm p-ethoxybenzaldehyde from 1000 ppm p-ethoxybenzaldehyde. These results indicate that the panelists could reliably discriminate the five p-ethoxybenzaldehyde concentrations from one another.

20. Ranking Test of 100 ppm p-ethoxybenzaldehyde in Waters Determining its Cyclamate Isointensity A 100 ppm p-ethoxybenzaldehyde in water sample was evaluated for isointensity to cyclamate solutions in a concentration of 150-250 ppm using a modified version of the ranking method described in example 13 (cyclamate concentration varied to calculate isointensity against p-ethoxybenzaldehyde). Subjects were required to wear nose clips to remove aroma effects on sweetness. The results are presented in the table below.

| cyclamate solutions [ppm] | sample sweetness (p-ethoxybenzaldehyde, 100 ppm) | R-index [%] | Critical value [%] | p-value |
|---|---|---|---|---|
| 150 | isosweet | 51% | 64.61 | P > 0.05 |
| 200 | less sweet | 17% | 35.39 | P < 0.05 |
| 250 | less sweet | 5% | 35.39 | P < 0.05 |

An R-index of 51%, which is within the critical value range (35.39-64.61%), means that the p-ethoxybenzaldehyde sample is isosweet with 150 ppm cyclamate. An R-index of 5% and 17%, which are below the critical value (35.39%), means the p-ethoxybenzaldehyde sample was less sweet than either 200 ppm or 250 ppm cyclamate.

21. Ranking Test of 250 ppm Cyclamate in 7% Sucrose, Determining its Sucrose Isointensity A 250 ppm cyclamate in 7% sucrose sample was evaluated for its isointensity to sucrose solutions in a concentration of 7-11% using the ranking method described in example 13. The results are presented in the table below.

| sucrose solution [% wt/wt] | cyclamate sample sweetness | R-index [%] | Critical value [%] | p-value |
|---|---|---|---|---|
| 7% | sweeter | 96% | 64.61 | P < 0.05 |
| 8% | sweeter | 80% | 64.61 | P < 0.05 |

-continued

| sucrose solution [% wt/wt] | cyclamate sample sweetness | R-index [%] | Critical value [%] | p-value |
|---|---|---|---|---|
| 9% | isosweet | 38% | 35.39 | P > 0.05 |
| 10% | less sweet | 24% | 35.39 | P < 0.05 |
| 11% | less sweet | 0% | 35.39 | P < 0.05 |

An R-index of 80% and 96%, which are greater than the critical value (64.61%), means that the cyclamate in 7% sucrose sample was significantly sweeter than the sucrose sample at 7% or 8%. An R-index of 38%, which is within the critical value range (35.39-64.61%), is equivalent to chance meaning the cyclamate sample was isosweet to 9% sucrose. The R-index between 0% and 24%, which was below the critical value (35.39%), means the cyclamate sample was less sweet than either 10% or 11% sucrose. Accordingly, 250 ppm cyclamate in 7% sucrose adds 2° Brix of sucrose sweetness intensity to enhance the sweetness to the equivalent of a 9% sucrose solution. The 7% sucrose+250 ppm cyclamate (250 ppm cyclamate is isosweet to 0.75% sucrose, see example 15) would be expected to be equivalent in sweetness to sucrose of from above 7.5% to below 8%, interpolated to 7.75% sucrose, if the effect were merely additive. However, as shown above, the combination of 250 ppm cyclamate with 7% sucrose had a sweetness isointensity to 9% sucrose, clearly greater than the expected effect.

22. Ranking Test of 0.5% Sucrose in 1700 ppm Cyclamate, Determining its Cyclamate Isointensity A 0.5% sucrose in 1700 ppm cyclamate sample was evaluated for its isointensity to cyclamate solutions in a concentration of 1700-2500 ppm using a modified version of the ranking method described in example 13 (cyclamate used as the suprathreshold sweetener). The results are presented in the table below.

| cyclamate solution [ppm] | sucrose sample sweetness | R-index [%] | Critical value [%] | p-value |
|---|---|---|---|---|
| 1700 | sweeter | 85% | 64.61 | P < 0.05 |
| 1900 | isosweet | 60% | 64.61 | P > 0.05 |
| 2100 | less sweet | 21% | 35.39 | P < 0.05 |
| 2300 | less sweet | 7% | 35.39 | P < 0.05 |
| 2500 | less sweet | 4% | 35.39 | P < 0.05 |

An R-index of 85%, which is greater than the critical value (64.61%), means that the sucrose in 1700 ppm cyclamate sample was significantly sweeter than the cyclamate sample at 1700 ppm. An R-index of 60%, which is within the critical value range (35.39-64.61%), is equivalent to chance meaning the sucrose sample was isosweet to 1900 ppm cyclamate. The R-index between 4% and 21%, which is below the critical value (35.39%), means the sucrose sample is less sweet than either 2100 ppm, 2300 ppm and 2500 ppm cyclamate. Accordingly, 0.5% sucrose in 1700 ppm cyclamate adds an equivalent of 200 ppm cyclamate in sweetness to the sample (i.e. 1700 ppm cyclamate+0.5% sucrose=1900 ppm cyclamate). This equivalence is further substantiated by the results of comparing the sweetness of 0.5% sucrose in water to 150 ppm cyclamate (see example 14). Accordingly, the 1700 ppm cyclamate+0.5% sucrose would be expected to be equivalent in sweetness to 1850 ppm cyclamate.

The detection threshold of the sweet sensitive panelists was 200 ppm cyclamate when cyclamate is used at a suprathreshold level for sweet (see example 16). Panelists would not be expected to discriminate between 1850 ppm cyclamate and 1900 ppm cyclamate. In sum, the data indicate that the effect of sucrose on cyclamate sweetness was merely additive.

23. Ranking Test of 100 ppm p-ethoxybenzaldehyde in 1700 ppm Cyclamate, Determining its Cyclamate Isointensity.

A 100 ppm p-ethoxybenzaldehyde in 1700 ppm cyclamate sample was evaluated for its isointensity to cyclamate solutions in a concentration of 1700-2500 ppm using a modified version of the ranking method described in example 13. Subjects were required to wear nose clips to prevent aroma from affecting the results. The results are presented in the table below.

| cyclamate solution [ppm] | p-ethoxybenzaldehyde sample sweetness | R-index [%] | Critical value [%] | p-value |
|---|---|---|---|---|
| 1700 | sweeter | 87% | 64.84 | P < 0.05 |
| 1900 | sweeter | 80% | 64.84 | P < 0.05 |
| 2100 | isosweet | 50% | 64.84 | P > 0.05 |
| 2300 | less sweet | 22% | 35.16 | P < 0.05 |
| 2500 | less sweet | 17% | 35.16 | P < 0.05 |

R-indexes of 80% and 87%, which are greater than the critical value (64.61%), indicate that the p-ethoxybenzaldehyde sample was significantly sweeter than the cyclamate sample at 1700 ppm and 1900 ppm. An R-index of 50%, which is within the critical value range (35.16-64.84%), is equivalent to chance meaning the p-ethoxybenzaldehyde sample was isosweet to 2100 ppm cyclamate. The R-index between 17% and 22%, which is below the critical value (35.16%), means the p-ethoxybenzaldehyde sample was less sweet than either 2300 ppm or 2500 ppm cyclamate. Accordingly, 100 ppm p-ethoxybenzaldehyde adds an equivalent of 400 ppm cyclamate in sweetness to 1700 ppm cyclamate (i.e. 1700 ppm cyclamate+100 ppm p-ethoxybenzaldehyde=2100 ppm cyclamate). By comparison of 100 ppm p-ethoxybenzaldehyde in water to 150 ppm cyclamate (see example 20), 1700 ppm cyclamate+100 ppm p-ethoxybenzaldehyde would be expected to be equivalent in sweetness to 1850 ppm cyclamate.

However, as shown above, a mixture of 100 ppm p-ethoxybenzaldehyde with 1700 ppm cyclamate was isosweet to 2100 ppm cyclamate, clearly greater than the expected effect indicating the effect was not merely additive.

24. Ranking Test of 75 ppm p-ethoxybenzaldehyde in 7% Sucrose, Determining its Sucrose Isointensity A 75 ppm p-ethoxybenzaldehyde in 7% sucrose sample was evaluated for isointensity to sucrose solutions in a concentration of 7-11% using the ranking method described in example 13. Subjects were required to wear nose clips to prevent aroma from affecting the results. The results are presented in the table below.

| Sucrose solution [% wt/wt] | p-ethoxybenzaldehyde sample sweetness | R-index [%] | Critical value [%] | p-value |
|---|---|---|---|---|
| 7% | sweeter | 74% | 64.61% | P < 0.05 |
| 8% | isosweet | 36% | 35.39% | P > 0.05 |
| 9% | less sweet | 12% | 35.39% | P < 0.05 |
| 10% | less sweet | 1% | 35.39% | P < 0.05 |
| 11% | less sweet | 0% | 35.39% | P < 0.05 |

An R-index of 74%, which is greater than the higher critical value (64.61%), means that the 75 ppm p-ethoxybenzaldehyde sample was significantly sweeter than 7% sucrose. An R-index of 36%, which is within the critical value range (35.39-64.61%), is equivalent to chance meaning that the p-ethoxybenzaldehyde sample had an equivalent sweetness to 8% sucrose. An R-index of 0%, 1% and 12% which is below the lower critical value (35.39%) indicates that the sucrose samples were sweeter than the p-ethoxybenzaldehyde sample. The data shows that the perceived sweetness of a mixture of 7% sucrose and 75 ppm p-ethoxybenzaldehyde was isosweet to 8% sucrose. By comparison, 75 ppm p-ethoxybenzaldehyde in water had an isointensity of below 0.5% sucrose (see example 17). The 7% sucrose+75 ppm p-ethoxybenzaldehyde sample therefore would be expected to be equivalent in sweetness to less than 7.5% sucrose, interpolated to 7.25% sucrose, if the effect were merely additive (following example 17). However, as shown above, the combination of 75 ppm p-ethoxybenzaldehyde with 7% sucrose was isosweet to 8% sucrose, clearly greater than the expected effect.

25. Ranking Test of 250 ppm Cyclamate and 75 ppm p-ethoxybenzaldehyde in 7% Sucrose, Determining the Sucrose Isointensity A mixture of 250 ppm cyclamate and 75 ppm p-ethoxybenzaldehyde in 7% sucrose sample was evaluated for its isointensity to sucrose solutions at concentrations of 7-11% using the ranking method described in example 13. Subjects were required to wear nose clips to prevent aroma from affecting the results. The results are presented in the table below.

| sucrose solution [% wt/wt] | mixture sample sweetness | R-index [%] | Critical value [%] | p-value |
|---|---|---|---|---|
| 7% | sweeter | 98% | 64.61 | P < 0.05 |
| 8% | sweeter | 93% | 64.61 | P < 0.05 |
| 9% | sweeter | 74% | 64.61 | P < 0.05 |
| 10% | less sweet | 29% | 35.39 | P < 0.05 |
| 11% | less sweet | 12% | 35.39 | P < 0.05 |

R-indexes of 74-98% are higher than the higher critical value (64.61%), indicating that the cyclamate/p-ethoxybenzaldehyde mixture sample was sweeter than 7%, 8% and 9% sucrose. R-indexes of 12% to 29% are below the critical value (35.39%), indicating that the cyclamate/p-ethoxybenzaldehyde sample was less sweet than 10% or 11% sucrose. The data shows that the perceived sweetness of 7% sucrose with 250 ppm cyclamate and 75 ppm p-ethoxybenzaldehyde was significantly higher than the sweetness of 9% sucrose but below the sweetness of 10% sucrose, or 9.5% by interpolation.

By comparison, 250 ppm cyclamate in water was isosweet to above 0.5% sucrose but below 1% sucrose, interpolated to 0.75% (see examples 14 and 15), and 75 ppm p-ethoxybenzaldehyde in water was isosweet to below 0.5% sucrose, interpolated to 0.25% (see example 17). Accordingly, the 7% sucrose+250 ppm cyclamate (isosweet to below 1% sucrose and above 0.5% sucrose, interpolated to 0.75% sucrose) and 75 ppm p-ethoxybenzaldehyde (isosweet to below 0.5% sucrose, interpolated to 0.25% sucrose), would be expected to be isosweet to below 8.5% sucrose, or 8% sucrose by interpolation. However, the determined isointensity was above 9% sucrose, interpolated to 9.5% sucrose, clearly above the expected effect.

26. Ranking Test of 100 ppm p-ethoxyvbenzaldehyde and 0.5% Sucrose in 1700 ppm Cyclamate, Determining the Cyclamate Isointensity A mixture of 100 ppm p-ethoxybenzaldehyde and 0.5% sucrose in 1700 ppm cyclamate sample was evaluated for its isointensity to cyclamate solutions in a concentration of 1700-2500 ppm using a modified version of the ranking method described in example 13. Subjects were required to wear nose clips to prevent aroma from affecting the results. The results are presented in the table below.

| cyclamate solution [ppm] | mixture sample sweetness | R-index [%] | Critical value [%] | p-value |
|---|---|---|---|---|
| 1700 | sweeter | 98% | 64.61 | P < 0.05 |
| 1900 | sweeter | 94% | 64.61 | P < 0.05 |
| 2100 | sweeter | 79% | 64.61 | P < 0.05 |
| 2300 | isosweet | 56% | 64.61 | P > 0.05 |
| 2500 | isosweet | 44% | 35.39 | P > 0.05 |

R-indexes of 79-98% are greater than the higher critical value (64.61%), indicating that the p-ethoxybenzaldehyde/sucrose mixture sample was sweeter than 1700 ppm, 1900 ppm and 2100 ppm cyclamate. An R-index of 56% is within the critical value range (35.39-64.61%), indicating that the p-ethoxybenzaldehyde/cyclamate sample was isosweet to 2300 ppm cyclamate. An R-index of 44%, which is equivalent to chance at the lower critical value (35.16%), means that the p-ethoxybenzaldehyde/cyclamate sample was isosweet to 2500 ppm cyclamate. The data shows that the perceived sweetness of 1700 ppm cyclamate with 100 ppm p-ethoxybenzaldehyde and 0.5% sucrose was significantly higher than the sweetness of 2100 ppm cyclamate but could not be discriminated from 2300 ppm and 2500 ppm cyclamate.

By comparison, 100 ppm p-ethoxybenzaldehyde in water was isosweet to 150 ppm cyclamate (see example 20) and 0.5% sucrose in water was isosweet to 150 ppm cyclamate (see example 14). Accordingly, the 1700 ppm cyclamate+100 ppm p-ethoxybenzaldehyde (isosweet to 150 ppm cyclamate) and 0.5% sucrose (isosweet 150 ppm cyclamate), would be expected to be isosweet to below 2100 ppm cyclamate, or 2000 ppm cyclamate. However, the determined isointensity was above 2100 ppm cyclamate, with an isointensity range between 2300 ppm and 2500 ppm cyclamate, clearly above the expected (additive) effect.

27. Ranking Test of 150 ppm Cyclamate in an Aqueous Solution of 600 ppm p-ethoxybenzaldehyde, Determining its p-ethoxybenzaldehyde Isointensity A mixture of 150 ppm cylamate in an aqueous solution of 600 ppm p-ethoxybenzaldehyde sample was evaluated for its isointensity to p-ethoxybenzaldehyde solutions in a concentration of 600 ppm and 700 ppm using a modified version of the ranking method described in example 13. Subjects were required to wear nose clips to prevent aroma from affecting the results. The results are presented in the table below.

| p-ethoxybenzaldehyde solution [ppm] | mixture sample sweetness | R-index [%] | Critical value [%] | p-value |
|---|---|---|---|---|
| 600 | sweeter | 92% | 64.61 | P < 0.05 |
| 700 | sweeter | 70% | 64.61 | P < 0.05 |

R-indexes of 92% and 70% are greater than the critical value (64.84%), indicating that the 150 ppm cyclamate in an aqueous solution of 600 ppm p-ethoxybenzaldehyde is sweeter than 600 ppm and 700 ppm p-ethoxybenzaldehyde solutions alone.

By comparison, 150 ppm cyclamate in water is isosweet to 100 ppm p-ethoxybenzaldehyde in water (see example 20). The addition of 150 ppm cyclamate to an aqueous solution of 600 ppm p-ethoxybenzaldehyde should be isosweet to an aqueous solution of 700 ppm p-ethoxybenzaldehyde if the effect were merely additive. However, 150 ppm cyclamate in an aqueous solution of 600 ppm p-ethoxybenzaldehyde was found to be sweeter than 700 ppm p-ethoxybenzaldehyde, clearly above the expected effect.

28. Ranking Test of 0.5% Sucrose in an Aqueous Solution of 600 ppm p-ethoxybenzaldehyde, Determining its p-ethoxybenzaldehyde Isointensity A sample mixture of 0.5% sucrose and 600 ppm p-ethoxybenzaldehyde in an aqueous solution was evaluated for its isointensity to p-ethoxybenzaldehyde solutions at a concentration of 600 ppm and 700 ppm using a modified version of the ranking method described in example 13. Subjects were required to wear nose clips to prevent aroma from affecting the results. The results are presented in the table below.

| p-ethoxybenzaldehyde solution [ppm] | mixture sample sweetness | R-index [%] | Critical value [%] | p-value |
|---|---|---|---|---|
| 600 | sweeter | 68% | 64.61 | P < 0.05 |
| 700 | isosweet | 59% | 64.61 | P > 0.05 |

An R-index of 68%, which is greater than the critical value (64.61%), means that 0.5% sucrose in an aqueous solution of 600 ppm p-ethoxybenzaldehyde is sweeter than 600 ppm p-etthoxybenzaldehyde alone. An R-index of 59%, which is equivalent to chance at the higher critical value (64.61%), means that 0.5% sucrose in an aqueous solution of 600 ppm p-ethoxybenzaldehyde was isosweet to an aqueous solution of 700 ppm p-ethoxybenzaldehyde.

By comparison, 0.5% sucrose in water was isosweet to 100 ppm p-ethoxybenzaldehyde (see example 18). The addition of 0.5% sucrose to an aqueous solution of 600 ppm p-ethoxybenzaldehyde was not sweeter than an aqueous solution of 700 ppm p-ethoxybenzaldehyde, meaning the effect was merely additive.

29. Ranking Test of 150 ppm Cyclamate and 0.5% Sucrose in 600 ppm p-ethoxybenzaldehyde, Determining the p-ethoxybenzaldehyde Isointensity A sample mixture of 150 ppm cyclamate and 0.5% sucrose in 600 ppm p-ethoxybenzaldehyde was evaluated for its isointensity to p-ethoxybenzaldehyde solutions at a concentration of 600 ppm and 700 ppm using a modified version of the ranking method described in example 13. Subjects were required to wear nose clips to prevent aroma from affecting the results. The results are presented in the table below.

| p-ethoxybenzaldehyde solutions [ppm] | mixture sample sweetness | R-index [%] | Critical value [%] | p-value |
|---|---|---|---|---|
| 600 | sweeter | 96% | 64.61 | P < 0.05 |
| 700 | sweeter | 94% | 64.61 | P < 0.05 |

R-indexes of 94 and 96% are greater than the critical value (64.61%), indicating that the cyclamate/sucrose mixture sample was sweeter than 600 ppm and 700 ppm p-ethoxybenzaldehyde.

By comparison, 150 ppm cyclamate in water was isosweet to 100 ppm p-ethoxybenzaldehyde in water (see example 20) and 0.5% sucrose in water was isosweet to 100 ppm p-ethoxybenzaldehyde in water (see example 18). Accordingly, the 600 ppm p-ethoxybenzaldehyde in water plus 150 ppm cyclamate (isosweet to 100 ppm p-ethoxybenzaldehyde) and 0.5% sucrose (isosweet 100 ppm p-ethoxybenzaldehyde) would be expected to be isosweet to 800 ppm p-ethoxybenzaldehyde. The determined isointensity was above 700 ppm p-ethoxybenzaldehyde.

30. Ranking Test of 60 ppm NarDHC in Waters Determining its Sucrose Isointensity A 60 ppm NarDHC in water sample was evaluated for isointensity to sucrose solutions at a concentration of 0.5-1% using a modified version of the ranking method described in example 13. The results are presented in the table below.

| sucrose solution [% wt/wt] | sample sweetness (NarDHC, 60 ppm) | R-index [%] | Critical value [%] | p-value |
|---|---|---|---|---|
| 0.5% | sweeter | 99% | 64.61 | P < 0.05 |
| 1% | sweeter | 71% | 64.61 | P < 0.05 |
| 1.5% | less sweet | 20% | 35.39 | P < 0.05 |

R-indexes of 99% and 71% are above the critical value (64.61), indicating that the NarDHC sample was more sweet than 0.5% or 1% sucrose. An R-index of 20%, which is below the critical value (35.39%), means the NarDHC sample was significantly less sweet than 1.5% sucrose By interpolation, the sweetness of 60 ppm NarDHC was equivalent to about 1.25% sucrose.

31. Ranking Test of 2 ppm NDHC in Water, Determining its Sucrose Isointensity

A 2 ppm NDHC in water sample was evaluated for its isointensity to sucrose solutions at a concentration of 0.5-1% using the ranking method described in example 13. The results are presented in the table below.

| sucrose solutions [% wt/wt] | NDHC sample sweetness | R-index [%] | Critical value [%] | p-value |
|---|---|---|---|---|
| 0.5% | isosweet | 41% | 35.39 | P > 0.05 |
| 1% | less sweet | 5% | 35.39 | P < 0.05 |

An R-index of 41%, which is not significantly above the critical value (35.39%), means that the NDHC sample was isosweet to 0.5% sucrose. An R-index of 5%, which is below the critical value (35.39%), means the NDHC sample was significantly less sweet than 1% sucrose.

32. Paired Comparison of 45 ppm, 50 ppm, 55 ppm and 60 ppm NarDHC in Water Versus 0%, 0.5%, 1% or 1.5% Sucrose A NarDHC (45 ppm, 50 ppm, 55 ppm, 60 ppm) in water sample was evaluated for isointensity to sucrose solutions in a concentration of 0-1.5% using a modified version of the paired comparison method described in example 13. The NarDHC sample was compared to either 0%, 0.5%, 1% or 1.5% sucrose. The results are indicated in the table below.

| NarDHC [ppm] | Result of comparison | Sucrose [% wt/wt] |
| --- | --- | --- |
| 45 | weakly sweeter | 0 |
| 45 | isosweet | 0.5 |
| 45 | less sweet | 1 |
| 50 | notably sweeter | 0.5 |
| 50 | less sweet | 1 |
| 55 | notably sweeter | 0.5 |
| 55 | isosweet | 1 |
| 60 | notably sweeter | 1 |
| 60 | significantly less sweet | 1.5 |

The 45 ppm solution of NarDHC was weakly sweeter when compared to the 0% sucrose and isosweet to the sweetness of 0.5% sucrose. The 50 ppm NarDHC sample was notably sweeter than 0.5% sucrose but was found to be less sweet than 1% sucrose. The 55 ppm NarDHC sample was notably sweeter than 0.5% sucrose and determined to be isosweet to the sweetness of 1% sucrose. The 60 ppm NarDHC sample was notably sweeter than 1% sucrose but significantly less sweet than 1.5% sucrose.

33. Forced Choice Test of 60 ppm Swingle Extract in Water Versus 0%, 0.5% and 1% Sucrose A forced choice sensory evaluation of swingle extract as a sweetener was performed as described in example 13 (see also for forced choice method, O'Mahony, 1992, *J. Sens. Stud.*, 7:1-47), subject to the following modifications: Swingle extract had a concentration of 60 ppm in water and was compared to either 0% sucrose/water, 0.5% sucrose/water or 1% sucrose. The results are indicated in the tables below.

| comparison | Sucrose [% wt/wt] | Number panellists choosing swingle in water as sweeter | Number panellists choosing 0% or 1% sucrose as sweeter | Significance level (forced choice) |
| --- | --- | --- | --- | --- |
| 1 | 0 | 30/30 | 0/30 | p < 0.001 |
| 2 | 0.5 | 28/30 | 2/30 | p < 0.001 |
| 3 | 1 | 6/30 | 24/30 | p < 0.001 |

The 60 ppm swingle extract was close to the threshold concentration for its sweet perception and significantly less sweet than the weakly sweet 1% sucrose. The 60 ppm swingle sample in water was perceived as sweeter than 0% sucrose/water by all panelists (30 of 30 panelists, with a statistical significance level for the forced choice of p<0.001). The low sweetness intensity rating of 0.63 reflects the very weak perceivable sweetness (compare the 0% sucrose with a rating of 0.1. The highest imaginable sweetness rates as 10). The 60 ppm swingle sample in water was perceived as sweeter than 0.5% sucrose/water by a vast majority of the panelists (28 of 30 panelists, with a statistical significance level for the forced choice of p<0.001). The large majority of panelists (24 of 30) selected the weakly sweet 1% sucrose solution as being sweeter than the 60 ppm swingle extract solution with a statistical significance level for the forced choice of p<0.001. The low sweetness intensity rating of 0.58 for swingle extract in water versus 0.72 for 1% sucrose reflects the very weak perceivable sweetness of 60 ppm swingle which was significantly less than the sweetness of 1% sucrose. By interpolation, the sweetness of 60 ppm swingle extract was equivalent to about 0.75% sucrose.

34. Forced Choice Test of 60 ppm Swingle Extract+60 ppm NarDHC+2 ppm NDHC in Water Versus 2.25% Sucrose A forced choice test of a mixture of swingle extract, NarDHC, and NDHC was performed as described in example 13 subject to the following modifications: A 60 ppm swingle extract+60 ppm NarDHC+2 ppm NDHC in water sample was compared to 2.25% sucrose. The 2.25% sucrose concentration was selected to be slightly less than the interpolated added individual effects of the sweetness isointensities to sucrose of each sweetness enhancer: 0.5% for 2 ppm NDHC (example 31)+0.75% for 60 ppm swingle extract (example 33)+1.25% for 60 ppm NarDHC (examples 30 and 32). The 2 ppm NDHC+60 ppm swingle extract+60 ppm NarDHC was significantly less sweet than 2.25% sucrose, as shown in the table below. This result shows that the mixture of sweetness enhancers in water (without addition of sucrose) was below the summed-up sweetness of each ingredient. Further it is noted that the sweetness enhancers as such do not enhance each other's sweetness to any great extent.

| Sucrose [% wt/wt] | Number of panellists choosing sample as sweeter | Number of panellists choosing 2.25% sucrose as sweeter | Significance level (forced choice) |
| --- | --- | --- | --- |
| 2.25 | 9/30 | 21/30 | p = 0.023 |

35. Ranking Test of 60 ppm Swingle Extract and 2 ppm NDHC+in 7% Sucrose, Determining its Sucrose Isointensity.

A sample mixture of 60 ppm swingle extract+2 ppm NDHC in 7% sucrose sample was evaluated for isointensity to sucrose solutions in a concentration of 7-11% using the ranking method described in example 13. The results are indicated in the table below.

| Sucrose solutions [% wt/wt] | sample sweetness | R-index [%] | Critical value [%] | p-value |
| --- | --- | --- | --- | --- |
| 7% | Sweeter | 98% | 72.18 | P < 0.001 |
| 8% | sweeter | 82% | 72.18 | P < 0.001 |
| 9% | isosweet | 43% | 37.26 | P > 0.05 |
| 10% | less sweet | 12% | 27.82 | P < 0.001 |
| 11% | less sweet | 4% | 27.82 | P < 0.001 |

R-index values of 82 and 98% are greater than the critical value (72.18%), indicating that the NDHC+swingle sample was significantly sweeter than the sucrose sample at 7% or 8%. An R-index of 43%, which is not significantly different from chance, indicates that the NDHC+swingle sample was isosweet to 9% sucrose. An R-index of 4-12%, which is below the critical value (27.82%), indicates that the NDHC+swingle sample was significantly less sweet than 10% or 11% sucrose. The 2 ppm NDHC in water has a sweetness isointensity of 0.5% sucrose (see example 31). The 60 ppm swingle in water has a sweetness isointensity of above 0.5% but below 1% sucrose (0.75% by interpolation) (see example 33). Accordingly, the 7% sucrose+2 ppm NDHC (isotense to 0.5% sucrose)+60 ppm swingle extract (isosweet to below 1% sucrose, interpolated to 0.75% sucrose), would be expected to be isosweet to below 8.5% sucrose, or below 8.25% sucrose by interpolation. However, the determined isointensity was 9% sucrose, clearly above a merely additive effect.

36. Ranking Test of 60 ppm Swindle Extract+60 ppm NarDHC+2 ppm NDHC+in 7% Sucrose, Determining its Sucrose Isointensity.

A sample of 60 ppm swingle extract+60 ppm NarDHC+2 ppm NDHC in 7% sucrose was evaluated for sweetness isointensity to sucrose solutions in a concentration of 7-11% using the ranking method described in example 13. The results are indicated in the table below.

| Sucrose solution [% wt/wt] | sample sweetness | R-index [%] | Critical value [%] | p-value |
|---|---|---|---|---|
| 7% | sweeter | 100% | 74.89 | P < 0.001 |
| 8% | sweeter | 100% | 74.89 | P < 0.001 |
| 9% | sweeter | 90% | 74.89 | P < 0.001 |
| 10% | sweeter | 79% | 74.89 | P < 0.001 |
| 11% | isosweet | 48% | 74.89 | P > 0.001 |

R-index values of 79-100% are greater than the critical value (74.89%), indicating that the NDHC+swingle+ NarDHC sample was significantly sweeter than the sucrose sample at 7%, 8%, 9% and 10%. An R-index from 50% to the critical value (74.89%) would mean that the NDHC+swingle+NarDHC sample has an equivalent sweetness to the compared sucrose sample. At 48%, the NDHC+swingle+NarDHC sample was equivalent to 11% sucrose. By comparison, the 2 ppm NDHC in water had a sweetness isointensity to 0.5% sucrose (see example 31). The 60 ppm NarDHC in water had a sweetness isointensity to above 1% sucrose but below 1.5% sucrose, interpolated to 1.25% sucrose (see examples 30 and 32). The 60 ppm swingle in water had an isointensity of above 0.5% but below 1% sucrose, interpolated to 0.75% sucrose (see example 33). Accordingly, the 7% sucrose+2 ppm NDHC (isosweet to 0.5% sucrose)+60 ppm NarDHC (isotense to below 1.5% sucrose, interpolated to 1.25% sucrose)+60 ppm swingle extract (isosweet to below 1% sucrose, interpolated to 0.75% sucrose) would be expected to be isosweet to below 10% sucrose, or below 9.5% sucrose by interpolation, assuming an additive effect. Furthermore, 2 ppm NDHC+60 ppm swingle extract+60 ppm NarDHC in water was determined to be less sweet than 2.25% sucrose (see example 34) thus the isointensity of the mixture in 7% sucrose would be expected to be less than 9.25% sucrose, assuming an additive effect. However, the determined sweetness isointensity was an isointensity to 11% sucrose, which is clearly above a merely additive effect.

The invention claimed is:

1. A method of identifying a compound that binds to and/or activates a taste receptor outside the venus flytrap domain of the taste receptor comprising contacting a modified taste receptor with a compound and determining whether the compound binds to and/or activates the modified taste receptor, wherein the modified taste receptor comprises:
   a) T1R2-TMD (SEQ ID NO: 2), T1R3-TMD (SEQ ID NO: 28), both T1R2-TMD (SEQ ID NO: 2) and T1R3-TMD (SEQ ID NO: 28), CSR:T1R2 (SEQ ID NO: 14), CSR:T1R3 (SEQ ID NO: 16), both CSR:T1R2 (SEQ ID NO: 14) and T1R3-TMD (SEQ ID NO: 28), both T1R2-TMD (SEQ ID NO: 2) and CSR:T1R3 (SEQ ID NO: 16), both CSR:T1R2 (SEQ ID NO: 14) and CSR:T1R3 (SEQ ID NO: 16), or
   b) any protein that is at least 95% identical at the amino acid level to any of the proteins listed in a),
   wherein the modified taste receptor optionally further comprises one or more sequence tags selected from a signal sequence and an antibody epitope, and provided that at least one subunit of the modified taste receptor does not comprise a T1R2 or T1R3 venus flytrap domain.

2. A method of identifying a compound or group of compounds that enhances sweet taste comprising the following steps:
   a) determining whether a compound or group of compounds binds to and/or activates a taste receptor outside a taste receptor's venus flytrap domain by a method that comprises (i) contacting a modified taste receptor with the compound or group of compounds and (ii) determining whether the compound or group of compounds binds to and/or activates the modified taste receptor, and
   b) determining whether the compound or group of compounds that binds to and/or activates the modified taste receptor in the method of step a) enhances sweet taste by
      i) determining whether the compound or group of compounds enhances binding to and/or activation of a chimeric receptor by a ligand for the chimeric receptor, or
      ii) determining whether the compound or group of compounds enhances sweet taste of a sweetener in an assay in which the sweetener is present at a concentration isosweet to a sucrose solution of concentration 2% or greater and the compound is present at a concentration isosweet to a sucrose solution of less than 2% concentration, wherein the chimeric receptor comprises a subunit comprising 1) a venus flytrap domain derived from a class C G-protein coupled receptor, and 2) T1R2 lacking its venus flytrap domain, and optionally a subunit comprising 3) a venus flytrap domain derived from a class C G-protein coupled receptor, and 4) T1R3 lacking its venus flytrap domain, wherein T1R2 lacking its venus flytrap domain comprises the amino acid sequence of SEQ ID NO: 2, and wherein at least one subunit does not comprise a T1R2 or T1R3 venus flytrap domain, and wherein the modified taste receptor comprises:

c) T1R2-TMD (SEQ ID NO: 2), T1R3-TMD (SEQ ID NO: 28), both T1R2-TMD (SEQ ID NO: 2) and T1R3-TMD (SEQ ID NO: 28), CSR:T1R2 (SEQ ID NO: 14), CSR:T1R3 (SEQ ID NO: 16), both CSR:T1R2 (SEQ ID NO: 14) and T1R3-TMD (SEQ ID NO: 28), both T1R2-TMD (SEQ ID NO: 2) and CSR:T1R3 (SEQ ID NO: 16), both CSR:T1R2 (SEQ ID NO: 14) and CSR:T1R3 (SEQ ID NO: 16), or d) any protein that is at least 95% identical at the amino acid level to any of the proteins listed in c)

wherein the modified taste receptor optionally further comprises one or more sequence tags selected from a signal sequence and an antibody epitope, and provided that at least one subunit of the modified taste receptor does not comprise a T1R2 or T1R3 venus flytrap domain.

3. The method according to claim 2, wherein step a) uses cells that express a G-protein.

4. The method according to claim 3 wherein the G-protein is a chimeric G-protein based on Gaq-Gustducin.

5. The method according to claim 4 wherein the G-protein is the chimeric G-protein Galpha16-gustducin 44.

6. The method according to claim 2, wherein step a) uses cells that have been transiently or stably transfected with one or more nucleic acids that encode a protein comprising the transmembrane domain of T1R2 and/or T1R3.

7. The method according to claim 2 further comprising the step of determining whether at least one compound affects the functional activity of the taste receptor in cells by measuring at least one functional response in the cells, wherein said determination is performed by measuring a change in or caused by intracellular messengers.

8. The method according to claim 7, wherein the functional response is determined by measuring a change in an intracellular messenger selected from IP3 and calcium$^{2+}$.

9. The method according to claim 2 wherein step a) uses cells, and further wherein the cells are selected from the group consisting of eucaryotic cells, yeast cells, insect cells, mammalian cells, amphibian cells, and worm cells.

10. The method according to claim 9, wherein the cells are mammalian cells.

11. The method according to claim 10, wherein the mammalian cells are selected from the group consisting of CHO, COS, HeLa and HEK-293 cells.

12. The method according to claim 2, further comprising contacting the T1R2 sweet receptor with the compound or group of compounds a in the presence of a sweet tastant.

13. The method according to claim 2, wherein the ligand is selected from the group consisting of perillartine, p-ethoxybenzaldehyde, cinnamonitrile, stevioside, rubusoside, rebaudioside A and neohesperidin dihydrochalcone.

14. The method according to claim 2, wherein the changes in response to ligand binding to a receptor are measured or determined by a method selected from the group consisting of fluorescence spectroscopy, NMR spectroscopy, measuring of one or more of absorbance, refractive index, hydrodynamic methods, chromatography, measuring solubility, biochemical, wherein the methods measure the properties of a receptor polypeptide in a suitable environment selected from the group consisting of solution, bilayer membrane, attached to a solid phase, in a lipid monolayer, bound on a membrane, and in vesicles.

15. The method according to claim 2 provided that methods that employ both full-length wild-type T1R2 and full-length wild-type T1R3 are not encompassed.

16. A method for determining whether a test agent modulates the response of a T1R2 sweet receptor to a T1R2-TMD sweet receptor agonist, said method comprising
(i) growing recombinant cells on a solid support, wherein the recombinant cells express a T1R2-TMD sweet receptor or a polypeptide at least 95% identical thereto, but do not express a T1R3 receptor;
(ii) adding test agents to a culture medium of defined plates or wells in the presence of the agonist in a suitable concentration, and
(iii) determining a change in a functional response of the cells by comparing the response in presence and absence of the test agent.

17. A method to identify an agent that modulates T1R2-TMD, the method comprising:
(i) measuring a parameter that changes in response to ligand binding to T1R2-TMD
(ii) determining a change of the parameter in response to a test agent, optionally in presence of a ligand, in comparison to a negative control and thereby identifying a modulator or ligand.

18. The method according to claim 17, wherein (i) is performed by a method selected from the group consisting of fluorescence spectroscopy, NMR spectroscopy, measuring of one or more of absorbance, refractive index, hydrodynamic methods, chromatography, measuring solubility, biochemical, wherein the methods measure the properties of the T1R2-TMD polypeptide in a suitable environment selected form the group consisting of solution, bilayer membrane, attached to a solid phase, in a lipid monolayer, bound on a membrane, and in vesicles.

19. A method of identifying a sweetness enhancer comprising contacting a sweet receptor in vitro with:
i) a candidate sweet enhancer,
ii) a sweet tastant, and
iii) with i) and ii) simultaneously,
and measuring the sweet receptor's responses, wherein the sweet receptor comprises:
a) T1R2-TMD (SEQ ID NO: 2), T1R3-TMD (SEQ ID NO: 28), both T1R2-TMD (SEQ ID NO: 2) and T1R3-TMD (SEQ ID NO: 28), CSR:T1R2 (SEQ ID NO: 14), CSR:T1R3 (SEQ ID NO: 16), both CSR:T1R2 (SEQ ID NO: 14) and T1R3-TMD (SEQ ID NO: 28), both T1R2-TMD (SEQ ID NO: 2) and CSR:T1R3 (SEQ ID NO: 16), both CSR:T1R2 (SEQ ID NO: 14) and CSR:T1R3 (SEQ ID NO: 16), and provided that at least one subunit of the sweet receptor does not comprise a T1R2 or T1R3 venus flytrap domain;
or, b) any protein that is at least 95% identical at the amino acid level to any of the proteins listed in a).

20. The method of claim 19, wherein the sweet receptor responses are determined by fluorescence spectroscopy, NMR spectroscopy, measuring absorbance, measuring refractive index, hydrodynamic methods, chromatography, measuring solubility, or measuring any other biochemical property.

21. The method of claim 19, wherein the sweet receptor comprises a combination of a wild-type taste receptor and a chimeric taste receptor, wherein the chimeric taste receptor comprises a class C GPCR venus fly-trap other than the wildtype taste receptor venus fly-trap domain.

* * * * *

SEQUENCE LISTING

<160> NUMBER OF SEQ ID NOS: 29

<210> SEQ ID NO 1
<211> LENGTH: 828
<212> TYPE: DNA
<213> ORGANISM: Homo sapiens
<220> FEATURE:
<221> NAME/KEY: CDS
<222> LOCATION: (1)..(828)

<400> SEQUENCE: 1

```
gca ccc acc atc gct gtg gcc ctg ctg gcc gcc ctg ggc ttc ctc agc        48
Ala Pro Thr Ile Ala Val Ala Leu Leu Ala Ala Leu Gly Phe Leu Ser
1               5                   10                  15 acc ctg gcc atc ctg gtg ata ttc tgg agg cac ttc cag aca ccc ata        96
Thr Leu Ala Ile Leu Val Ile Phe Trp Arg His Phe Gln Thr Pro Ile
                20                  25                  30 gtt cgc tcg gct ggg ggc ccc atg tgc ttc ctg atg ctg aca ctg ctg       144
Val Arg Ser Ala Gly Gly Pro Met Cys Phe Leu Met Leu Thr Leu Leu
            35                  40                  45 ctg gtg gca tac atg gtg gtc ccg gtg tac gtg ggg ccg ccc aag gtc       192
Leu Val Ala Tyr Met Val Val Pro Val Tyr Val Gly Pro Pro Lys Val
        50                  55                  60 tcc acc tgc ctc tgc cgc cag gcc ctc ttt ccc ctc tgc ttc aca att       240
Ser Thr Cys Leu Cys Arg Gln Ala Leu Phe Pro Leu Cys Phe Thr Ile
65                  70                  75                  80 tgc atc tcc tgt atc gcc gtg cgt tct ttc cag atc gtc tgc gcc ttc       288
Cys Ile Ser Cys Ile Ala Val Arg Ser Phe Gln Ile Val Cys Ala Phe
                85                  90                  95 aag atg gcc agc cgc ttc cca cgc gcc tac agc tac tgg gtc cgc tac       336
Lys Met Ala Ser Arg Phe Pro Arg Ala Tyr Ser Tyr Trp Val Arg Tyr
            100                 105                 110 cag ggg ccc tac gtc tct atg gca ttt atc acg gta ctc aaa atg gtc       384
Gln Gly Pro Tyr Val Ser Met Ala Phe Ile Thr Val Leu Lys Met Val
        115                 120                 125 att gtg gta att ggc atg ctg gcc acg ggc ctc agt ccc acc acc cgt       432
Ile Val Val Ile Gly Met Leu Ala Thr Gly Leu Ser Pro Thr Thr Arg
    130                 135                 140 act gac ccc gat gac ccc aag atc aca att gtc tcc tgt aac ccc aac       480
Thr Asp Pro Asp Asp Pro Lys Ile Thr Ile Val Ser Cys Asn Pro Asn
```

```
                  145                 150                 155                 160
tac cgc aac agc ctg ctg ttc aac acc agc ctg gac ctg ctc tca        528
Tyr Arg Asn Ser Leu Leu Phe Asn Thr Ser Leu Asp Leu Leu Ser
                165                 170                 175 gtg gtg ggt ttc agc ttc gcc tac atg ggc aaa gag ctg ccc acc aac    576
Val Val Gly Phe Ser Phe Ala Tyr Met Gly Lys Glu Leu Pro Thr Asn
                180                 185                 190 tac aac gag gcc aag ttc atc acc ctc agc atg acc ttc tat ttc acc    624
Tyr Asn Glu Ala Lys Phe Ile Thr Leu Ser Met Thr Phe Tyr Phe Thr
                195                 200                 205 tca tct gtc tcc ctc tgc acc ttc atg tct gcc tac agc ggg gtg ctg    672
Ser Ser Val Ser Leu Cys Thr Phe Met Ser Ala Tyr Ser Gly Val Leu
            210                 215                 220 gtc acc atc gtg gac ctc ttg gtc act gtg ctc aac ctc ctg gcc atc    720
Val Thr Ile Val Asp Leu Leu Val Thr Val Leu Asn Leu Leu Ala Ile
225                 230                 235                 240 agc ctg ggc tac ttc ggc ccc aag tgc tac atg atc ctc ttc tac ccg    768
Ser Leu Gly Tyr Phe Gly Pro Lys Cys Tyr Met Ile Leu Phe Tyr Pro
                245                 250                 255 gag cgc aac acg ccc gcc tac ttc aac agc atg atc cag ggc tac acc    816
Glu Arg Asn Thr Pro Ala Tyr Phe Asn Ser Met Ile Gln Gly Tyr Thr
                260                 265                 270 atg agg agg gac                                                    828
Met Arg Arg Asp
        275

<210> SEQ ID NO 2
<211> LENGTH: 276
<212> TYPE: PRT
<213> ORGANISM: Homo sapiens

<400> SEQUENCE: 2

Ala Pro Thr Ile Ala Val Ala Leu Leu Ala Ala Leu Gly Phe Leu Ser
1               5                   10                  15

Thr Leu Ala Ile Leu Val Ile Phe Trp Arg His Phe Gln Thr Pro Ile
                20                  25                  30

Val Arg Ser Ala Gly Gly Pro Met Cys Phe Leu Met Leu Thr Leu Leu
            35                  40                  45

Leu Val Ala Tyr Met Val Pro Val Tyr Val Gly Pro Pro Lys Val
        50                  55                  60

Ser Thr Cys Leu Cys Arg Gln Ala Leu Phe Pro Leu Cys Phe Thr Ile
65              70                  75                  80

Cys Ile Ser Cys Ile Ala Val Arg Ser Phe Gln Ile Val Cys Ala Phe
                85                  90                  95

Lys Met Ala Ser Arg Phe Pro Arg Ala Tyr Ser Tyr Trp Val Arg Tyr
            100                 105                 110

Gln Gly Pro Tyr Val Ser Met Ala Phe Ile Thr Val Leu Lys Met Val
        115                 120                 125

Ile Val Val Ile Gly Met Leu Ala Thr Gly Leu Ser Pro Thr Thr Arg
    130                 135                 140

Thr Asp Pro Asp Pro Lys Ile Thr Ile Val Ser Cys Asn Pro Asn
145                 150                 155                 160

Tyr Arg Asn Ser Leu Leu Phe Asn Thr Ser Leu Asp Leu Leu Leu Ser
                165                 170                 175

Val Val Gly Phe Ser Phe Ala Tyr Met Gly Lys Glu Leu Pro Thr Asn
            180                 185                 190

Tyr Asn Glu Ala Lys Phe Ile Thr Leu Ser Met Thr Phe Tyr Phe Thr
        195                 200                 205
```

```
Ser Ser Val Ser Leu Cys Thr Phe Met Ser Ala Tyr Ser Gly Val Leu
    210                 215                 220

Val Thr Ile Val Asp Leu Leu Val Thr Val Leu Asn Leu Leu Ala Ile
225                 230                 235                 240

Ser Leu Gly Tyr Phe Gly Pro Lys Cys Tyr Met Ile Leu Phe Tyr Pro
                245                 250                 255

Glu Arg Asn Thr Pro Ala Tyr Phe Asn Ser Met Ile Gln Gly Tyr Thr
            260                 265                 270

Met Arg Arg Asp
        275

<210> SEQ ID NO 3
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (4)..(144)

<400> SEQUENCE: 3 acc atg gcc gct gtt acc tat cct tca tcc gtg cct acg acc ttg gac      48
    Met Ala Ala Val Thr Tyr Pro Ser Ser Val Pro Thr Thr Leu Asp
    1               5                   10                  15 cct ggg aat gca tcc tca gcc tgg ccc ctg gac acg tcc ctg ggg aat      96
Pro Gly Asn Ala Ser Ser Ala Trp Pro Leu Asp Thr Ser Leu Gly Asn
                20                  25                  30 gca tct gct ggc act agc ctg gca gga ctg gct gtc agt ggc gaa ttc     144
Ala Ser Ala Gly Thr Ser Leu Ala Gly Leu Ala Val Ser Gly Glu Phe
            35                  40                  45

<210> SEQ ID NO 4
<211> LENGTH: 47
<212> TYPE: PRT
<213> ORGANISM: Artificial Sequence
<220> FEATURE:
<223> OTHER INFORMATION: Synthetic Construct

<400> SEQUENCE: 4

Met Ala Ala Val Thr Tyr Pro Ser Ser Val Pro Thr Thr Leu Asp Pro
1               5                   10                  15

Gly Asn Ala Ser Ser Ala Trp Pro Leu Asp Thr Ser Leu Gly Asn Ala
                20                  25                  30

Ser Ala Gly Thr Ser Leu Ala Gly Leu Ala Val Ser Gly Glu Phe
            35                  40                  45

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(42)

<400> SEQUENCE: 5 tgc ggc cgc cag cct gaa ctc gct cct gaa gac ccg gaa gat taa          45
Cys Gly Arg Gln Pro Glu Leu Ala Pro Glu Asp Pro Glu Asp
1               5                   10
```

<210> SEQ ID NO 6
<211> LENGTH: 14
<212> TYPE: PRT
<213> ORGANISM: Artificial Sequence
<220> FEATURE:
<223> OTHER INFORMATION: Synthetic Construct

<400> SEQUENCE: 6

Cys Gly Arg Gln Pro Glu Leu Ala Pro Glu Asp Pro Glu Asp
1               5                   10

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tatagaattc gcacccacca tcgctgtggc c                                      31

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atatgcggcc gcagtccctc ctcatggt                                          28

<210> SEQ ID NO 9
<211> LENGTH: 2520
<212> TYPE: DNA
<213> ORGANISM: Homo sapiens
<220> FEATURE:
<221> NAME/KEY: CDS
<222> LOCATION: (1)..(2517)

<400> SEQUENCE: 9 atg ggg ccc agg gca aag acc atc tcc tcc ctg ttc ttc ctc cta tgg      48
Met Gly Pro Arg Ala Lys Thr Ile Ser Ser Leu Phe Phe Leu Leu Trp
1               5                   10                  15 gtc ctg gct gag ccg gct gag aac tcg gac ttc tac ctg cct ggg gat      96
Val Leu Ala Glu Pro Ala Glu Asn Ser Asp Phe Tyr Leu Pro Gly Asp
            20                  25                  30 tac ctc ctg ggt ggc ctc ttc tcc ctc cat gcc aac atg aag ggc att     144
Tyr Leu Leu Gly Gly Leu Phe Ser Leu His Ala Asn Met Lys Gly Ile
        35                  40                  45 gtt cac ctt aac ttc ctg cag gtg ccc atg tgc aag gag tat gaa gtg     192
Val His Leu Asn Phe Leu Gln Val Pro Met Cys Lys Glu Tyr Glu Val
    50                  55                  60 aag gtg ata ggc tac aac ctc atg cag gcc atg cgc ttt gcg gtg gag     240
Lys Val Ile Gly Tyr Asn Leu Met Gln Ala Met Arg Phe Ala Val Glu
65                  70                  75                  80 gag atc aac aat gac agc agc ctg ctg cct ggt gtg ctg ctg ggc tat     288
Glu Ile Asn Asn Asp Ser Ser Leu Leu Pro Gly Val Leu Leu Gly Tyr
                85                  90                  95 gag atc gtg gat gtg tgc tac atc tcc aac aat gtc cag ccg gtg ctc     336
Glu Ile Val Asp Val Cys Tyr Ile Ser Asn Asn Val Gln Pro Val Leu
            100                 105                 110 tac ttc ctg gca cac gag gac aac ctc ctt ccc atc caa gag gac tac     384
Tyr Phe Leu Ala His Glu Asp Asn Leu Leu Pro Ile Gln Glu Asp Tyr
        115                 120                 125

```
agt aac tac att tcc cgt gtg gtg gct gtc att ggc cct gac aac tcc    432
Ser Asn Tyr Ile Ser Arg Val Val Ala Val Ile Gly Pro Asp Asn Ser
    130             135                 140 gag tct gtc atg act gtg gcc aac ttc ctc tcc cta ttt ctc ctt cca    480
Glu Ser Val Met Thr Val Ala Asn Phe Leu Ser Leu Phe Leu Leu Pro
145             150                 155                 160 cag atc acc tac agc gcc atc agc gat gag ctg cga gac aag gtg cgc    528
Gln Ile Thr Tyr Ser Ala Ile Ser Asp Glu Leu Arg Asp Lys Val Arg
                165                 170                 175 ttc ccg gct ttg ctg cgt acc aca ccc agc gcc gac cac cac atc gag    576
Phe Pro Ala Leu Leu Arg Thr Thr Pro Ser Ala Asp His His Ile Glu
            180                 185                 190 gcc atg gtg cag ctg atg ctg cac ttc cgc tgg aac tgg atc att gtg    624
Ala Met Val Gln Leu Met Leu His Phe Arg Trp Asn Trp Ile Ile Val
        195                 200                 205 ctg gtg agc agc gac acc tat ggc cgc gac aat ggc cag ctg ctt ggc    672
Leu Val Ser Ser Asp Thr Tyr Gly Arg Asp Asn Gly Gln Leu Leu Gly
    210                 215                 220 gag cgc gtg gcc cgg cgc gac atc tgc atc gcc ttc cag gag acg ctg    720
Glu Arg Val Ala Arg Arg Asp Ile Cys Ile Ala Phe Gln Glu Thr Leu
225                 230                 235                 240 ccc aca ctg cag ccc aac cag aac atg acg tca gag gag cgc cag cgc    768
Pro Thr Leu Gln Pro Asn Gln Asn Met Thr Ser Glu Glu Arg Gln Arg
                245                 250                 255 ctg gtg acc att gtg gac aag ctg cag cag agc aca gcg cgc gtc gtg    816
Leu Val Thr Ile Val Asp Lys Leu Gln Gln Ser Thr Ala Arg Val Val
            260                 265                 270 gtc gtg ttc tcg ccc gac ctg acc ctg tac cac ttc ttc aat gag gtg    864
Val Val Phe Ser Pro Asp Leu Thr Leu Tyr His Phe Phe Asn Glu Val
        275                 280                 285 ctg cgc cag aac ttc act ggc gcc gtg tgg atc gcc tcc gag tcc tgg    912
Leu Arg Gln Asn Phe Thr Gly Ala Val Trp Ile Ala Ser Glu Ser Trp
    290                 295                 300 gcc atc gac ccg gtc ctg cac aac ctc acg gag ctg cgc cac ttg ggc    960
Ala Ile Asp Pro Val Leu His Asn Leu Thr Glu Leu Arg His Leu Gly
305                 310                 315                 320 acc ttc ctg ggc atc acc atc cag agc gtg ccc atc ccg ggc ttc agt    1008
Thr Phe Leu Gly Ile Thr Ile Gln Ser Val Pro Ile Pro Gly Phe Ser
                325                 330                 335 gag ttc cgc gag tgg ggc cca cag gct ggg ccg cca ccc ctc agc agg    1056
Glu Phe Arg Glu Trp Gly Pro Gln Ala Gly Pro Pro Pro Leu Ser Arg
            340                 345                 350 acc agc cag agc tat acc tgc aac cag gag tgc gac aac tgc ctg aac    1104
Thr Ser Gln Ser Tyr Thr Cys Asn Gln Glu Cys Asp Asn Cys Leu Asn
        355                 360                 365 gcc acc ttg tcc ttc aac acc att ctc agg ctc tct ggg gag cgt gtc    1152
Ala Thr Leu Ser Phe Asn Thr Ile Leu Arg Leu Ser Gly Glu Arg Val
    370                 375                 380 gtc tac agc gtg tac tct gcg gtc tat gct gtg gcc cat gcc ctg cac    1200
Val Tyr Ser Val Tyr Ser Ala Val Tyr Ala Val Ala His Ala Leu His
385                 390                 395                 400 agc ctc ctc ggc tgt gac aaa agc acc tgc acc aag agg gtg gtc tac    1248
Ser Leu Leu Gly Cys Asp Lys Ser Thr Cys Thr Lys Arg Val Val Tyr
                405                 410                 415 ccc tgg cag ctg ctt gag gag atc tgg aag gtc aac ttc act ctc ctg    1296
Pro Trp Gln Leu Leu Glu Glu Ile Trp Lys Val Asn Phe Thr Leu Leu
            420                 425                 430 gac cac caa atc ttc ttc gac ccg caa ggg gac gtg gct ctg cac ttg    1344
Asp His Gln Ile Phe Phe Asp Pro Gln Gly Asp Val Ala Leu His Leu
        435                 440                 445
```

```
gag att gtc cag tgg caa tgg gac cgg agc cag aat ccc ttc cag agc      1392
Glu Ile Val Gln Trp Gln Trp Asp Arg Ser Gln Asn Pro Phe Gln Ser
    450                 455                 460 gtc gcc tcc tac tac ccc ctg cag cga cag ctg aag aac atc caa gac      1440
Val Ala Ser Tyr Tyr Pro Leu Gln Arg Gln Leu Lys Asn Ile Gln Asp
465                 470                 475                 480 atc tcc tgg cac acc atc aac aac acg atc cct atg tcc atg tgt tcc      1488
Ile Ser Trp His Thr Ile Asn Asn Thr Ile Pro Met Ser Met Cys Ser
                485                 490                 495 aag agg tgc cag tca ggg caa aag aag aag cct gtg ggc atc cac gtc      1536
Lys Arg Cys Gln Ser Gly Gln Lys Lys Lys Pro Val Gly Ile His Val
                500                 505                 510 tgc tgc ttc gag tgc atc gac tgc ctt ccc ggc acc ttc ctc aac cac      1584
Cys Cys Phe Glu Cys Ile Asp Cys Leu Pro Gly Thr Phe Leu Asn His
            515                 520                 525 act gaa gat gaa tat gaa tgc cag gcc tgc ccg aat aac gag tgg tcc      1632
Thr Glu Asp Glu Tyr Glu Cys Gln Ala Cys Pro Asn Asn Glu Trp Ser
530                 535                 540 tac cag agt gag acc tcc tgc ttc aag cgg cag ctg gtc ttc ctg gaa      1680
Tyr Gln Ser Glu Thr Ser Cys Phe Lys Arg Gln Leu Val Phe Leu Glu
545                 550                 555                 560 tgg cat gag gca ccc acc atc gct gtg gcc ctg ctg gcc gcc ctg ggc      1728
Trp His Glu Ala Pro Thr Ile Ala Val Ala Leu Leu Ala Ala Leu Gly
                565                 570                 575 ttc ctc agc acc ctg gcc atc ctg gtg ata ttc tgg agg cac ttc cag      1776
Phe Leu Ser Thr Leu Ala Ile Leu Val Ile Phe Trp Arg His Phe Gln
            580                 585                 590 aca ccc ata gtt cgc tcg gct ggg ggc ccc atg tgc ttc ctg atg ctg      1824
Thr Pro Ile Val Arg Ser Ala Gly Gly Pro Met Cys Phe Leu Met Leu
            595                 600                 605 aca ctg ctg ctg gtg gca tac atg gtg gtc ccg gtg tac gtg ggg ccg      1872
Thr Leu Leu Leu Val Ala Tyr Met Val Val Pro Val Tyr Val Gly Pro
610                 615                 620 ccc aag gtc tcc acc tgc ctc tgc cgc cag gcc ctc ttt ccc ctc tgc      1920
Pro Lys Val Ser Thr Cys Leu Cys Arg Gln Ala Leu Phe Pro Leu Cys
625                 630                 635                 640 ttc aca atc tgc atc tcc tgt atc gcc gtg cgt tct ttc cag atc gtc      1968
Phe Thr Ile Cys Ile Ser Cys Ile Ala Val Arg Ser Phe Gln Ile Val
                645                 650                 655 tgc gcc ttc aag atg gcc agc cgc ttc cca cgc gcc tac agc tac tgg      2016
Cys Ala Phe Lys Met Ala Ser Arg Phe Pro Arg Ala Tyr Ser Tyr Trp
            660                 665                 670 gtc cgc tac cag ggg ccc tac gtc tct atg gca ttt atc acg gta ctc      2064
Val Arg Tyr Gln Gly Pro Tyr Val Ser Met Ala Phe Ile Thr Val Leu
            675                 680                 685 aaa atg gtc att gtg gta att ggc atg ctg gcc acg ggc ctc agt ccc      2112
Lys Met Val Ile Val Val Ile Gly Met Leu Ala Thr Gly Leu Ser Pro
690                 695                 700 acc acc cgt act gac ccc gat gac ccc aag atc aca att gtc tcc tgt      2160
Thr Thr Arg Thr Asp Pro Asp Asp Pro Lys Ile Thr Ile Val Ser Cys
705                 710                 715                 720 aac ccc aac tac cgc aac agc ctg ctg ttc aac acc agc ctg gac ctg      2208
Asn Pro Asn Tyr Arg Asn Ser Leu Leu Phe Asn Thr Ser Leu Asp Leu
                725                 730                 735 ctg ctc tca gtg gtg ggt ttc agc ttc gcc tac atg ggc aaa gag ctg      2256
Leu Leu Ser Val Val Gly Phe Ser Phe Ala Tyr Met Gly Lys Glu Leu
            740                 745                 750 ccc acc aac tac aac gag gcc aag ttc atc acc ctc agc atg acc ttc      2304
Pro Thr Asn Tyr Asn Glu Ala Lys Phe Ile Thr Leu Ser Met Thr Phe
            755                 760                 765
```

```
tat ttc acc tca tct gtc tcc ctc tgc acc ttc atg tct gcc tac agc    2352
Tyr Phe Thr Ser Ser Val Ser Leu Cys Thr Phe Met Ser Ala Tyr Ser
        770                 775                 780 ggg gtg ctg gtc acc atc gtg gac ctc ttg gtc act gtg ctc aac ctc    2400
Gly Val Leu Val Thr Ile Val Asp Leu Leu Val Thr Val Leu Asn Leu
785                 790                 795                 800 ctg gcc atc agc ctg ggc tac ttc ggc ccc aag tgc tac atg atc ctc    2448
Leu Ala Ile Ser Leu Gly Tyr Phe Gly Pro Lys Cys Tyr Met Ile Leu
                805                 810                 815 ttc tac ccg gag cgc aac acg ccc gcc tac ttc aac agc atg atc cag    2496
Phe Tyr Pro Glu Arg Asn Thr Pro Ala Tyr Phe Asn Ser Met Ile Gln
            820                 825                 830 ggc tac acc atg agg agg gac tag                                    2520
Gly Tyr Thr Met Arg Arg Asp
        835

<210> SEQ ID NO 10
<211> LENGTH: 839
<212> TYPE: PRT
<213> ORGANISM: Homo sapiens

<400> SEQUENCE: 10

Met Gly Pro Arg Ala Lys Thr Ile Ser Ser Leu Phe Phe Leu Leu Trp
1               5                   10                  15

Val Leu Ala Glu Pro Ala Glu Asn Ser Asp Phe Tyr Leu Pro Gly Asp
            20                  25                  30

Tyr Leu Leu Gly Gly Leu Phe Ser Leu His Ala Asn Met Lys Gly Ile
        35                  40                  45

Val His Leu Asn Phe Leu Gln Val Pro Met Cys Lys Glu Tyr Glu Val
    50                  55                  60

Lys Val Ile Gly Tyr Asn Leu Met Gln Ala Met Arg Phe Ala Val Glu
65                  70                  75                  80

Glu Ile Asn Asn Asp Ser Ser Leu Leu Pro Gly Val Leu Leu Gly Tyr
                85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Glu Asp Tyr
        115                 120                 125

Ser Asn Tyr Ile Ser Arg Val Val Ala Val Ile Gly Pro Asp Asn Ser
130                 135                 140

Glu Ser Val Met Thr Val Ala Asn Phe Leu Ser Leu Phe Leu Leu Pro
145                 150                 155                 160

Gln Ile Thr Tyr Ser Ala Ile Ser Asp Glu Leu Arg Asp Lys Val Arg
                165                 170                 175

Phe Pro Ala Leu Leu Arg Thr Thr Pro Ser Ala Asp His His Ile Glu
            180                 185                 190

Ala Met Val Gln Leu Met Leu His Phe Arg Trp Asn Trp Ile Ile Val
        195                 200                 205

Leu Val Ser Ser Asp Thr Tyr Gly Arg Asp Asn Gly Gln Leu Leu Gly
    210                 215                 220

Glu Arg Val Ala Arg Arg Asp Ile Cys Ile Ala Phe Gln Glu Thr Leu
225                 230                 235                 240

Pro Thr Leu Gln Pro Asn Gln Asn Met Thr Ser Glu Glu Arg Gln Arg
                245                 250                 255

Leu Val Thr Ile Val Asp Lys Leu Gln Gln Ser Thr Ala Arg Val Val
            260                 265                 270
```

-continued

```
Val Val Phe Ser Pro Asp Leu Thr Leu Tyr His Phe Asn Glu Val
        275                 280                 285

Leu Arg Gln Asn Phe Thr Gly Ala Val Trp Ile Ala Ser Glu Ser Trp
    290                 295                 300

Ala Ile Asp Pro Val Leu His Asn Leu Thr Glu Leu Arg His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Leu Ser Arg
                340                 345                 350

Thr Ser Gln Ser Tyr Thr Cys Asn Gln Glu Cys Asp Asn Cys Leu Asn
    355                 360                 365

Ala Thr Leu Ser Phe Asn Thr Ile Leu Arg Leu Ser Gly Glu Arg Val
370                 375                 380

Val Tyr Ser Val Tyr Ser Ala Val Tyr Ala Val Ala His Ala Leu His
385                 390                 395                 400

Ser Leu Leu Gly Cys Asp Lys Ser Thr Cys Thr Lys Arg Val Val Tyr
                405                 410                 415

Pro Trp Gln Leu Leu Glu Glu Ile Trp Lys Val Asn Phe Thr Leu Leu
                420                 425                 430

Asp His Gln Ile Phe Phe Asp Pro Gln Gly Asp Val Ala Leu His Leu
    435                 440                 445

Glu Ile Val Gln Trp Gln Trp Asp Arg Ser Gln Asn Pro Phe Gln Ser
450                 455                 460

Val Ala Ser Tyr Tyr Pro Leu Gln Arg Gln Leu Lys Asn Ile Gln Asp
465                 470                 475                 480

Ile Ser Trp His Thr Ile Asn Asn Thr Ile Pro Met Ser Met Cys Ser
                485                 490                 495

Lys Arg Cys Gln Ser Gly Gln Lys Lys Pro Val Gly Ile His Val
                500                 505                 510

Cys Cys Phe Glu Cys Ile Asp Cys Leu Pro Gly Thr Phe Leu Asn His
    515                 520                 525

Thr Glu Asp Glu Tyr Glu Cys Gln Ala Cys Pro Asn Asn Glu Trp Ser
530                 535                 540

Tyr Gln Ser Glu Thr Ser Cys Phe Lys Arg Gln Leu Val Phe Leu Glu
545                 550                 555                 560

Trp His Glu Ala Pro Thr Ile Ala Val Ala Leu Leu Ala Ala Leu Gly
                565                 570                 575

Phe Leu Ser Thr Leu Ala Ile Leu Val Ile Phe Trp Arg His Phe Gln
                580                 585                 590

Thr Pro Ile Val Arg Ser Ala Gly Gly Pro Met Cys Phe Leu Met Leu
    595                 600                 605

Thr Leu Leu Leu Val Ala Tyr Met Val Val Pro Val Tyr Val Gly Pro
610                 615                 620

Pro Lys Val Ser Thr Cys Leu Cys Arg Gln Ala Leu Phe Pro Leu Cys
625                 630                 635                 640

Phe Thr Ile Cys Ile Ser Cys Ile Ala Val Arg Ser Phe Gln Ile Val
                645                 650                 655

Cys Ala Phe Lys Met Ala Ser Arg Phe Pro Arg Ala Tyr Ser Tyr Trp
                660                 665                 670

Val Arg Tyr Gln Gly Pro Tyr Val Ser Met Ala Phe Ile Thr Val Leu
    675                 680                 685

Lys Met Val Ile Val Val Ile Gly Met Leu Ala Thr Gly Leu Ser Pro
690                 695                 700
```

```
Thr Thr Arg Thr Asp Pro Asp Pro Lys Ile Thr Ile Val Ser Cys
705                 710                 715                 720

Asn Pro Asn Tyr Arg Asn Ser Leu Leu Phe Asn Thr Ser Leu Asp Leu
            725                 730                 735

Leu Leu Ser Val Val Gly Phe Ser Phe Ala Tyr Met Gly Lys Glu Leu
            740                 745                 750

Pro Thr Asn Tyr Asn Glu Ala Lys Phe Ile Thr Leu Ser Met Thr Phe
        755                 760                 765

Tyr Phe Thr Ser Ser Val Ser Leu Cys Thr Phe Met Ser Ala Tyr Ser
        770                 775                 780

Gly Val Leu Val Thr Ile Val Asp Leu Leu Val Thr Val Leu Asn Leu
785                 790                 795                 800

Leu Ala Ile Ser Leu Gly Tyr Phe Gly Pro Lys Cys Tyr Met Ile Leu
                805                 810                 815

Phe Tyr Pro Glu Arg Asn Thr Pro Ala Tyr Phe Asn Ser Met Ile Gln
            820                 825                 830

Gly Tyr Thr Met Arg Arg Asp
            835

<210> SEQ ID NO 11
<211> LENGTH: 2559
<212> TYPE: DNA
<213> ORGANISM: Homo sapiens
<220> FEATURE:
<221> NAME/KEY: CDS
<222> LOCATION: (1)..(2556)

<400> SEQUENCE: 11 atg ctg ggc cct gct gtc ctg ggc ctc agc ctc tgg gct ctc ctg cac     48
Met Leu Gly Pro Ala Val Leu Gly Leu Ser Leu Trp Ala Leu Leu His
1               5                   10                  15 cct ggg acg ggg gcc cca ttg tgc ctg tca cag caa ctt agg atg aag     96
Pro Gly Thr Gly Ala Pro Leu Cys Leu Ser Gln Gln Leu Arg Met Lys
            20                  25                  30 ggg gac tac gtg ctg ggg ggg ctg ttc ccc ctg ggc gag gcc gag gag    144
Gly Asp Tyr Val Leu Gly Gly Leu Phe Pro Leu Gly Glu Ala Glu Glu
        35                  40                  45 gct ggc ctc cgc agc cgg aca cgg ccc agc agc cct gtg tgc acc agg    192
Ala Gly Leu Arg Ser Arg Thr Arg Pro Ser Ser Pro Val Cys Thr Arg
    50                  55                  60 ttc tcc tca aac ggc ctg ctc tgg gca ctg gcc atg aaa atg gcc gtg    240
Phe Ser Ser Asn Gly Leu Leu Trp Ala Leu Ala Met Lys Met Ala Val
65                  70                  75                  80 gag gag atc aac aac aag tcg gat ctg ctg ccc ggg ctg cgc ctg ggc    288
Glu Glu Ile Asn Asn Lys Ser Asp Leu Leu Pro Gly Leu Arg Leu Gly
                85                  90                  95 tac gac ctc ttt gat acg tgc tcg gag cct gtg gtg gcc atg aag ccc    336
Tyr Asp Leu Phe Asp Thr Cys Ser Glu Pro Val Val Ala Met Lys Pro
            100                 105                 110 agc ctc atg ttc ctg gcc aag gca ggc agc cgc gac atc gcc gcc tac    384
Ser Leu Met Phe Leu Ala Lys Ala Gly Ser Arg Asp Ile Ala Ala Tyr
        115                 120                 125 tgc aac tac acg cag tac cag ccc cgt gtg ctg gct gtc atc ggg ccc    432
Cys Asn Tyr Thr Gln Tyr Gln Pro Arg Val Leu Ala Val Ile Gly Pro
    130                 135                 140 cac tcg tca gag ctc gcc atg gtc acc ggc aag ttc ttc agc ttc ttc    480
His Ser Ser Glu Leu Ala Met Val Thr Gly Lys Phe Phe Ser Phe Phe
145                 150                 155                 160 ctc atg ccc cag gtc agc tac ggt gct agc atg gag ctg ctg agc gcc    528
```

```
                                     -continued

Leu Met Pro Gln Val Ser Tyr Gly Ala Ser Met Glu Leu Leu Ser Ala
            165                 170                 175 cgg gag acc ttc ccc tcc ttc ttc cgc acc gtg ccc agc gac cgt gtg    576
Arg Glu Thr Phe Pro Ser Phe Phe Arg Thr Val Pro Ser Asp Arg Val
        180                 185                 190 cag ctg acg gcc gcc gcg gag ctg ctg cag gag ttc ggc tgg aac tgg    624
Gln Leu Thr Ala Ala Ala Glu Leu Leu Gln Glu Phe Gly Trp Asn Trp
            195                 200                 205 gtg gcc gcc ctg ggc agc gac gac gag tac ggc cgg cag ggc ctg agc    672
Val Ala Ala Leu Gly Ser Asp Asp Glu Tyr Gly Arg Gln Gly Leu Ser
    210                 215                 220 atc ttc tcg gcc ctg gcc gcg gca cgc ggc atc tgc atc gcg cac gag    720
Ile Phe Ser Ala Leu Ala Ala Ala Arg Gly Ile Cys Ile Ala His Glu
225                 230                 235                 240 ggc ctg gtg ccg ctg ccc cgt gcc gat gac tcg cgg ctg ggg aag gtg    768
Gly Leu Val Pro Leu Pro Arg Ala Asp Asp Ser Arg Leu Gly Lys Val
                245                 250                 255 cag gac gtc ctg cac cag gtg aac cag agc agc gtg cag gtg gtg ctg    816
Gln Asp Val Leu His Gln Val Asn Gln Ser Ser Val Gln Val Val Leu
            260                 265                 270 ctg ttc gcc tcc gtg cac gcc gcc cac gcc ctc ttc aac tac agc atc    864
Leu Phe Ala Ser Val His Ala Ala His Ala Leu Phe Asn Tyr Ser Ile
        275                 280                 285 agc agc agg ctc tcg ccc aag gtg tgg gtg gcc agc gag gcc tgg ctg    912
Ser Ser Arg Leu Ser Pro Lys Val Trp Val Ala Ser Glu Ala Trp Leu
            290                 295                 300 acc tct gac ctg gtc atg ggg ctg ccc ggc atg gcc cag atg ggc acg    960
Thr Ser Asp Leu Val Met Gly Leu Pro Gly Met Ala Gln Met Gly Thr
305                 310                 315                 320 gtg ctt ggc ttc ctc cag agg ggt gcc cag ctg cac gag ttc ccc cag   1008
Val Leu Gly Phe Leu Gln Arg Gly Ala Gln Leu His Glu Phe Pro Gln
                325                 330                 335 tac gtg aag acg cac ctg gcc ctg gcc acc gac ccg gcc ttc tgc tct   1056
Tyr Val Lys Thr His Leu Ala Leu Ala Thr Asp Pro Ala Phe Cys Ser
            340                 345                 350 gcc ctg ggc gag agg gag cag ggt ctg gag gag gac gtg gtg ggc cag   1104
Ala Leu Gly Glu Arg Glu Gln Gly Leu Glu Glu Asp Val Val Gly Gln
        355                 360                 365 cgc tgc ccg cag tgt gac tgc atc acg ctg cag aac gtg agc gca ggg   1152
Arg Cys Pro Gln Cys Asp Cys Ile Thr Leu Gln Asn Val Ser Ala Gly
    370                 375                 380 cta aat cac cac cag acg ttc tct gtc tac gca gct gtg tat agc gtg   1200
Leu Asn His His Gln Thr Phe Ser Val Tyr Ala Ala Val Tyr Ser Val
385                 390                 395                 400 gcc cag gcc ctg cac aac act ctt cag tgc aac gcc tca ggc tgc ccc   1248
Ala Gln Ala Leu His Asn Thr Leu Gln Cys Asn Ala Ser Gly Cys Pro
                405                 410                 415 gcg cag gac ccc gtg aag ccc tgg cag ctc ctg gag aac atg tac aac   1296
Ala Gln Asp Pro Val Lys Pro Trp Gln Leu Leu Glu Asn Met Tyr Asn
            420                 425                 430 ctg acc ttc cac gtg ggc ggg ctg ccg ctg cgg ttc gac agc agc gga   1344
Leu Thr Phe His Val Gly Gly Leu Pro Leu Arg Phe Asp Ser Ser Gly
        435                 440                 445 aac gtg gac atg gag tac gac ctg aag ctg tgg gtg tgg cag ggc tca   1392
Asn Val Asp Met Glu Tyr Asp Leu Lys Leu Trp Val Trp Gln Gly Ser
    450                 455                 460 gtg ccc agg ctc cac gac gtg ggc agg ttc aac ggc agc ctc agg aca   1440
Val Pro Arg Leu His Asp Val Gly Arg Phe Asn Gly Ser Leu Arg Thr
465                 470                 475                 480 gag cgc ctg aag atc cgc tgg cac acg tct gac aac cag aag ccc gtg   1488
```

```
      Glu Arg Leu Lys Ile Arg Trp His Thr Ser Asp Asn Gln Lys Pro Val
                      485                 490                 495 tcc cgg tgc tcg cgg cag tgc cag gag ggc cag gtg cgc cgg gtc aag        1536
Ser Arg Cys Ser Arg Gln Cys Gln Glu Gly Gln Val Arg Arg Val Lys
                500                 505                 510 ggg ttc cac tcc tgc tgc tac gac tgt gtg gac tgc gag gcg ggc agc        1584
Gly Phe His Ser Cys Cys Tyr Asp Cys Val Asp Cys Glu Ala Gly Ser
                515                 520                 525 tac cgg caa aac cca gac gac atc gcc tgc acc ttt tgt ggc cag gat        1632
Tyr Arg Gln Asn Pro Asp Asp Ile Ala Cys Thr Phe Cys Gly Gln Asp
        530                 535                 540 gag tgg tcc ccg gag cga agc aca cgc tgc ttc cgc cgc agg tct cgg        1680
Glu Trp Ser Pro Glu Arg Ser Thr Arg Cys Phe Arg Arg Arg Ser Arg
545                 550                 555                 560 ttc ctg gca tgg ggc gag ccg gct gtg ctg ctg ctc ctg ctg ctg            1728
Phe Leu Ala Trp Gly Glu Pro Ala Val Leu Leu Leu Leu Leu Leu
                    565                 570                 575 agc ctg gcg ctg ggc ctt gtg ctg gct gct ttg ggg ctg ttc gtt cac        1776
Ser Leu Ala Leu Gly Leu Val Leu Ala Ala Leu Gly Leu Phe Val His
                580                 585                 590 cat cgg gac agc cca ctg gtt cag gcc tcg ggg ggg ccc ctg gcc tgc        1824
His Arg Asp Ser Pro Leu Val Gln Ala Ser Gly Gly Pro Leu Ala Cys
                595                 600                 605 ttt ggc ctg gtg tgc ctg ggc ctg gtc tgc ctc agc gtc ctc ctg ttc        1872
Phe Gly Leu Val Cys Leu Gly Leu Val Cys Leu Ser Val Leu Leu Phe
        610                 615                 620 cct ggc cag ccc agc cct gcc cga tgc ctg gcc cag cag ccc ttg tcc        1920
Pro Gly Gln Pro Ser Pro Ala Arg Cys Leu Ala Gln Gln Pro Leu Ser
625                 630                 635                 640 cac ctc ccg ctc acg ggc tgc ctg agc aca ctc ttc ctg cag gcg gcc        1968
His Leu Pro Leu Thr Gly Cys Leu Ser Thr Leu Phe Leu Gln Ala Ala
                645                 650                 655 gag atc ttc gtg gag tca gaa ctg cct ctg agc tgg gca gac cgg ctg        2016
Glu Ile Phe Val Glu Ser Glu Leu Pro Leu Ser Trp Ala Asp Arg Leu
                660                 665                 670 agt ggc tgc ctg cgg ggg ccc tgg gcc tgg ctg gtg gtg ctg ctg gcc        2064
Ser Gly Cys Leu Arg Gly Pro Trp Ala Trp Leu Val Val Leu Leu Ala
            675                 680                 685 atg ctg gtg gag gtc gca ctg tgc acc tgg tac ctg gtg gcc ttc ccg        2112
Met Leu Val Glu Val Ala Leu Cys Thr Trp Tyr Leu Val Ala Phe Pro
        690                 695                 700 ccg gag gtg gtg acg gac tgg cac atg ctg ccc acg gag gcg ctg gtg        2160
Pro Glu Val Val Thr Asp Trp His Met Leu Pro Thr Glu Ala Leu Val
705                 710                 715                 720 cac tgc cgc aca cgc tcc tgg gtc agc ttc ggc cta gcg cac gcc acc        2208
His Cys Arg Thr Arg Ser Trp Val Ser Phe Gly Leu Ala His Ala Thr
                725                 730                 735 aat gcc acg ctg gcc ttt ctc tgc ttc ctg ggc act ttc ctg gtg cgg        2256
Asn Ala Thr Leu Ala Phe Leu Cys Phe Leu Gly Thr Phe Leu Val Arg
                740                 745                 750 agc cag ccg ggc cgc tac aac cgt gcc cgt ggc ctc acc ttt gcc atg        2304
Ser Gln Pro Gly Arg Tyr Asn Arg Ala Arg Gly Leu Thr Phe Ala Met
            755                 760                 765 ctg gcc tac ttc atc acc tgg gtc tcc ttt gtg ccc ctc ctg gcc aat        2352
Leu Ala Tyr Phe Ile Thr Trp Val Ser Phe Val Pro Leu Leu Ala Asn
770                 775                 780 gtg cag gtg gtc ctc agg ccc gcc gtg cag atg ggc gcc ctc ctg ctc        2400
Val Gln Val Val Leu Arg Pro Ala Val Gln Met Gly Ala Leu Leu Leu
785                 790                 795                 800 tgt gtc ctg ggc atc ctg gct gcc ttc cac ctg ccc agg tgt tac ctg        2448
```

```
Cys Val Leu Gly Ile Leu Ala Ala Phe His Leu Pro Arg Cys Tyr Leu
                805                 810                 815 ctc atg cgg cag cca ggg ctc aac acc ccc gag ttc ttc ctg gga ggg       2496
Leu Met Arg Gln Pro Gly Leu Asn Thr Pro Glu Phe Phe Leu Gly Gly
        820                 825                 830 ggc cct ggg gat gcc caa ggc cag aat gac ggg aac aca gga aat cag       2544
Gly Pro Gly Asp Ala Gln Gly Gln Asn Asp Gly Asn Thr Gly Asn Gln
835                 840                 845 ggg aaa cat gag tga                                                   2559
Gly Lys His Glu
    850

<210> SEQ ID NO 12
<211> LENGTH: 852
<212> TYPE: PRT
<213> ORGANISM: Homo sapiens

<400> SEQUENCE: 12

Met Leu Gly Pro Ala Val Leu Gly Leu Ser Leu Trp Ala Leu Leu His
1               5                   10                  15

Pro Gly Thr Gly Ala Pro Leu Cys Leu Ser Gln Gln Leu Arg Met Lys
            20                  25                  30

Gly Asp Tyr Val Leu Gly Gly Leu Phe Pro Leu Gly Glu Ala Glu Glu
        35                  40                  45

Ala Gly Leu Arg Ser Arg Thr Arg Pro Ser Ser Pro Val Cys Thr Arg
    50                  55                  60

Phe Ser Ser Asn Gly Leu Leu Trp Ala Leu Ala Met Lys Met Ala Val
65                  70                  75                  80

Glu Glu Ile Asn Asn Lys Ser Asp Leu Leu Pro Gly Leu Arg Leu Gly
                85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
            180                 185                 190

Gln Leu Thr Ala Ala Ala Glu Leu Leu Gln Glu Phe Gly Trp Asn Trp
        195                 200                 205

Val Ala Ala Leu Gly Ser Asp Asp Glu Tyr Gly Arg Gln Gly Leu Ser
    210                 215                 220

Ile Phe Ser Ala Leu Ala Ala Ala Arg Gly Ile Cys Ile Ala His Glu
225                 230                 235                 240

Gly Leu Val Pro Leu Pro Arg Ala Asp Asp Ser Arg Leu Gly Lys Val
                245                 250                 255

Gln Asp Val Leu His Gln Val Asn Gln Ser Ser Val Gln Val Val Leu
            260                 265                 270

Leu Phe Ala Ser Val His Ala Ala His Ala Leu Phe Asn Tyr Ser Ile
        275                 280                 285

Ser Ser Arg Leu Ser Pro Lys Val Trp Val Ala Ser Glu Ala Trp Leu
    290                 295                 300
```

-continued

```
Thr Ser Asp Leu Val Met Gly Leu Pro Gly Met Ala Gln Met Gly Thr
305                 310                 315                 320
Val Leu Gly Phe Leu Gln Arg Gly Ala Gln Leu His Glu Phe Pro Gln
                325                 330                 335
Tyr Val Lys Thr His Leu Ala Leu Ala Thr Asp Pro Ala Phe Cys Ser
            340                 345                 350
Ala Leu Gly Glu Arg Glu Gln Gly Leu Glu Glu Asp Val Val Gly Gln
        355                 360                 365
Arg Cys Pro Gln Cys Asp Cys Ile Thr Leu Gln Asn Val Ser Ala Gly
    370                 375                 380
Leu Asn His His Gln Thr Phe Ser Val Tyr Ala Val Tyr Ser Val
385                 390                 395                 400
Ala Gln Ala Leu His Asn Thr Leu Gln Cys Asn Ala Ser Gly Cys Pro
                405                 410                 415
Ala Gln Asp Pro Val Lys Pro Trp Gln Leu Leu Glu Asn Met Tyr Asn
            420                 425                 430
Leu Thr Phe His Val Gly Gly Leu Pro Leu Arg Phe Asp Ser Ser Gly
        435                 440                 445
Asn Val Asp Met Glu Tyr Asp Leu Lys Leu Trp Val Trp Gln Gly Ser
    450                 455                 460
Val Pro Arg Leu His Asp Val Gly Arg Phe Asn Gly Ser Leu Arg Thr
465                 470                 475                 480
Glu Arg Leu Lys Ile Arg Trp His Thr Ser Asp Asn Gln Lys Pro Val
                485                 490                 495
Ser Arg Cys Ser Arg Gln Cys Gln Glu Gly Gln Val Arg Val Lys
            500                 505                 510
Gly Phe His Ser Cys Cys Tyr Asp Cys Val Asp Cys Glu Ala Gly Ser
        515                 520                 525
Tyr Arg Gln Asn Pro Asp Asp Ile Ala Cys Thr Phe Cys Gly Gln Asp
    530                 535                 540
Glu Trp Ser Pro Glu Arg Ser Thr Arg Cys Phe Arg Arg Ser Arg
545                 550                 555                 560
Phe Leu Ala Trp Gly Glu Pro Ala Val Leu Leu Leu Leu Leu Leu
                565                 570                 575
Ser Leu Ala Leu Gly Leu Val Leu Ala Ala Leu Gly Leu Phe Val His
            580                 585                 590
His Arg Asp Ser Pro Leu Val Gln Ala Ser Gly Gly Pro Leu Ala Cys
        595                 600                 605
Phe Gly Leu Val Cys Leu Gly Leu Val Cys Leu Ser Val Leu Leu Phe
    610                 615                 620
Pro Gly Gln Pro Ser Pro Ala Arg Cys Leu Ala Gln Gln Pro Leu Ser
625                 630                 635                 640
His Leu Pro Leu Thr Gly Cys Leu Ser Thr Leu Phe Leu Gln Ala Ala
                645                 650                 655
Glu Ile Phe Val Glu Ser Glu Leu Pro Leu Ser Trp Ala Asp Arg Leu
            660                 665                 670
Ser Gly Cys Leu Arg Gly Pro Trp Ala Trp Leu Val Val Leu Leu Ala
        675                 680                 685
Met Leu Val Glu Val Ala Leu Cys Thr Trp Tyr Leu Val Ala Phe Pro
    690                 695                 700
Pro Glu Val Val Thr Asp Trp His Met Leu Pro Thr Glu Ala Leu Val
705                 710                 715                 720
His Cys Arg Thr Arg Ser Trp Val Ser Phe Gly Leu Ala His Ala Thr
                725                 730                 735
```

```
Asn Ala Thr Leu Ala Phe Leu Cys Phe Leu Gly Thr Phe Leu Val Arg
            740                 745                 750
Ser Gln Pro Gly Arg Tyr Asn Arg Ala Arg Gly Leu Thr Phe Ala Met
        755                 760                 765
Leu Ala Tyr Phe Ile Thr Trp Val Ser Phe Val Pro Leu Leu Ala Asn
770                 775                 780
Val Gln Val Val Leu Arg Pro Ala Val Gln Met Gly Ala Leu Leu
785                 790                 795                 800
Cys Val Leu Gly Ile Leu Ala Ala Phe His Leu Pro Arg Cys Tyr Leu
                805                 810                 815
Leu Met Arg Gln Pro Gly Leu Asn Thr Pro Glu Phe Phe Leu Gly Gly
            820                 825                 830
Gly Pro Gly Asp Ala Gln Gly Gln Asn Asp Gly Asn Thr Gly Asn Gln
        835                 840                 845
Gly Lys His Glu
    850

<210> SEQ ID NO 13
<211> LENGTH: 2700
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(2700)

<400> SEQUENCE: 13 atg gca ttt tat agc tgc tgc tgg gtc ctc ttg gca ctc acc tgg cac    48
Met Ala Phe Tyr Ser Cys Cys Trp Val Leu Leu Ala Leu Thr Trp His
1               5                   10                  15 acc tct gcc tac ggg cca gac cag cga gcc caa aag aag ggg gac att    96
Thr Ser Ala Tyr Gly Pro Asp Gln Arg Ala Gln Lys Lys Gly Asp Ile
                20                  25                  30 atc ctt ggg ggg ctc ttt cct att cat ttt gga gta gca gct aaa gat   144
Ile Leu Gly Gly Leu Phe Pro Ile His Phe Gly Val Ala Ala Lys Asp
            35                  40                  45 caa gat ctc aaa tca agg ccg gag tct gtg gaa tgt atc agg tat aat   192
Gln Asp Leu Lys Ser Arg Pro Glu Ser Val Glu Cys Ile Arg Tyr Asn
        50                  55                  60 ttc cgt ggg ttt cgc tgg tta cag gct atg ata ttt gcc ata gag gag   240
Phe Arg Gly Phe Arg Trp Leu Gln Ala Met Ile Phe Ala Ile Glu Glu
65                  70                  75                  80 ata aac agc agc cca gcc ctt ctt ccc aac ttg acg ctg gga tac agg   288
Ile Asn Ser Ser Pro Ala Leu Leu Pro Asn Leu Thr Leu Gly Tyr Arg
                85                  90                  95 ata ttt gac act tgc aac acc gtt tct aag gcc ttg gaa gcc acc ctg   336
Ile Phe Asp Thr Cys Asn Thr Val Ser Lys Ala Leu Glu Ala Thr Leu
                100                 105                 110 agt ttt gtt gct caa aac aaa att gat tct ttg aac ctt gat gag ttc   384
Ser Phe Val Ala Gln Asn Lys Ile Asp Ser Leu Asn Leu Asp Glu Phe
            115                 120                 125 tgc aac tgc tca gag cac att ccc tct acg att gct gtg gtg gga gca   432
Cys Asn Cys Ser Glu His Ile Pro Ser Thr Ile Ala Val Val Gly Ala
        130                 135                 140 act ggc tca ggc gtc tcc acg gca gtg gca aat ctg ctg ggg ctc ttc   480
Thr Gly Ser Gly Val Ser Thr Ala Val Ala Asn Leu Leu Gly Leu Phe
145                 150                 155                 160 tac att ccc cag gtc agt tat gcc tcc tcc agc aga ctc ctc agc aac   528
```

-continued

```
                Tyr Ile Pro Gln Val Ser Tyr Ala Ser Ser Ser Arg Leu Leu Ser Asn
                                165                 170                 175 aag aat caa ttc aag tct ttc ctc cga acc atc ccc aat gat gag cac          576
Lys Asn Gln Phe Lys Ser Phe Leu Arg Thr Ile Pro Asn Asp Glu His
            180                 185                 190 cag gcc act gcc atg gca gac atc atc gag tat ttc cgc tgg aac tgg          624
Gln Ala Thr Ala Met Ala Asp Ile Ile Glu Tyr Phe Arg Trp Asn Trp
        195                 200                 205 gtg ggc aca att gca gct gat gac gac tat ggg cgg ccg ggg att gag          672
Val Gly Thr Ile Ala Ala Asp Asp Asp Tyr Gly Arg Pro Gly Ile Glu
    210                 215                 220 aaa ttc cga gag gaa gct gag gaa agg gat atc tgc atc gac ttc agt          720
Lys Phe Arg Glu Glu Ala Glu Glu Arg Asp Ile Cys Ile Asp Phe Ser
225                 230                 235                 240 gaa ctc atc tcc cag tac tct gat gag gaa gag atc cag cat gtg gta          768
Glu Leu Ile Ser Gln Tyr Ser Asp Glu Glu Glu Ile Gln His Val Val
                245                 250                 255 gag gtg att caa aat tcc acg gcc aaa gtc atc gtg gtt ttc tcc agt          816
Glu Val Ile Gln Asn Ser Thr Ala Lys Val Ile Val Val Phe Ser Ser
            260                 265                 270 ggc cca gat ctt gag ccc ctc atc aag gag att gtc cgg cgc aat atc          864
Gly Pro Asp Leu Glu Pro Leu Ile Lys Glu Ile Val Arg Arg Asn Ile
        275                 280                 285 acg ggc aag atc tgg ctg gcc agc gag gcc tgg gcc agc tcc tcc ctg          912
Thr Gly Lys Ile Trp Leu Ala Ser Glu Ala Trp Ala Ser Ser Ser Leu
    290                 295                 300 atc gcc atg cct cag tac ttc cac gtg gtt ggc ggc acc att gga ttc          960
Ile Ala Met Pro Gln Tyr Phe His Val Val Gly Gly Thr Ile Gly Phe
305                 310                 315                 320 gct ctg aag gct ggg cag atc cca ggc ttc cgg gaa ttc ctg aag aag         1008
Ala Leu Lys Ala Gly Gln Ile Pro Gly Phe Arg Glu Phe Leu Lys Lys
                325                 330                 335 gtc cat ccc agg aag tct gtc cac aat ggt ttt gcc aag gag ttt tgg         1056
Val His Pro Arg Lys Ser Val His Asn Gly Phe Ala Lys Glu Phe Trp
            340                 345                 350 gaa gaa aca ttt aac tgc cac ctc caa gaa ggt gca aaa gga cct tta         1104
Glu Glu Thr Phe Asn Cys His Leu Gln Glu Gly Ala Lys Gly Pro Leu
        355                 360                 365 cct gtg gac acc ttt ctg aga ggt cac gaa gaa agt ggc gac agg ttt         1152
Pro Val Asp Thr Phe Leu Arg Gly His Glu Glu Ser Gly Asp Arg Phe
    370                 375                 380 agc aac agc tcg aca gcc ttc cga ccc ctc tgt aca ggg gat gag aac         1200
Ser Asn Ser Ser Thr Ala Phe Arg Pro Leu Cys Thr Gly Asp Glu Asn
385                 390                 395                 400 atc agc agt gtc gag acc cct tac ata gat tac acg cat tta cgg ata         1248
Ile Ser Ser Val Glu Thr Pro Tyr Ile Asp Tyr Thr His Leu Arg Ile
                405                 410                 415 tcc tac aat gtg tac tta gca gtc tac tcc att gcc cac gcc ttg caa         1296
Ser Tyr Asn Val Tyr Leu Ala Val Tyr Ser Ile Ala His Ala Leu Gln
            420                 425                 430 gat ata tat acc tgc tta cct ggg aga ggg ctc ttc acc aat ggc tcc         1344
Asp Ile Tyr Thr Cys Leu Pro Gly Arg Gly Leu Phe Thr Asn Gly Ser
        435                 440                 445 tgt gca gac atc aag aaa gtt gag gcg tgg cag gtc ctg aag cac cta         1392
Cys Ala Asp Ile Lys Lys Val Glu Ala Trp Gln Val Leu Lys His Leu
    450                 455                 460 cgg cat cta aac ttt aca aac aat atg ggg gag cag gtg acc ttt gat         1440
Arg His Leu Asn Phe Thr Asn Asn Met Gly Glu Gln Val Thr Phe Asp
465                 470                 475                 480 gag tgt ggt gac ctg gtg ggg aac tat tcc atc atc aac tgg cac ctc         1488
```

|  |  |  |  |  |  |  |  |  |  |  |
|---|---|---|---|---|---|---|---|---|---|---|
| Glu | Cys | Gly | Asp | Leu | Val | Gly | Asn | Tyr | Ser | Ile | Ile | Asn | Trp | His | Leu |
|  |  |  |  | 485 |  |  |  | 490 |  |  |  | 495 |  |  |  |

```
tcc cca gag gat ggc tcc atc gtg ttt aag gaa gtc ggg tat tac aac      1536
Ser Pro Glu Asp Gly Ser Ile Val Phe Lys Glu Val Gly Tyr Tyr Asn
            500                 505                 510 gtc tat gcc aag aag gga gaa aga ctc ttc atc aac gag gag aaa atc      1584
Val Tyr Ala Lys Lys Gly Glu Arg Leu Phe Ile Asn Glu Glu Lys Ile
            515                 520                 525 ctg tgg agt ggg ttc tcc agg gag gtg ccg cgg tcc atg tgt tcc aag      1632
Leu Trp Ser Gly Phe Ser Arg Glu Val Pro Arg Ser Met Cys Ser Lys
        530                 535                 540 agg tgc cag tca ggg caa aag aag aag cct gtg ggc atc cac gtc tgc      1680
Arg Cys Gln Ser Gly Gln Lys Lys Lys Pro Val Gly Ile His Val Cys
545                 550                 555                 560 tgc ttc gag tgc atc gac tgc ctt ccc ggc acc ttc ctc aac cac act      1728
Cys Phe Glu Cys Ile Asp Cys Leu Pro Gly Thr Phe Leu Asn His Thr
                565                 570                 575 gaa gat gaa tat gaa tgc cag gcc tgc ccg aat aac gag tgg tcc tac      1776
Glu Asp Glu Tyr Glu Cys Gln Ala Cys Pro Asn Asn Glu Trp Ser Tyr
            580                 585                 590 cag agt gag acc tcc tgc ttc aag cgg cag ctg gtc ttc ctg gaa tgg      1824
Gln Ser Glu Thr Ser Cys Phe Lys Arg Gln Leu Val Phe Leu Glu Trp
        595                 600                 605 cat gag gca ccc acc atc gct gtg gcc ctg ctg gcc gcc ctg ggc ttc      1872
His Glu Ala Pro Thr Ile Ala Val Ala Leu Leu Ala Ala Leu Gly Phe
    610                 615                 620 ctc agc acc ctg gcc atc ctg gtg ata ttc tgg agg cac ttc cag aca      1920
Leu Ser Thr Leu Ala Ile Leu Val Ile Phe Trp Arg His Phe Gln Thr
625                 630                 635                 640 ccc ata gtt cgc tcg gct ggg ggc ccc atg tgc ttc ctg atg ctg aca      1968
Pro Ile Val Arg Ser Ala Gly Gly Pro Met Cys Phe Leu Met Leu Thr
                645                 650                 655 ctg ctg ctg gtg gca tac atg gtg gtc ccg gtg tac gtg ggg ccg ccc      2016
Leu Leu Leu Val Ala Tyr Met Val Val Pro Val Tyr Val Gly Pro Pro
            660                 665                 670 aag gtc tcc acc tgc ctc tgc cgc cag gcc ctc ttt ccc ctc tgc ttc      2064
Lys Val Ser Thr Cys Leu Cys Arg Gln Ala Leu Phe Pro Leu Cys Phe
        675                 680                 685 aca atc tgc atc tcc tgt atc gcc gtg cgt tct ttc cag atc gtc tgc      2112
Thr Ile Cys Ile Ser Cys Ile Ala Val Arg Ser Phe Gln Ile Val Cys
    690                 695                 700 gcc ttc aag atg gcc agc cgc ttc cca cgc gcc tac agc tac tgg gtc      2160
Ala Phe Lys Met Ala Ser Arg Phe Pro Arg Ala Tyr Ser Tyr Trp Val
705                 710                 715                 720 cgc tac cag ggg ccc tac gtc tct atg gca ttt atc acg gta ctc aaa      2208
Arg Tyr Gln Gly Pro Tyr Val Ser Met Ala Phe Ile Thr Val Leu Lys
                725                 730                 735 atg gtc att gtg gta att ggc atg ctg gcc acg ggc ctc agt ccc acc      2256
Met Val Ile Val Val Ile Gly Met Leu Ala Thr Gly Leu Ser Pro Thr
            740                 745                 750 acc cgt act gac ccc gat gac ccc aag atc aca att gtc tcc tgt aac      2304
Thr Arg Thr Asp Pro Asp Asp Pro Lys Ile Thr Ile Val Ser Cys Asn
        755                 760                 765 ccc aac tac cgc aac agc ctg ctg ttc aac acc agc ctg gac ctg ctg      2352
Pro Asn Tyr Arg Asn Ser Leu Leu Phe Asn Thr Ser Leu Asp Leu Leu
    770                 775                 780 ctc tca gtg gtg ggt ttc agc ttc gcc tac atg ggc aaa gag ctg ccc      2400
Leu Ser Val Val Gly Phe Ser Phe Ala Tyr Met Gly Lys Glu Leu Pro
785                 790                 795                 800 acc aac tac aac gag gcc aag ttc atc acc ctc agc atg acc ttc tat      2448
```

```
                Thr Asn Tyr Asn Glu Ala Lys Phe Ile Thr Leu Ser Met Thr Phe Tyr
                                805                 810                 815 ttc acc tca tct gtc tcc ctc tgc acc ttc atg tct gcc tac agc ggg          2496
Phe Thr Ser Ser Val Ser Leu Cys Thr Phe Met Ser Ala Tyr Ser Gly
            820                 825                 830 gtg ctg gtc acc atc gtg gac ctc ttg gtc act gtg ctc aac ctc ctg          2544
Val Leu Val Thr Ile Val Asp Leu Leu Val Thr Val Leu Asn Leu Leu
        835                 840                 845 gcc atc agc ctg ggc tac ttc ggc ccc aag tgc tac atg atc ctc ttc          2592
Ala Ile Ser Leu Gly Tyr Phe Gly Pro Lys Cys Tyr Met Ile Leu Phe
    850                 855                 860 tac ccg gag cgc aac acg ccc gcc tac ttc aac agc atg atc cag ggc          2640
Tyr Pro Glu Arg Asn Thr Pro Ala Tyr Phe Asn Ser Met Ile Gln Gly
865                 870                 875                 880 tac acc atg agg agg gac tgc ggc cgc cag cct gaa ctc gct cct gaa          2688
Tyr Thr Met Arg Arg Asp Cys Gly Arg Gln Pro Glu Leu Ala Pro Glu
                885                 890                 895 gac ccg gaa gat                                                          2700
Asp Pro Glu Asp
            900

<210> SEQ ID NO 14
<211> LENGTH: 900
<212> TYPE: PRT
<213> ORGANISM: Artificial Sequence
<220> FEATURE:
<223> OTHER INFORMATION: Synthetic Construct

<400> SEQUENCE: 14

Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Tyr Gly Arg Pro Gly Ile Glu
    210                 215                 220

Lys Phe Arg Glu Glu Ala Glu Glu Arg Asp Ile Cys Ile Asp Phe Ser
```

-continued

```
             225                 230                 235                 240
Glu Leu Ile Ser Gln Tyr Ser Asp Glu Glu Ile Gln His Val Val
                 245                 250                 255
Glu Val Ile Gln Asn Ser Thr Ala Lys Val Ile Val Phe Ser Ser
             260                 265                 270
Gly Pro Asp Leu Glu Pro Leu Ile Lys Glu Ile Val Arg Arg Asn Ile
             275                 280                 285
Thr Gly Lys Ile Trp Leu Ala Ser Glu Ala Trp Ala Ser Ser Ser Leu
         290                 295                 300
Ile Ala Met Pro Gln Tyr Phe His Val Val Gly Gly Thr Ile Gly Phe
305                 310                 315                 320
Ala Leu Lys Ala Gly Gln Ile Pro Gly Phe Arg Glu Phe Leu Lys Lys
                 325                 330                 335
Val His Pro Arg Lys Ser Val His Asn Gly Phe Ala Lys Glu Phe Trp
             340                 345                 350
Glu Glu Thr Phe Asn Cys His Leu Gln Glu Gly Ala Lys Gly Pro Leu
         355                 360                 365
Pro Val Asp Thr Phe Leu Arg Gly His Glu Glu Ser Gly Asp Arg Phe
     370                 375                 380
Ser Asn Ser Ser Thr Ala Phe Arg Pro Leu Cys Thr Gly Asp Glu Asn
385                 390                 395                 400
Ile Ser Ser Val Glu Thr Pro Tyr Ile Asp Tyr Thr His Leu Arg Ile
                 405                 410                 415
Ser Tyr Asn Val Tyr Leu Ala Val Tyr Ser Ile Ala His Ala Leu Gln
             420                 425                 430
Asp Ile Tyr Thr Cys Leu Pro Gly Arg Gly Leu Phe Thr Asn Gly Ser
         435                 440                 445
Cys Ala Asp Ile Lys Lys Val Glu Ala Trp Gln Val Leu Lys His Leu
     450                 455                 460
Arg His Leu Asn Phe Thr Asn Asn Met Gly Glu Gln Val Thr Phe Asp
465                 470                 475                 480
Glu Cys Gly Asp Leu Val Gly Asn Tyr Ser Ile Ile Asn Trp His Leu
                 485                 490                 495
Ser Pro Glu Asp Gly Ser Ile Val Phe Lys Glu Val Gly Tyr Tyr Asn
             500                 505                 510
Val Tyr Ala Lys Lys Gly Glu Arg Leu Phe Ile Asn Glu Glu Lys Ile
         515                 520                 525
Leu Trp Ser Gly Phe Ser Arg Glu Val Pro Arg Ser Met Cys Ser Lys
     530                 535                 540
Arg Cys Gln Ser Gly Gln Lys Lys Lys Pro Val Gly Ile His Val Cys
545                 550                 555                 560
Cys Phe Glu Cys Ile Asp Cys Leu Pro Gly Thr Phe Leu Asn His Thr
                 565                 570                 575
Glu Asp Glu Tyr Glu Cys Gln Ala Cys Pro Asn Asn Glu Trp Ser Tyr
             580                 585                 590
Gln Ser Glu Thr Ser Cys Phe Lys Arg Gln Leu Val Phe Leu Glu Trp
         595                 600                 605
His Glu Ala Pro Thr Ile Ala Val Ala Leu Leu Ala Ala Leu Gly Phe
     610                 615                 620
Leu Ser Thr Leu Ala Ile Leu Val Ile Phe Trp Arg His Phe Gln Thr
625                 630                 635                 640
Pro Ile Val Arg Ser Ala Gly Gly Pro Met Cys Phe Leu Met Leu Thr
                 645                 650                 655
```

```
Leu Leu Leu Val Ala Tyr Met Val Pro Val Tyr Val Gly Pro Pro
            660                 665                 670

Lys Val Ser Thr Cys Leu Cys Arg Gln Ala Leu Phe Pro Leu Cys Phe
    675                 680                 685

Thr Ile Cys Ile Ser Cys Ile Ala Val Arg Ser Phe Gln Ile Val Cys
690                 695                 700

Ala Phe Lys Met Ala Ser Arg Phe Pro Arg Ala Tyr Ser Tyr Trp Val
705                 710                 715                 720

Arg Tyr Gln Gly Pro Tyr Val Ser Met Ala Phe Ile Thr Val Leu Lys
                725                 730                 735

Met Val Ile Val Val Ile Gly Met Leu Ala Thr Gly Leu Ser Pro Thr
            740                 745                 750

Thr Arg Thr Asp Pro Asp Pro Lys Ile Thr Ile Val Ser Cys Asn
    755                 760                 765

Pro Asn Tyr Arg Asn Ser Leu Leu Phe Asn Thr Ser Leu Asp Leu Leu
770                 775                 780

Leu Ser Val Val Gly Phe Ser Phe Ala Tyr Met Gly Lys Glu Leu Pro
785                 790                 795                 800

Thr Asn Tyr Asn Glu Ala Lys Phe Ile Thr Leu Ser Met Thr Phe Tyr
                805                 810                 815

Phe Thr Ser Ser Val Ser Leu Cys Thr Phe Met Ser Ala Tyr Ser Gly
            820                 825                 830

Val Leu Val Thr Ile Val Asp Leu Leu Val Thr Val Leu Asn Leu Leu
    835                 840                 845

Ala Ile Ser Leu Gly Tyr Phe Gly Pro Lys Cys Tyr Met Ile Leu Phe
850                 855                 860

Tyr Pro Glu Arg Asn Thr Pro Ala Tyr Phe Asn Ser Met Ile Gln Gly
865                 870                 875                 880

Tyr Thr Met Arg Arg Asp Cys Gly Arg Gln Pro Glu Leu Ala Pro Glu
                885                 890                 895

Asp Pro Glu Asp
            900

<210> SEQ ID NO 15
<211> LENGTH: 2727
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(2727)

<400> SEQUENCE: 15 atg gca ttt tat agc tgc tgc tgg gtc ctc ttg gca ctc acc tgg cac      48
Met Ala Phe Tyr Ser Cys Cys Trp Val Leu Leu Ala Leu Thr Trp His
1               5                   10                  15 acc tct gcc tac ggg cca gac cag cga gcc caa aag aag ggg gac att      96
Thr Ser Ala Tyr Gly Pro Asp Gln Arg Ala Gln Lys Lys Gly Asp Ile
            20                  25                  30 atc ctt ggg ggg ctc ttt cct att cat ttt gga gta gca gct aaa gat     144
Ile Leu Gly Gly Leu Phe Pro Ile His Phe Gly Val Ala Ala Lys Asp
        35                  40                  45 caa gat ctc aaa tca agg ccg gag tct gtg gaa tgt atc agg tat aat     192
Gln Asp Leu Lys Ser Arg Pro Glu Ser Val Glu Cys Ile Arg Tyr Asn
    50                  55                  60 ttc cgt ggg ttt cgc tgg tta cag gct atg ata ttt gcc ata gag gag     240
Phe Arg Gly Phe Arg Trp Leu Gln Ala Met Ile Phe Ala Ile Glu Glu
```

```
                65                  70                  75                  80
ata aac agc agc cca gcc ctt ctt ccc aac ttg acg ctg gga tac agg      288
Ile Asn Ser Ser Pro Ala Leu Leu Pro Asn Leu Thr Leu Gly Tyr Arg
                    85                  90                  95 ata ttt gac act tgc aac acc gtt tct aag gcc ttg gaa gcc acc ctg      336
Ile Phe Asp Thr Cys Asn Thr Val Ser Lys Ala Leu Glu Ala Thr Leu
                100                 105                 110 agt ttt gtt gct caa aac aaa att gat tct ttg aac ctt gat gag ttc      384
Ser Phe Val Ala Gln Asn Lys Ile Asp Ser Leu Asn Leu Asp Glu Phe
                115                 120                 125 tgc aac tgc tca gag cac att ccc tct acg att gct gtg gtg gga gca      432
Cys Asn Cys Ser Glu His Ile Pro Ser Thr Ile Ala Val Val Gly Ala
130                 135                 140 act ggc tca ggc gtc tcc acg gca gtg gca aat ctg ctg ggg ctc ttc      480
Thr Gly Ser Gly Val Ser Thr Ala Val Ala Asn Leu Leu Gly Leu Phe
145                 150                 155                 160 tac att ccc cag gtc agt tat gcc tcc tcc agc aga ctc ctc agc aac      528
Tyr Ile Pro Gln Val Ser Tyr Ala Ser Ser Ser Arg Leu Leu Ser Asn
                165                 170                 175 aag aat caa ttc aag tct ttc ctc cga acc atc ccc aat gat gag cac      576
Lys Asn Gln Phe Lys Ser Phe Leu Arg Thr Ile Pro Asn Asp Glu His
                180                 185                 190 cag gcc act gcc atg gca gac atc atc gag tat ttc cgc tgg aac tgg      624
Gln Ala Thr Ala Met Ala Asp Ile Ile Glu Tyr Phe Arg Trp Asn Trp
                195                 200                 205 gtg ggc aca att gca gct gat gac gac tat ggg cgg ccg ggg att gag      672
Val Gly Thr Ile Ala Ala Asp Asp Asp Tyr Gly Arg Pro Gly Ile Glu
210                 215                 220 aaa ttc cga gag gaa gct gag gaa agg gat atc tgc atc gac ttc agt      720
Lys Phe Arg Glu Glu Ala Glu Glu Arg Asp Ile Cys Ile Asp Phe Ser
225                 230                 235                 240 gaa ctc atc tcc cag tac tct gat gag gaa gag atc cag cat gtg gta      768
Glu Leu Ile Ser Gln Tyr Ser Asp Glu Glu Glu Ile Gln His Val Val
                245                 250                 255 gag gtg att caa aat tcc acg gcc aaa gtc atc gtg gtt ttc tcc agt      816
Glu Val Ile Gln Asn Ser Thr Ala Lys Val Ile Val Val Phe Ser Ser
                260                 265                 270 ggc cca gat ctt gag ccc ctc atc aag gag att gtc cgg cgc aat atc      864
Gly Pro Asp Leu Glu Pro Leu Ile Lys Glu Ile Val Arg Arg Asn Ile
                275                 280                 285 acg ggc aag atc tgg ctg gcc agc gag gcc tgg gcc agc tcc tcc ctg      912
Thr Gly Lys Ile Trp Leu Ala Ser Glu Ala Trp Ala Ser Ser Ser Leu
                290                 295                 300 atc gcc atg cct cag tac ttc cac gtg gtt ggc ggc acc att gga ttc      960
Ile Ala Met Pro Gln Tyr Phe His Val Val Gly Gly Thr Ile Gly Phe
305                 310                 315                 320 gct ctg aag gct ggg cag atc cca ggc ttc cgg gaa ttc ctg aag aag     1008
Ala Leu Lys Ala Gly Gln Ile Pro Gly Phe Arg Glu Phe Leu Lys Lys
                325                 330                 335 gtc cat ccc agg aag tct gtc cac aat ggt ttt gcc aag gag ttt tgg     1056
Val His Pro Arg Lys Ser Val His Asn Gly Phe Ala Lys Glu Phe Trp
                340                 345                 350 gaa gaa aca ttt aac tgc cac ctc caa gaa ggt gca aaa gga cct tta     1104
Glu Glu Thr Phe Asn Cys His Leu Gln Glu Gly Ala Lys Gly Pro Leu
                355                 360                 365 cct gtg gac acc ttt ctg aga ggt cac gaa gaa agt ggc gac agg ttt     1152
Pro Val Asp Thr Phe Leu Arg Gly His Glu Glu Ser Gly Asp Arg Phe
370                 375                 380 agc aac agc tcg aca gcc ttc cga ccc ctc tgt aca ggg gat gag aac     1200
Ser Asn Ser Ser Thr Ala Phe Arg Pro Leu Cys Thr Gly Asp Glu Asn
```

-continued

```
             385                 390                 395                 400
atc agc agt gtc gag acc cct tac ata gat tac acg cat tta cgg ata         1248
Ile Ser Ser Val Glu Thr Pro Tyr Ile Asp Tyr Thr His Leu Arg Ile
                405                 410                 415 tcc tac aat gtg tac tta gca gtc tac tcc att gcc cac gcc ttg caa         1296
Ser Tyr Asn Val Tyr Leu Ala Val Tyr Ser Ile Ala His Ala Leu Gln
            420                 425                 430 gat ata tat acc tgc tta cct ggg aga ggg ctc ttc acc aat ggc tcc         1344
Asp Ile Tyr Thr Cys Leu Pro Gly Arg Gly Leu Phe Thr Asn Gly Ser
            435                 440                 445 tgt gca gac atc aag aaa gtt gag gcg tgg cag gtc ctg aag cac cta         1392
Cys Ala Asp Ile Lys Lys Val Glu Ala Trp Gln Val Leu Lys His Leu
450                 455                 460 cgg cat cta aac ttt aca aac aat atg ggg gag cag gtg acc ttt gat         1440
Arg His Leu Asn Phe Thr Asn Asn Met Gly Glu Gln Val Thr Phe Asp
465                 470                 475                 480 gag tgt ggt gac ctg gtg ggg aac tat tcc atc atc aac tgg cac ctc         1488
Glu Cys Gly Asp Leu Val Gly Asn Tyr Ser Ile Ile Asn Trp His Leu
                485                 490                 495 tcc cca gag gat ggc tcc atc gtg ttt aag gaa gtc ggg tat tac aac         1536
Ser Pro Glu Asp Gly Ser Ile Val Phe Lys Glu Val Gly Tyr Tyr Asn
                500                 505                 510 gtc tat gcc aag aag gga gaa aga ctc ttc atc aac gag gag aaa atc         1584
Val Tyr Ala Lys Lys Gly Glu Arg Leu Phe Ile Asn Glu Glu Lys Ile
            515                 520                 525 ctg tgg agt ggg ttc tcc agg gag gtg ccg cgg tcc cgg tgc tcg cgg         1632
Leu Trp Ser Gly Phe Ser Arg Glu Val Pro Arg Ser Arg Cys Ser Arg
530                 535                 540 cag tgc cag gag ggc cag gtg cgc cgg gtc aag ggg ttc cac tcc tgc         1680
Gln Cys Gln Glu Gly Gln Val Arg Arg Val Lys Gly Phe His Ser Cys
545                 550                 555                 560 tgc tac gac tgt gtg gac tgc gag gcg ggc agc tac cgg caa aac cca         1728
Cys Tyr Asp Cys Val Asp Cys Glu Ala Gly Ser Tyr Arg Gln Asn Pro
                565                 570                 575 gac gac atc gcc tgc acc ttt tgt ggc cag gat gag tgg tcc ccg gag         1776
Asp Asp Ile Ala Cys Thr Phe Cys Gly Gln Asp Glu Trp Ser Pro Glu
                580                 585                 590 cga agc aca cgc tgc ttc cgc cgc agg tct cgg ttc ctg gca tgg ggc         1824
Arg Ser Thr Arg Cys Phe Arg Arg Arg Ser Arg Phe Leu Ala Trp Gly
            595                 600                 605 gag ccg gct gtg ctg ctg ctc ctg ctg agc ctg gcg ctg ggc                 1872
Glu Pro Ala Val Leu Leu Leu Leu Leu Ser Leu Ala Leu Gly
610                 615                 620 ctt gtg ctg gct gct ttg ggg ctg ttc gtt cac cat cgg gac agc cca         1920
Leu Val Leu Ala Ala Leu Gly Leu Phe Val His His Arg Asp Ser Pro
625                 630                 635                 640 ctg gtt cag gcc tcg ggg ggc ccc ctg gcc tgc ttt ggc ctg gtg tgc         1968
Leu Val Gln Ala Ser Gly Gly Pro Leu Ala Cys Phe Gly Leu Val Cys
                645                 650                 655 ctg ggc ctg gtc tgc ctc agc gtc ctc ctg ttc cct ggc cag ccc agc         2016
Leu Gly Leu Val Cys Leu Ser Val Leu Leu Phe Pro Gly Gln Pro Ser
                660                 665                 670 cct gcc cga tgc ctg gcc cag cag ccc ttg tcc cac ctc ccg ctc acg         2064
Pro Ala Arg Cys Leu Ala Gln Gln Pro Leu Ser His Leu Pro Leu Thr
                675                 680                 685 ggc tgc ctg agc aca ctc ttc ctg cag gcg gcc gag atc ttc gtg gag         2112
Gly Cys Leu Ser Thr Leu Phe Leu Gln Ala Ala Glu Ile Phe Val Glu
690                 695                 700 tca gaa ctg cct ctg agc tgg gca gac cgg ctg agt ggc tgc ctg cgg         2160
Ser Glu Leu Pro Leu Ser Trp Ala Asp Arg Leu Ser Gly Cys Leu Arg
```

```
                                                  705                 710                 715                 720
ggg ccc tgg gcc tgg ctg gtg gtg ctg ctg gcc atg ctg gtg gag gtc       2208
Gly Pro Trp Ala Trp Leu Val Val Leu Leu Ala Met Leu Val Glu Val
                    725                 730                 735 gca ctg tgc acc tgg tac ctg gtg gcc ttc ccg ccg gag gtg gtg acg       2256
Ala Leu Cys Thr Trp Tyr Leu Val Ala Phe Pro Pro Glu Val Val Thr
            740                 745                 750 gac tgg cac atg ctg ccc acg gag gcg ctg gtg cac tgc cgc aca cgc       2304
Asp Trp His Met Leu Pro Thr Glu Ala Leu Val His Cys Arg Thr Arg
        755                 760                 765 tcc tgg gtc agc ttc ggc cta gcg cac gcc acc aat gcc acg ctg gcc       2352
Ser Trp Val Ser Phe Gly Leu Ala His Ala Thr Asn Ala Thr Leu Ala
    770                 775                 780 ttt ctc tgc ttc ctg ggc act ttc ctg gtg cgg agc cag ccg ggc cgc       2400
Phe Leu Cys Phe Leu Gly Thr Phe Leu Val Arg Ser Gln Pro Gly Arg
785                 790                 795                 800 tac aac cgt gcc cgt ggc ctc acc ttt gcc atg ctg gcc tac ttc atc       2448
Tyr Asn Arg Ala Arg Gly Leu Thr Phe Ala Met Leu Ala Tyr Phe Ile
                805                 810                 815 acc tgg gtc tcc ttt gtg ccc ctc ctg gcc aat gtg cag gtg gtc ctc       2496
Thr Trp Val Ser Phe Val Pro Leu Leu Ala Asn Val Gln Val Val Leu
            820                 825                 830 agg ccc gcc gtg cag atg ggc gcc ctc ctg ctc tgt gtc ctg ggc atc       2544
Arg Pro Ala Val Gln Met Gly Ala Leu Leu Leu Cys Val Leu Gly Ile
        835                 840                 845 ctg gct gcc ttc cac ctg ccc agg tgt tac ctg ctc atg cgg cag cca       2592
Leu Ala Ala Phe His Leu Pro Arg Cys Tyr Leu Leu Met Arg Gln Pro
    850                 855                 860 ggg ctc aac acc ccc gag ttc ttc ctg gga ggg ggc cct ggg gat gcc       2640
Gly Leu Asn Thr Pro Glu Phe Phe Leu Gly Gly Gly Pro Gly Asp Ala
865                 870                 875                 880 caa ggc cag aat gac ggg aac aca gga aat cag ggg aaa cat gag tgc       2688
Gln Gly Gln Asn Asp Gly Asn Thr Gly Asn Gln Gly Lys His Glu Cys
                885                 890                 895 ggc cgc cag cct gaa ctc gct cct gaa gac ccg gaa gat                   2727
Gly Arg Gln Pro Glu Leu Ala Pro Glu Asp Pro Glu Asp
            900                 905

<210> SEQ ID NO 16
<211> LENGTH: 909
<212> TYPE: PRT
<213> ORGANISM: Artificial Sequence
<220> FEATURE:
<223> OTHER INFORMATION: Synthetic Construct

<400> SEQUENCE: 16

Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110
```

```
Ser Phe Val Ala Gln Asn Lys Ile Asp Ser Leu Asn Leu Asp Glu Phe
            115                 120                 125

Cys Asn Cys Ser Glu His Ile Pro Ser Thr Ile Ala Val Val Gly Ala
            130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                    165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
            195                 200                 205

Val Gly Thr Ile Ala Ala Asp Asp Tyr Gly Arg Pro Gly Ile Glu
            210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
                    245                 250                 255

Glu Val Ile Gln Asn Ser Thr Ala Lys Val Ile Val Val Phe Ser Ser
            260                 265                 270

Gly Pro Asp Leu Glu Pro Leu Ile Lys Glu Ile Val Arg Arg Asn Ile
            275                 280                 285

Thr Gly Lys Ile Trp Leu Ala Ser Glu Ala Trp Ala Ser Ser Ser Leu
            290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
                    325                 330                 335

Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
            355                 360                 365

Pro Val Asp Thr Phe Leu Arg Gly His Glu Glu Ser Gly Asp Arg Phe
            370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                    405                 410                 415

Ser Tyr Asn Val Tyr Leu Ala Val Tyr Ser Ile Ala His Ala Leu Gln
            420                 425                 430

Asp Ile Tyr Thr Cys Leu Pro Gly Arg Gly Leu Phe Thr Asn Gly Ser
            435                 440                 445

Cys Ala Asp Ile Lys Lys Val Glu Ala Trp Gln Val Leu Lys His Leu
450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                    485                 490                 495

Ser Pro Glu Asp Gly Ser Ile Val Phe Lys Val Gly Val Tyr Tyr Asn
            500                 505                 510

Val Tyr Ala Lys Lys Gly Glu Arg Leu Phe Ile Asn Glu Glu Lys Ile
            515                 520                 525

Leu Trp Ser Gly Phe Ser Arg Glu Val Pro Arg Ser Arg Cys Ser Arg
```

```
                530                 535                 540

Gln Cys Gln Glu Gly Gln Val Arg Arg Val Lys Gly Phe His Ser Cys
545                 550                 555                 560

Cys Tyr Asp Cys Val Asp Cys Glu Ala Gly Ser Tyr Arg Gln Asn Pro
                565                 570                 575

Asp Asp Ile Ala Cys Thr Phe Cys Gly Gln Asp Glu Trp Ser Pro Glu
            580                 585                 590

Arg Ser Thr Arg Cys Phe Arg Arg Ser Arg Phe Leu Ala Trp Gly
        595                 600                 605

Glu Pro Ala Val Leu Leu Leu Leu Leu Leu Ser Leu Ala Leu Gly
610                 615                 620

Leu Val Leu Ala Ala Leu Gly Leu Phe Val His His Arg Asp Ser Pro
625                 630                 635                 640

Leu Val Gln Ala Ser Gly Gly Pro Leu Ala Cys Phe Gly Leu Val Cys
                645                 650                 655

Leu Gly Leu Val Cys Leu Ser Val Leu Leu Phe Pro Gly Gln Pro Ser
            660                 665                 670

Pro Ala Arg Cys Leu Ala Gln Gln Pro Leu Ser His Leu Pro Leu Thr
        675                 680                 685

Gly Cys Leu Ser Thr Leu Phe Leu Gln Ala Ala Glu Ile Phe Val Glu
690                 695                 700

Ser Glu Leu Pro Leu Ser Trp Ala Asp Arg Leu Ser Gly Cys Leu Arg
705                 710                 715                 720

Gly Pro Trp Ala Trp Leu Val Val Leu Leu Ala Met Leu Val Glu Val
                725                 730                 735

Ala Leu Cys Thr Trp Tyr Leu Val Ala Phe Pro Pro Glu Val Val Thr
            740                 745                 750

Asp Trp His Met Leu Pro Thr Glu Ala Leu Val His Cys Arg Thr Arg
        755                 760                 765

Ser Trp Val Ser Phe Gly Leu Ala His Ala Thr Asn Ala Thr Leu Ala
770                 775                 780

Phe Leu Cys Phe Leu Gly Thr Phe Leu Val Arg Ser Gln Pro Gly Arg
785                 790                 795                 800

Tyr Asn Arg Ala Arg Gly Leu Thr Phe Ala Met Leu Ala Tyr Phe Ile
                805                 810                 815

Thr Trp Val Ser Phe Val Pro Leu Leu Ala Asn Val Gln Val Val Leu
            820                 825                 830

Arg Pro Ala Val Gln Met Gly Ala Leu Leu Leu Cys Val Leu Gly Ile
        835                 840                 845

Leu Ala Ala Phe His Leu Pro Arg Cys Tyr Leu Leu Met Arg Gln Pro
850                 855                 860

Gly Leu Asn Thr Pro Glu Phe Phe Leu Gly Gly Gly Pro Gly Asp Ala
865                 870                 875                 880

Gln Gly Gln Asn Asp Gly Asn Thr Gly Asn Gln Gly Lys His Glu Cys
                885                 890                 895

Gly Arg Gln Pro Glu Leu Ala Pro Glu Asp Pro Glu Asp
            900                 905

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<221> NAME/KEY: CDS
<222> LOCATION: (1)..(42)

<400> SEQUENCE: 17

```
tgc ggc cgc cag cct gaa ctc gct cct gaa gac ccg gaa gat taa         45
Cys Gly Arg Gln Pro Glu Leu Ala Pro Glu Asp Pro Glu Asp
1               5                   10
```

<210> SEQ ID NO 18
<211> LENGTH: 14
<212> TYPE: PRT
<213> ORGANISM: Artificial Sequence
<220> FEATURE:
<223> OTHER INFORMATION: Synthetic Construct

<400> SEQUENCE: 18

```
Cys Gly Arg Gln Pro Glu Leu Ala Pro Glu Asp Pro Glu Asp
1               5                   10
```

<210> SEQ ID NO 19
<211> LENGTH: 2520
<212> TYPE: DNA
<213> ORGANISM: Homo sapiens
<220> FEATURE:
<221> NAME/KEY: CDS
<222> LOCATION: (1)..(2517)

<400> SEQUENCE: 19

```
atg ggg ccc agg gca aag acc atc tcc tcc ctg ttc ttc ctc cta tgg     48
Met Gly Pro Arg Ala Lys Thr Ile Ser Ser Leu Phe Phe Leu Leu Trp
1               5                   10                  15 gtc ctg gct gag ccg gct gag aac tcg gac ttc tac ctg cct ggg gat     96
Val Leu Ala Glu Pro Ala Glu Asn Ser Asp Phe Tyr Leu Pro Gly Asp
            20                  25                  30 tac ctc ctg ggt ggc ctc ttc tcc ctc cat gcc aac atg aag ggc att    144
Tyr Leu Leu Gly Gly Leu Phe Ser Leu His Ala Asn Met Lys Gly Ile
        35                  40                  45 gtt cac ctt aac ttc ctg cag gtg ccc atg tgc aag gag tat gaa gtg    192
Val His Leu Asn Phe Leu Gln Val Pro Met Cys Lys Glu Tyr Glu Val
    50                  55                  60 aag gtg ata ggc tac aac ctc atg cag gcc atg cgc ttt gcg gtg gag    240
Lys Val Ile Gly Tyr Asn Leu Met Gln Ala Met Arg Phe Ala Val Glu
65                  70                  75                  80 gag atc aac aat gac agc agc ctg ctg cct ggt gtg ctg ctg ggc tat    288
Glu Ile Asn Asn Asp Ser Ser Leu Leu Pro Gly Val Leu Leu Gly Tyr
                85                  90                  95 gag atc gtg gat gtg tgc tac atc tcc aac aat gtc cag ccg gtg ctc    336
Glu Ile Val Asp Val Cys Tyr Ile Ser Asn Asn Val Gln Pro Val Leu
            100                 105                 110 tac ttc ctg gca cac gag gac aac ctc ctt ccc atc caa gag gac tac    384
Tyr Phe Leu Ala His Glu Asp Asn Leu Leu Pro Ile Gln Glu Asp Tyr
        115                 120                 125 agt aac tac att tcc cgt gtg gtg gct gtc att ggc cct gac aac tcc    432
Ser Asn Tyr Ile Ser Arg Val Val Ala Val Ile Gly Pro Asp Asn Ser
    130                 135                 140 gag tct gtc atg act gtg gcc aac ttc ctc tcc cta ttt ctc ctt cca    480
Glu Ser Val Met Thr Val Ala Asn Phe Leu Ser Leu Phe Leu Leu Pro
145                 150                 155                 160 cag atc acc tac agc gcc atc agc gat gag ctg cga gac aag gtg cgc    528
Gln Ile Thr Tyr Ser Ala Ile Ser Asp Glu Leu Arg Asp Lys Val Arg
                165                 170                 175 ttc ccg gct ttg ctg cgt acc aca ccc agc gcc gac cac cac atc gag    576
Phe Pro Ala Leu Leu Arg Thr Thr Pro Ser Ala Asp His His Ile Glu
            180                 185                 190
```

-continued

| | |
|---|---|
| gcc atg gtg cag ctg atg ctg cac ttc cgc tgg aac tgg atc att gtg<br>Ala Met Val Gln Leu Met Leu His Phe Arg Trp Asn Trp Ile Ile Val<br>          195                  200                  205 | 624 |
| ctg gtg agc agc gac acc tat ggc cgc gac aat ggc cag ctg ctt ggc<br>Leu Val Ser Ser Asp Thr Tyr Gly Arg Asp Asn Gly Gln Leu Leu Gly<br>210                       215                     220 | 672 |
| gag cgc gtg gcc cgg cgc gac atc tgc atc gcc ttc cag gag acg ctg<br>Glu Arg Val Ala Arg Arg Asp Ile Cys Ile Ala Phe Gln Glu Thr Leu<br>225                     230                  235               240 | 720 |
| ccc aca ctg cag ccc aac cag aac atg acg tca gag gag cgc cag cgc<br>Pro Thr Leu Gln Pro Asn Gln Asn Met Thr Ser Glu Glu Arg Gln Arg<br>                    245                  250                  255 | 768 |
| ctg gtg acc att gtg gac aag ctg cag cag agc aca gcg cgc gtc gtg<br>Leu Val Thr Ile Val Asp Lys Leu Gln Gln Ser Thr Ala Arg Val Val<br>          260                  265                  270 | 816 |
| gtc gtg ttc tcg ccc gac ctg acc ctg tac cac ttc ttc aat gag gtg<br>Val Val Phe Ser Pro Asp Leu Thr Leu Tyr His Phe Phe Asn Glu Val<br>               275                  280                  285 | 864 |
| ctg cgc cag aac ttc act ggc gcc gtg tgg atc gcc tcc gag tcc tgg<br>Leu Arg Gln Asn Phe Thr Gly Ala Val Trp Ile Ala Ser Glu Ser Trp<br>290                     295                  300 | 912 |
| gcc atc gac ccg gtc ctg cac aac ctc acg gag ctg cgc cac ttg ggc<br>Ala Ile Asp Pro Val Leu His Asn Leu Thr Glu Leu Arg His Leu Gly<br>305                     310                  315               320 | 960 |
| acc ttc ctg ggc atc acc atc cag agc gtg ccc atc ccg ggc ttc agt<br>Thr Phe Leu Gly Ile Thr Ile Gln Ser Val Pro Ile Pro Gly Phe Ser<br>                    325                  330                  335 | 1008 |
| gag ttc cgc gag tgg ggc cca cag gct ggg ccg cca ccc ctc agc agg<br>Glu Phe Arg Glu Trp Gly Pro Gln Ala Gly Pro Pro Pro Leu Ser Arg<br>          340                  345                  350 | 1056 |
| acc agc cag agc tat acc tgc aac cag gag tgc gac aac tgc ctg aac<br>Thr Ser Gln Ser Tyr Thr Cys Asn Gln Glu Cys Asp Asn Cys Leu Asn<br>               355                  360                  365 | 1104 |
| gcc acc ttg tcc ttc aac acc att ctc agg ctc tct ggg gag cgt gtc<br>Ala Thr Leu Ser Phe Asn Thr Ile Leu Arg Leu Ser Gly Glu Arg Val<br>370                     375                  380 | 1152 |
| gtc tac agc gtg tac tct gcg gtc tat gct gtg gcc cat gcc ctg cac<br>Val Tyr Ser Val Tyr Ser Ala Val Tyr Ala Val Ala His Ala Leu His<br>385                     390                  395               400 | 1200 |
| agc ctc ctc ggc tgt gac aaa agc acc tgc acc aag agg gtg gtc tac<br>Ser Leu Leu Gly Cys Asp Lys Ser Thr Cys Thr Lys Arg Val Val Tyr<br>                    405                  410                  415 | 1248 |
| ccc tgg cag ctg ctt gag gag atc tgg aag gtc aac ttc act ctc ctg<br>Pro Trp Gln Leu Leu Glu Glu Ile Trp Lys Val Asn Phe Thr Leu Leu<br>          420                  425                  430 | 1296 |
| gac cac caa atc ttc ttc gac ccg caa ggg gac gtg gct ctg cac ttg<br>Asp His Gln Ile Phe Phe Asp Pro Gln Gly Asp Val Ala Leu His Leu<br>               435                  440                  445 | 1344 |
| gag att gtc cag tgg caa tgg gac cgg agc cag aat ccc ttc cag agc<br>Glu Ile Val Gln Trp Gln Trp Asp Arg Ser Gln Asn Pro Phe Gln Ser<br>450                     455                  460 | 1392 |
| gtc gcc tcc tac tac ccc ctg cag cga cag ctg aag aac atc caa gac<br>Val Ala Ser Tyr Tyr Pro Leu Gln Arg Gln Leu Lys Asn Ile Gln Asp<br>465                     470                  475               480 | 1440 |
| atc tcc tgg cac acc atc aac aac acg atc cct atg tcc atg tgt tcc<br>Ile Ser Trp His Thr Ile Asn Asn Thr Ile Pro Met Ser Met Cys Ser<br>                    485                  490                  495 | 1488 |
| aag agg tgc cag tca ggg caa aag aag aag cct gtg ggc atc cac gtc<br>Lys Arg Cys Gln Ser Gly Gln Lys Lys Lys Pro Val Gly Ile His Val<br>          500                  505                  510 | 1536 |

| | | |
|---|---|---|
| tgc tgc ttc gag tgc atc gac tgc ctt ccc ggc acc ttc ctc aac cac<br>Cys Cys Phe Glu Cys Ile Asp Cys Leu Pro Gly Thr Phe Leu Asn His<br>             515                     520                     525 | 1584 |
| act gaa gat gaa tat gaa tgc cag gcc tgc ccg aat aac gag tgg tcc<br>Thr Glu Asp Glu Tyr Glu Cys Gln Ala Cys Pro Asn Asn Glu Trp Ser<br>530                     535                     540 | 1632 |
| tac cag agt gag acc tcc tgc ttc aag cgg cag ctg gtc ttc ctg gaa<br>Tyr Gln Ser Glu Thr Ser Cys Phe Lys Arg Gln Leu Val Phe Leu Glu<br>545                     550                     555                     560 | 1680 |
| tgg cat gag gca ccc acc atc gct gtg gcc ctg ctg gcc gcc ctg ggc<br>Trp His Glu Ala Pro Thr Ile Ala Val Ala Leu Leu Ala Ala Leu Gly<br>             565                     570                     575 | 1728 |
| ttc ctc agc acc ctg gcc atc ctg gtg ata ttc tgg agg cac ttc cag<br>Phe Leu Ser Thr Leu Ala Ile Leu Val Ile Phe Trp Arg His Phe Gln<br>                     580                     585                     590 | 1776 |
| aca ccc ata gtt cgc tcg gct ggg ggc ccc atg tgc ttc ctg atg ctg<br>Thr Pro Ile Val Arg Ser Ala Gly Gly Pro Met Cys Phe Leu Met Leu<br>             595                     600                     605 | 1824 |
| aca ctg ctg ctg gtg gca tac atg gtg gtc ccg gtg tac gtg ggg ccg<br>Thr Leu Leu Leu Val Ala Tyr Met Val Val Pro Val Tyr Val Gly Pro<br>610                     615                     620 | 1872 |
| ccc aag gtc tcc acc tgc ctc tgc cgc cag gcc ctc ttt ccc ctc tgc<br>Pro Lys Val Ser Thr Cys Leu Cys Arg Gln Ala Leu Phe Pro Leu Cys<br>625                     630                     635                     640 | 1920 |
| ttc aca atc tgc atc tcc tgt atc gcc gtg cgt tct ttc cag atc gtc<br>Phe Thr Ile Cys Ile Ser Cys Ile Ala Val Arg Ser Phe Gln Ile Val<br>             645                     650                     655 | 1968 |
| tgc gcc ttc aag atg gcc agc cgc ttc cca cgc gcc tac agc tac tgg<br>Cys Ala Phe Lys Met Ala Ser Arg Phe Pro Arg Ala Tyr Ser Tyr Trp<br>                     660                     665                     670 | 2016 |
| gtc cgc tac cag ggg ccc tac gtc tct atg gca ttt atc acg gta ctc<br>Val Arg Tyr Gln Gly Pro Tyr Val Ser Met Ala Phe Ile Thr Val Leu<br>             675                     680                     685 | 2064 |
| aaa atg gtc att gtg gta att ggc atg ctg gcc acg ggc ctc agt ccc<br>Lys Met Val Ile Val Val Ile Gly Met Leu Ala Thr Gly Leu Ser Pro<br>690                     695                     700 | 2112 |
| acc acc cgt act gac ccc gat gac ccc aag atc aca att gtc tcc tgt<br>Thr Thr Arg Thr Asp Pro Asp Asp Pro Lys Ile Thr Ile Val Ser Cys<br>705                     710                     715                     720 | 2160 |
| aac ccc aac tac cgc aac agc ctg ctg ttc aac acc agc ctg gac ctg<br>Asn Pro Asn Tyr Arg Asn Ser Leu Leu Phe Asn Thr Ser Leu Asp Leu<br>                     725                     730                     735 | 2208 |
| ctg ctc tca gtg gtg ggt ttc agc ttc gcc tac atg ggc aaa gag ctg<br>Leu Leu Ser Val Val Gly Phe Ser Phe Ala Tyr Met Gly Lys Glu Leu<br>             740                     745                     750 | 2256 |
| ccc acc aac tac aac gag gcc aag ttc atc acc ctc agc atg acc ttc<br>Pro Thr Asn Tyr Asn Glu Ala Lys Phe Ile Thr Leu Ser Met Thr Phe<br>755                     760                     765 | 2304 |
| tat ttc acc tca tct gtc tcc ctc tgc acc ttc atg tct gcc tac agc<br>Tyr Phe Thr Ser Ser Val Ser Leu Cys Thr Phe Met Ser Ala Tyr Ser<br>770                     775                     780 | 2352 |
| ggg gtg ctg gtc acc atc gtg gac ctc ttg gtc act gtg ctc aac ctc<br>Gly Val Leu Val Thr Ile Val Asp Leu Leu Val Thr Val Leu Asn Leu<br>785                     790                     795                     800 | 2400 |
| ctg gcc atc agc ctg ggc tac ttc ggc ccc aag tgc tac atg atc ctc<br>Leu Ala Ile Ser Leu Gly Tyr Phe Gly Pro Lys Cys Tyr Met Ile Leu<br>                     805                     810                     815 | 2448 |
| ttc tac ccg gag cgc aac acg ccc gcc tac ttc aac agc atg atc cag<br>Phe Tyr Pro Glu Arg Asn Thr Pro Ala Tyr Phe Asn Ser Met Ile Gln<br>             820                     825                     830 | 2496 |

```
                                               ggc tac acc atg agg agg gac tag                            2520
                                               Gly Tyr Thr Met Arg Arg Asp
                                                       835

<210> SEQ ID NO 20
<211> LENGTH: 839
<212> TYPE: PRT
<213> ORGANISM: Homo sapiens

<400> SEQUENCE: 20

Met Gly Pro Arg Ala Lys Thr Ile Ser Ser Leu Phe Leu Leu Trp
1               5                   10                  15

Val Leu Ala Glu Pro Ala Glu Asn Ser Asp Phe Tyr Leu Pro Gly Asp
                20                  25                  30

Tyr Leu Leu Gly Gly Leu Phe Ser Leu His Ala Asn Met Lys Gly Ile
                35                  40                  45

Val His Leu Asn Phe Leu Gln Val Pro Met Cys Lys Glu Tyr Glu Val
50                  55                  60

Lys Val Ile Gly Tyr Asn Leu Met Gln Ala Met Arg Phe Ala Val Glu
65                  70                  75                  80

Glu Ile Asn Asn Asp Ser Ser Leu Leu Pro Gly Val Leu Leu Gly Tyr
                85                  90                  95

Glu Ile Val Asp Val Cys Tyr Ile Ser Asn Asn Val Gln Pro Val Leu
                100                 105                 110

Tyr Phe Leu Ala His Glu Asp Asn Leu Leu Pro Ile Gln Glu Asp Tyr
                115                 120                 125

Ser Asn Tyr Ile Ser Arg Val Val Ala Val Ile Gly Pro Asp Asn Ser
                130                 135                 140

Glu Ser Val Met Thr Val Ala Asn Phe Leu Ser Leu Phe Leu Leu Pro
145                 150                 155                 160

Gln Ile Thr Tyr Ser Ala Ile Ser Asp Glu Leu Arg Asp Lys Val Arg
                165                 170                 175

Phe Pro Ala Leu Leu Arg Thr Thr Pro Ser Ala Asp His His Ile Glu
                180                 185                 190

Ala Met Val Gln Leu Met Leu His Phe Arg Trp Asn Trp Ile Ile Val
                195                 200                 205

Leu Val Ser Ser Asp Thr Tyr Gly Arg Asp Asn Gly Gln Leu Leu Gly
                210                 215                 220

Glu Arg Val Ala Arg Arg Asp Ile Cys Ile Ala Phe Gln Glu Thr Leu
225                 230                 235                 240

Pro Thr Leu Gln Pro Asn Gln Asn Met Thr Ser Glu Glu Arg Gln Arg
                245                 250                 255

Leu Val Thr Ile Val Asp Lys Leu Gln Gln Ser Thr Ala Arg Val Val
                260                 265                 270

Val Val Phe Ser Pro Asp Leu Thr Leu Tyr His Phe Phe Asn Glu Val
                275                 280                 285

Leu Arg Gln Asn Phe Thr Gly Ala Val Trp Ile Ala Ser Glu Ser Trp
                290                 295                 300

Ala Ile Asp Pro Val Leu His Asn Leu Thr Glu Leu Arg His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Leu Ser Arg
                340                 345                 350

Thr Ser Gln Ser Tyr Thr Cys Asn Gln Glu Cys Asp Asn Cys Leu Asn
```

-continued

```
            355                 360                 365
Ala Thr Leu Ser Phe Asn Thr Ile Leu Arg Leu Ser Gly Glu Arg Val
            370                 375                 380
Val Tyr Ser Val Tyr Ser Ala Val Tyr Ala Val Ala His Ala Leu His
385                 390                 395                 400
Ser Leu Leu Gly Cys Asp Lys Ser Thr Cys Thr Lys Arg Val Val Tyr
                405                 410                 415
Pro Trp Gln Leu Glu Glu Ile Trp Lys Val Asn Phe Thr Leu Leu
                420                 425                 430
Asp His Gln Ile Phe Phe Asp Pro Gln Gly Asp Val Ala Leu His Leu
            435                 440                 445
Glu Ile Val Gln Trp Gln Trp Asp Arg Ser Gln Asn Pro Phe Gln Ser
        450                 455                 460
Val Ala Ser Tyr Tyr Pro Leu Gln Arg Gln Leu Lys Asn Ile Gln Asp
465                 470                 475                 480
Ile Ser Trp His Thr Ile Asn Asn Thr Ile Pro Met Ser Met Cys Ser
                485                 490                 495
Lys Arg Cys Gln Ser Gly Gln Lys Lys Lys Pro Val Gly Ile His Val
                500                 505                 510
Cys Cys Phe Glu Cys Ile Asp Cys Leu Pro Gly Thr Phe Leu Asn His
            515                 520                 525
Thr Glu Asp Glu Tyr Glu Cys Gln Ala Cys Pro Asn Asn Glu Trp Ser
        530                 535                 540
Tyr Gln Ser Glu Thr Ser Cys Phe Lys Arg Gln Leu Val Phe Leu Glu
545                 550                 555                 560
Trp His Glu Ala Pro Thr Ile Ala Val Ala Leu Leu Ala Ala Leu Gly
                565                 570                 575
Phe Leu Ser Thr Leu Ala Ile Leu Val Ile Phe Trp Arg His Phe Gln
            580                 585                 590
Thr Pro Ile Val Arg Ser Ala Gly Gly Pro Met Cys Phe Leu Met Leu
        595                 600                 605
Thr Leu Leu Leu Val Ala Tyr Met Val Val Pro Val Tyr Val Gly Pro
        610                 615                 620
Pro Lys Val Ser Thr Cys Leu Cys Arg Gln Ala Leu Phe Pro Leu Cys
625                 630                 635                 640
Phe Thr Ile Cys Ile Ser Cys Ile Ala Val Arg Ser Phe Gln Ile Val
                645                 650                 655
Cys Ala Phe Lys Met Ala Ser Arg Phe Pro Arg Ala Tyr Ser Tyr Trp
                660                 665                 670
Val Arg Tyr Gln Gly Pro Tyr Val Ser Met Ala Phe Ile Thr Val Leu
            675                 680                 685
Lys Met Val Ile Val Ile Gly Met Leu Ala Thr Gly Leu Ser Pro
        690                 695                 700
Thr Thr Arg Thr Asp Pro Asp Pro Lys Ile Thr Ile Val Ser Cys
705                 710                 715                 720
Asn Pro Asn Tyr Arg Asn Ser Leu Leu Phe Asn Thr Ser Leu Asp Leu
                725                 730                 735
Leu Leu Ser Val Val Gly Phe Ser Phe Ala Tyr Met Gly Lys Glu Leu
            740                 745                 750
Pro Thr Asn Tyr Asn Glu Ala Lys Phe Ile Thr Leu Ser Met Thr Phe
        755                 760                 765
Tyr Phe Thr Ser Ser Val Ser Leu Cys Thr Phe Met Ser Ala Tyr Ser
        770                 775                 780
```

```
Gly Val Leu Val Thr Ile Val Asp Leu Leu Val Thr Val Leu Asn Leu
785                 790                 795                 800

Leu Ala Ile Ser Leu Gly Tyr Phe Gly Pro Lys Cys Tyr Met Ile Leu
                805                 810                 815

Phe Tyr Pro Glu Arg Asn Thr Pro Ala Tyr Phe Asn Ser Met Ile Gln
            820                 825                 830

Gly Tyr Thr Met Arg Arg Asp
        835

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caccaagctt atggcatttt atagctgc                                      28

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atatccgcgg cacctccctg gagaaccc                                      28

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atatccgcgg tccatgtgtt ccaagagg                                      28

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atatgcggcc gcagtccctc ctcatggt                                      28

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atatccgcgg tcccggtgct cgcggcag                                      28

<210> SEQ ID NO 26
<211> LENGTH: 31
```

<212> TYPE: DNA
<213> ORGANISM: Artificial Sequence
<220> FEATURE:
<223> OTHER INFORMATION: Description of Artificial Sequence: Synthetic primer

<400> SEQUENCE: 26
atatgcggcc gcactcatgt ttcccctgat t                               31

<210> SEQ ID NO 27
<211> LENGTH: 1113
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(1113)

<400> SEQUENCE: 27

| cgg | tcc | cgg | tgc | tcg | cgg | cag | tgc | cag | gag | ggc | cag | gtg | cgc | cgg | gtc | 48 |
|-----|-----|-----|-----|-----|-----|-----|-----|-----|-----|-----|-----|-----|-----|-----|-----|----|
| Arg | Ser | Arg | Cys | Ser | Arg | Gln | Cys | Gln | Glu | Gly | Gln | Val | Arg | Arg | Val |    |
| 1   |     |     |     | 5   |     |     |     |     | 10  |     |     |     |     | 15  |     |    |

| aag | ggg | ttc | cac | tcc | tgc | tgc | tac | gac | tgt | gtg | gac | tgc | gag | gcg | ggc | 96 |
|-----|-----|-----|-----|-----|-----|-----|-----|-----|-----|-----|-----|-----|-----|-----|-----|----|
| Lys | Gly | Phe | His | Ser | Cys | Cys | Tyr | Asp | Cys | Val | Asp | Cys | Glu | Ala | Gly |    |
|     |     |     | 20  |     |     |     | 25  |     |     |     | 30  |     |     |     |     |    |

| agc | tac | cgg | caa | aac | cca | gac | gac | atc | gcc | tgc | acc | ttt | tgt | ggc | cag | 144 |
|-----|-----|-----|-----|-----|-----|-----|-----|-----|-----|-----|-----|-----|-----|-----|-----|-----|
| Ser | Tyr | Arg | Gln | Asn | Pro | Asp | Asp | Ile | Ala | Cys | Thr | Phe | Cys | Gly | Gln |     |
|     |     | 35  |     |     |     |     | 40  |     |     |     | 45  |     |     |     |     |     |

| gat | gag | tgg | tcc | ccg | gag | cga | agc | aca | cgc | tgc | ttc | cgc | cgc | agg | tct | 192 |
|-----|-----|-----|-----|-----|-----|-----|-----|-----|-----|-----|-----|-----|-----|-----|-----|-----|
| Asp | Glu | Trp | Ser | Pro | Glu | Arg | Ser | Thr | Arg | Cys | Phe | Arg | Arg | Arg | Ser |     |
| 50  |     |     |     |     | 55  |     |     |     |     | 60  |     |     |     |     |     |     |

| cgg | ttc | ctg | gca | tgg | ggc | gag | ccg | gct | gtg | ctg | ctg | ctc | ctg | ctg | 240 |
|-----|-----|-----|-----|-----|-----|-----|-----|-----|-----|-----|-----|-----|-----|-----|-----|
| Arg | Phe | Leu | Ala | Trp | Gly | Glu | Pro | Ala | Val | Leu | Leu | Leu | Leu | Leu |     |
| 65  |     |     |     | 70  |     |     |     |     | 75  |     |     |     |     | 80  |     |

| ctg | agc | ctg | gcg | ctg | ggc | ctt | gtg | ctg | gct | gct | ttg | ggg | ctg | ttc | gtt | 288 |
|-----|-----|-----|-----|-----|-----|-----|-----|-----|-----|-----|-----|-----|-----|-----|-----|-----|
| Leu | Ser | Leu | Ala | Leu | Gly | Leu | Val | Leu | Ala | Ala | Leu | Gly | Leu | Phe | Val |     |
|     |     |     |     | 85  |     |     |     |     | 90  |     |     |     | 95  |     |     |     |

| cac | cat | cgg | gac | agc | cca | ctg | gtt | cag | gcc | tcg | ggg | ggg | ccc | ctg | gcc | 336 |
|-----|-----|-----|-----|-----|-----|-----|-----|-----|-----|-----|-----|-----|-----|-----|-----|-----|
| His | His | Arg | Asp | Ser | Pro | Leu | Val | Gln | Ala | Ser | Gly | Gly | Pro | Leu | Ala |     |
|     |     |     | 100 |     |     |     |     | 105 |     |     |     | 110 |     |     |     |     |

| tgc | ttt | ggc | ctg | gtg | tgc | ctg | ggc | ctg | gtc | tgc | ctc | agc | gtc | ctc | ctg | 384 |
|-----|-----|-----|-----|-----|-----|-----|-----|-----|-----|-----|-----|-----|-----|-----|-----|-----|
| Cys | Phe | Gly | Leu | Val | Cys | Leu | Gly | Leu | Val | Cys | Leu | Ser | Val | Leu | Leu |     |
|     |     |     | 115 |     |     |     |     | 120 |     |     |     | 125 |     |     |     |     |

| ttc | cct | ggc | cag | ccc | agc | cct | gcc | cga | tgc | ctg | gcc | cag | cag | ccc | ttg | 432 |
|-----|-----|-----|-----|-----|-----|-----|-----|-----|-----|-----|-----|-----|-----|-----|-----|-----|
| Phe | Pro | Gly | Gln | Pro | Ser | Pro | Ala | Arg | Cys | Leu | Ala | Gln | Gln | Pro | Leu |     |
|     | 130 |     |     |     |     | 135 |     |     |     |     | 140 |     |     |     |     |     |

| tcc | cac | ctc | ccg | ctc | acg | ggc | tgc | ctg | agc | aca | ctc | ttc | ctg | cag | gcg | 480 |
|-----|-----|-----|-----|-----|-----|-----|-----|-----|-----|-----|-----|-----|-----|-----|-----|-----|
| Ser | His | Leu | Pro | Leu | Thr | Gly | Cys | Leu | Ser | Thr | Leu | Phe | Leu | Gln | Ala |     |
| 145 |     |     |     | 150 |     |     |     |     | 155 |     |     |     |     | 160 |     |     |

| gcc | gag | atc | ttc | gtg | gag | tca | gaa | ctg | cct | ctg | agc | tgg | gca | gac | cgg | 528 |
|-----|-----|-----|-----|-----|-----|-----|-----|-----|-----|-----|-----|-----|-----|-----|-----|-----|
| Ala | Glu | Ile | Phe | Val | Glu | Ser | Glu | Leu | Pro | Leu | Ser | Trp | Ala | Asp | Arg |     |
|     |     |     | 165 |     |     |     |     | 170 |     |     |     | 175 |     |     |     |     |

| ctg | agt | ggc | tgc | ctg | cgg | ggg | ccc | tgg | gcc | tgg | ctg | gtg | gtg | ctg | ctg | 576 |
|-----|-----|-----|-----|-----|-----|-----|-----|-----|-----|-----|-----|-----|-----|-----|-----|-----|
| Leu | Ser | Gly | Cys | Leu | Arg | Gly | Pro | Trp | Ala | Trp | Leu | Val | Val | Leu | Leu |     |
|     |     | 180 |     |     |     |     | 185 |     |     |     | 190 |     |     |     |     |     |

| gcc | atg | ctg | gtg | gag | gtc | gca | ctg | tgc | acc | tgg | tac | ctg | gtg | gcc | ttc | 624 |
|-----|-----|-----|-----|-----|-----|-----|-----|-----|-----|-----|-----|-----|-----|-----|-----|-----|
| Ala | Met | Leu | Val | Glu | Val | Ala | Leu | Cys | Thr | Trp | Tyr | Leu | Val | Ala | Phe |     |
|     |     | 195 |     |     |     |     | 200 |     |     |     | 205 |     |     |     |     |     |

| ccg | ccg | gag | gtg | gtg | acg | gac | tgg | cac | atg | ctg | ccc | acg | gag | gcg | ctg | 672 |
|-----|-----|-----|-----|-----|-----|-----|-----|-----|-----|-----|-----|-----|-----|-----|-----|-----|
| Pro | Pro | Glu | Val | Val | Thr | Asp | Trp | His | Met | Leu | Pro | Thr | Glu | Ala | Leu |     |
|     | 210 |     |     |     |     | 215 |     |     |     |     | 220 |     |     |     |     |     |

```
gtg cac tgc cgc aca cgc tcc tgg gtc agc ttc ggc cta gcg cac gcc      720
Val His Cys Arg Thr Arg Ser Trp Val Ser Phe Gly Leu Ala His Ala
225                 230                 235                 240 acc aat gcc acg ctg gcc ttt ctc tgc ttc ctg ggc act ttc ctg gtg      768
Thr Asn Ala Thr Leu Ala Phe Leu Cys Phe Leu Gly Thr Phe Leu Val
                245                 250                 255 cgg agc cag ccg ggc cgc tac aac cgt gcc cgt ggc ctc acc ttt gcc      816
Arg Ser Gln Pro Gly Arg Tyr Asn Arg Ala Arg Gly Leu Thr Phe Ala
            260                 265                 270 atg ctg gcc tac ttc atc acc tgg gtc tcc ttt gtg ccc ctc ctg gcc      864
Met Leu Ala Tyr Phe Ile Thr Trp Val Ser Phe Val Pro Leu Leu Ala
        275                 280                 285 aat gtg cag gtg gtc ctc agg ccc gcc gtg cag atg ggc gcc ctc ctg      912
Asn Val Gln Val Val Leu Arg Pro Ala Val Gln Met Gly Ala Leu Leu
    290                 295                 300 ctc tgt gtc ctg ggc atc ctg gct gcc ttc cac ctg ccc agg tgt tac      960
Leu Cys Val Leu Gly Ile Leu Ala Ala Phe His Leu Pro Arg Cys Tyr
305                 310                 315                 320 ctg ctc atg cgg cag cca ggg ctc aac acc ccc gag ttc ttc ctg gga     1008
Leu Leu Met Arg Gln Pro Gly Leu Asn Thr Pro Glu Phe Phe Leu Gly
                325                 330                 335 ggg ggc cct ggg gat gcc caa ggc cag aat gac ggg aac aca gga aat     1056
Gly Gly Pro Gly Asp Ala Gln Gly Gln Asn Asp Gly Asn Thr Gly Asn
            340                 345                 350 cag ggg aaa cat gag tgc ggc cgc cag cct gaa ctc gct cct gaa gac     1104
Gln Gly Lys His Glu Cys Gly Arg Gln Pro Glu Leu Ala Pro Glu Asp
        355                 360                 365 ccg gaa gat                                                         1113
Pro Glu Asp
    370

<210> SEQ ID NO 28
<211> LENGTH: 371
<212> TYPE: PRT
<213> ORGANISM: Artificial Sequence
<220> FEATURE:
<223> OTHER INFORMATION: Synthetic Construct

<400> SEQUENCE: 28

Arg Ser Arg Cys Ser Arg Gln Cys Gln Glu Gly Gln Val Arg Arg Val
1               5                   10                  15

Lys Gly Phe His Ser Cys Cys Tyr Asp Cys Val Asp Cys Glu Ala Gly
                20                  25                  30

Ser Tyr Arg Gln Asn Pro Asp Asp Ile Ala Cys Thr Phe Cys Gly Gln
            35                  40                  45

Asp Glu Trp Ser Pro Glu Arg Ser Thr Arg Cys Phe Arg Arg Arg Ser
    50                  55                  60

Arg Phe Leu Ala Trp Gly Glu Pro Ala Val Leu Leu Leu Leu Leu Leu
65                  70                  75                  80

Leu Ser Leu Ala Leu Gly Leu Val Leu Ala Ala Leu Gly Leu Phe Val
                85                  90                  95

His His Arg Asp Ser Pro Leu Val Gln Ala Ser Gly Gly Pro Leu Ala
            100                 105                 110

Cys Phe Gly Leu Val Cys Leu Gly Leu Val Cys Leu Ser Val Leu Leu
        115                 120                 125

Phe Pro Gly Gln Pro Ser Pro Ala Arg Cys Leu Ala Gln Gln Pro Leu
    130                 135                 140

Ser His Leu Pro Leu Thr Gly Cys Leu Ser Thr Leu Phe Leu Gln Ala
145                 150                 155                 160
```

-continued

```
Ala Glu Ile Phe Val Glu Ser Glu Leu Pro Leu Ser Trp Ala Asp Arg
            165                 170                 175

Leu Ser Gly Cys Leu Arg Gly Pro Trp Ala Trp Leu Val Val Leu Leu
            180                 185                 190

Ala Met Leu Val Glu Val Ala Leu Cys Thr Trp Tyr Leu Val Ala Phe
            195                 200                 205

Pro Pro Glu Val Val Thr Asp Trp His Met Leu Pro Thr Glu Ala Leu
            210                 215                 220

Val His Cys Arg Thr Arg Ser Trp Val Ser Phe Gly Leu Ala His Ala
225                 230                 235                 240

Thr Asn Ala Thr Leu Ala Phe Leu Cys Phe Leu Gly Thr Phe Leu Val
            245                 250                 255

Arg Ser Gln Pro Gly Arg Tyr Asn Arg Ala Arg Gly Leu Thr Phe Ala
            260                 265                 270

Met Leu Ala Tyr Phe Ile Thr Trp Val Ser Phe Val Pro Leu Leu Ala
            275                 280                 285

Asn Val Gln Val Val Leu Arg Pro Ala Val Gln Met Gly Ala Leu Leu
            290                 295                 300

Leu Cys Val Leu Gly Ile Leu Ala Ala Phe His Leu Pro Arg Cys Tyr
305                 310                 315                 320

Leu Leu Met Arg Gln Pro Gly Leu Asn Thr Pro Glu Phe Phe Leu Gly
            325                 330                 335

Gly Gly Pro Gly Asp Ala Gln Gly Gln Asn Asp Gly Asn Thr Gly Asn
            340                 345                 350

Gln Gly Lys His Glu Cys Gly Arg Gln Pro Glu Leu Ala Pro Glu Asp
            355                 360                 365

Pro Glu Asp
    370

<210> SEQ ID NO 29
<211> LENGTH: 11
<212> TYPE: DNA
<213> ORGANISM: Artificial Sequence
<220> FEATURE:
<223> OTHER INFORMATION: consensus sequence

<400> SEQUENCE: 29
ggggactttc c                                                    11
```